(12) United States Patent
Hysi et al.

(10) Patent No.: US 12,295,702 B2
(45) Date of Patent: May 13, 2025

(54) METHOD AND SYSTEM FOR PHOTOACOUSTIC IMAGING OF TISSUE AND ORGAN FIBROSIS

(71) Applicants: Eno Hysi, Toronto (CA); Michael C. Kolios, Ancaster (CA); Unity Health Toronto, Toronto (CA)

(72) Inventors: Eno Hysi, Toronto (CA); Michael C. Kolios, Ancaster (CA); Darren A. Yuen, Toronto (CA)

(73) Assignees: Eno Hysi, Toronto (CA); Michael Kolios, Toronto (CA); Unity Health Toronto, Toronto (CA)

( * ) Notice: Subject to any disclaimer, the term of this patent is extended or adjusted under 35 U.S.C. 154(b) by 130 days.

(21) Appl. No.: 17/789,107

(22) PCT Filed: Dec. 23, 2020

(86) PCT No.: PCT/CA2020/051791
§ 371 (c)(1),
(2) Date: Jun. 24, 2022

(87) PCT Pub. No.: WO2021/127784
PCT Pub. Date: Jul. 1, 2021

(65) Prior Publication Data
US 2023/0050956 A1   Feb. 16, 2023

Related U.S. Application Data

(60) Provisional application No. 62/953,235, filed on Dec. 24, 2019.

(51) Int. Cl.
*A61B 5/00*   (2006.01)
*A61B 5/08*   (2006.01)
(Continued)

(52) U.S. Cl.
CPC .......... *A61B 5/0095* (2013.01); *A61B 5/0036* (2018.08); *A61B 5/201* (2013.01);
(Continued)

(58) Field of Classification Search
CPC ......................... G01N 29/2418; A61B 5/0095; A61B 8/5223; A61B 5/0036
See application file for complete search history.

(56) References Cited

U.S. PATENT DOCUMENTS 4,956,272 A * 9/1990 Kakimoto ................ A01N 1/02
435/1.1
7,146,204 B2   12/2006 Degani et al.
(Continued)

FOREIGN PATENT DOCUMENTS

EP       3518771 B1 * 9/2020 ........... A61B 8/0833
WO    2019144232 A1   8/2019

OTHER PUBLICATIONS

Hysi E et al., Photoacoustic imaging of kidney fibrosis for assessing pretransplant organ quality. JCI Insight. May 21, 2020;5(10): e136995. doi: 10.1172/jci.insight.136995. PMID: 32298239; PMCID: PMC725 (Year: 2020).*

(Continued)

*Primary Examiner* — John D Li
(74) *Attorney, Agent, or Firm* — SMART & BIGGAR LP; Tonino Rosario Orsi

(57) ABSTRACT

Various embodiments are described herein for a system and associated method for performing collagen assessment of an object using Photoacoustic Image (PA) data obtained for the object, wherein the method is performed by a processing unit and the method comprises: obtaining beamformed PA image data for the object using at least three wavelengths related to chromophores including collagen, oxyhemoglobin and deoxyhemoglobin, the three wavelengths being less than
(Continued)

1000 nm; performing spectral decomposition on the beam-formed PA image data using the three wavelengths to obtain data that is used for generating at least one collagen map; and determining a collagen score for the at least one collagen map.

23 Claims, 21 Drawing Sheets
Specification includes a Sequence Listing.

(51) Int. Cl.
    *A61B 5/20*           (2006.01)
    *A61B 8/00*           (2006.01)

(52) U.S. Cl.
CPC .......... *A61B 5/4848* (2013.01); *A61B 8/5223* (2013.01); *A61B 8/5261* (2013.01); *A61B 5/08* (2013.01); *A61B 5/4244* (2013.01); *A61B 5/425* (2013.01); *A61B 5/4255* (2013.01); *A61B 5/441* (2013.01); *A61B 5/4519* (2013.01)

(56) References Cited

U.S. PATENT DOCUMENTS

| | | | |
|---|---|---|---|
| 9,737,256 | B2 | 8/2017 | Chen et al. |
| 9,928,347 | B2 | 3/2018 | El-Baz et al. |
| 2010/0094561 | A1* | 4/2010 | Masumura ............ A61B 5/0097 73/632 |
| 2011/0054292 | A1* | 3/2011 | Hirson ................ G01S 15/8993 600/407 |
| 2016/0354496 | A1 | 12/2016 | Jung et al. |
| 2018/0008235 | A1* | 1/2018 | Hayashi ............... A61B 5/0095 |
| 2019/0298247 | A1 | 10/2019 | Bennett et al. |
| 2020/0178933 | A1* | 6/2020 | Imai ..................... A61B 8/5223 |
| 2020/0329974 | A1* | 10/2020 | Fadhel ................ G01N 29/2418 |

OTHER PUBLICATIONS

Bülow RD, Boor P. Extracellular Matrix in Kidney Fibrosis: More Than Just a Scaffold. J Histochem Cytochem. Sep. 2019;67(9):643-661. doi: 10.1369/0022155419849388. Epub May 22, 2019. PMID: 31116062; PMCID: PMC6713975. (Year: 2019).*

Williams WW, Taheri D, Tolkoff-Rubin N, Colvin RB. Clinical role of the renal transplant biopsy. Nat Rev Nephrol. Jan. 10, 2012;8(2):110-21. doi: 10.1038/nrneph.2011.213. PMID: 22231130; PMCID: PMC3716017. (Year: 2012).*

Fadhel MN, Hysi E, Strohm EM, Kolios MC. Optical and photoacoustic radiofrequency spectroscopic analysis for detecting red blood cell death. J. Biophotonics. 2019; 12:e201800431. https://doi.org/10.1002/jbio.201800431 (Year: 2019).*

Hysi et al., "Photoacoustic imaging of kidney fibrosis for assessing pretransplant organ quality" JCI Insight. May 21, 2020;5(10):e136995 (11 pages).

"Canadian Organ Replacement Register Metadata (CORR) | CIHI—Treatment of End-Stage Organ Failure in Canada," May 2, 2019. [Online]. Available: https://www.cihi.ca/en/canadian-organ-replacement-register-metadata-corr. [Accessed: Jul. 28, 2019] (3 pages).

United States Renal Data System (USRDS), "Annual Data Report," 2018 Annual Data Report. [Online]. Available: https://web.archive.org/web/20191006010307/https://www.usrds.org/. [Accessed: Sep. 26, 2019] (14 pages).

R. A. Wolfe et al., "Comparison of mortality in all patients on dialysis, patients on dialysis awaiting transplantation, and recipients of a first cadaveric transplant," N. Engl. J. Med., vol. 341, No. 23, pp. 1725-1730, Dec. 1999 (6 pages).

F. K. Port et al., "Comparison of survival probabilities for dialysis patients vs cadaveric renal transplant recipients," JAMA, vol. 270, No. 11, pp. 1339-1343, Sep. 1993 (5 pages).

A. Laupacis et al., "A study of the quality of life and cost-utility of renal transplantation," Kidney Int., vol. 50, No. 1, pp. 235-242, Jul. 1996 (8 pages).

"Facing the Facts—The Kidney Foundation of Canada | La Fondation canadienne du rein." [Online]. Available: https://web.archive.org/web/20190727152719/https://www.kidney.ca/facing-the-facts. [Accessed: Jul. 28, 2019] (1 page).

J. Schold, et al., "Half of kidney transplant candidates who are older than 60 years now placed on the waiting list will die before receiving a deceased-donor transplant," Clin. J. Am. Soc. Nephrol. CJASN, vol. 4, No. 7, pp. 1239-1245, Jul. 2009 (7 pages).

K. De Vusser et al., "The predictive value of kidney allograft baseline biopsies for long-term graft survival," J. Am. Soc. Nephrol. JASN, vol. 24, No. 11, pp. 1913-1923, Nov. 2013 (11 pages).

A. Srivastava et al., "The Prognostic Value of Histopathologic Lesions in Native Kidney Biopsy Specimens: Results from the Boston Kidney Biopsy Cohort Study," J. Am. Soc. Nephrol. JASN, vol. 29, No. 8, pp. 2213-2224, Aug. 2018 (12 pages).

F. M. E. G. Steegh et al., "Early loss of peritubular capillaries after kidney transplantation," J. Am. Soc. Nephrol. JASN, vol. 22, No. 6, pp. 1024-1029, Jun. 2011 (6 pages).

M. Naesens et al., "Chronic histological damage in early indication biopsies is an independent risk factor for late renal allograft failure," Am. J. Transplant. Off. J. Am. Soc. Transplant. Am. Soc. Transpl. Surg., vol. 13, No. 1, pp. 86-99, Jan. 2013 (14 pages).

D. Tampe and M. Zeisberg, "Potential approaches to reverse or repair renal fibrosis," Nat. Rev. Nephrol., vol. 10, No. 4, pp. 226-237, Apr. 2014 (48 pages).

C. J. Wang, et al., "The Donor Kidney Biopsy and Its Implications in Predicting Graft Outcomes: A Systematic Review," Am. J. Transplant. Off. J. Am. Soc. Transplant. Am. Soc. Transpl. Surg., vol. 15, No. 7, pp. 1903-1914, Jul. 2015 (12 pages).

H. J. Wang et al., "On the influence of sample size on the prognostic accuracy and reproducibility of renal transplant biopsy," Nephrol. Dial. Transplant. Off. Publ. Eur. Dial. Transpl. Assoc.—Eur. Ren. Assoc., vol. 13, No. 1, pp. 165-172, Jan. 1998 (8 pages).

Williams et al., "Clinical role of the renal transplant biopsy," Nat. Rev. Nephrol., vol. 8, No. 2, pp. 110-121, Jan. 2012 (26 pages).

G. Leung et al., "Could MRI Be Used To Image Kidney Fibrosis? A Review of Recent Advances and Remaining Barriers," Clin. J. Am. Soc. Nephrol. CJASN, vol. 12, No. 6, pp. 1019-1028, Jun. 2017 (10 pages).

L. V. Wang and S. Hu, "Photoacoustic tomography: in vivo imaging from organelles to organs," Science, vol. 335, No. 6075, pp. 1458-1462, Mar. 2012 (12 pages).

L. V. Wang and J. Yao, "A practical guide to photoacoustic tomography in the life sciences," Nat. Methods, vol. 13, No. 8, pp. 627-638, Aug. 2016 (42 pages).

J. Yao and L. V. Wang, "Photoacoustic tomography: fundamentals, advances and prospects," Contrast Media Mol. Imaging, vol. 6, No. 5, pp. 332-345, Oct. 2011 (29 pages).

R. J. Paproski et al., "Multi-wavelength photoacoustic imaging of inducible tyrosinase reporter gene expression in xenograft tumors," Sci. Rep., vol. 4, No. 1, May 2015 (7 pages).

B. Cox et al., "Quantitative spectroscopic photoacoustic imaging: a review," J. Biomed. Opt., vol. 17, No. 6, p. 061202, Jun. 2012 (23 pages).

J. Laufer et al., "In vivo photoacoustic imaging of mouse embryos," J. Biomed. Opt., vol. 17, No. 6, pp. 0612201-0612208, 2012 (9 pages).

D. Razansky et al., "Multispectral opto-acoustic tomography of deep-seated fluorescent proteins in vivo," Nat. Photonics, vol. 3, No. 7, pp. 412-417, Jul. 2009 (6 pages).

A. A. Eddy, "Molecular insights into renal interstitial fibrosis," J. Am. Soc. Nephrol. JASN, vol. 7, No. 12, pp. 2495-2508, Dec. 1996 (14 pages).

V. Ntziachristos et al., "Looking and listening to light: the evolution of whole-body photonic imaging," Nat. Biotechnol., vol. 23, No. 3, pp. 313-320, Mar. 2005 (27 pages).

R. L. Chevalier et al., "Ureteral obstruction as a model of renal interstitial fibrosis and obstructive nephropathy," Kidney Int., vol. 75, No. 11, pp. 1145-1152, Jun. 2009 (8 pages).

(56) References Cited

OTHER PUBLICATIONS

A. Kirpalani et al., "Magnetic Resonance Elastography to Assess Fibrosis in Kidney Allografts," Clin. J. Am. Soc. Nephrol. CJASN, vol. 12, No. 10, pp. 1671-1679, Oct. 2017 (9 pages).
I. Y. Petrova et al., "Optoacoustic monitoring of blood hemoglobin concentration: a pilot clinical study," Opt. Lett., vol. 30, No. 13, pp. 1677-1679, 2005 (3 pages).
T. Vu et al., "Listening to tissues with new light: recent technological advances in photoacoustic imaging," J. Opt., 2019 (20 pages).
P. Shao et al., "Estimating optical absorption, scattering, and Grueneisen distributions with multiple-illumination photoacoustic tomography," Appl. Opt., vol. 50, No. 19, pp. 3145-3154, 2011 (10 pages).
S. Moghazi et al., "Correlation of renal histopathology with sonographic findings," Kidney Int., vol. 67, No. 4, pp. 1515-1520, Apr. 2005 (6 pages).
F. G. Cosio et al., "Kidney allograft fibrosis and atrophy early after living donor transplantation," Am. J. Transplant. Off. J. Am. Soc. Transplant. Am. Soc. Transpl. Surg., vol. 5, No. 5, pp. 1130-1136, May 2005 (7 pages).
P. S. Rao et al., "A comprehensive risk quantification score for deceased donor kidneys: the kidney donor risk index," Transplantation, vol. 88, No. 2, pp. 231-236, Jul. 2009 (6 pages).
C. J. E. Watson et al., "A simplified donor risk index for predicting outcome after deceased donor kidney transplantation," Transplantation, vol. 93, No. 3, pp. 314-318, Feb. 2012 (5 pages).
A. Debout et al., "Each additional hour of cold ischemia time significantly increases the risk of graft failure and mortality following renal transplantation," Kidney Int., vol. 87, No. 2, pp. 343-349, Feb. 2015 (7 pages).
J. E. Locke et al., "Outcomes of kidneys from donors after cardiac death: implications for allocation and preservation," Am. J. Transplant. Off. J. Am. Soc. Transplant. Am. Soc. Transpl. Surg., vol. 7, No. 7, pp. 1797-1807, Jul. 2007 (11 pages).
J. D. Mezrich et al., "Differential Outcomes of Expanded-Criteria Donor Renal Allografts According to Recipient Age," Clin. J. Am. Soc. Nephrol. CJASN, vol. 7, No. 7, pp. 1163-1171, Jul. 2012 (9 pages).
O. Aubert et al., "Long term outcomes of transplantation using kidneys from expanded criteria donors: prospective, population based cohort study," BMJ, vol. 351, p. h3557, Jul. 2015 (9 pages).
A. O. Ojo et al., "Survival in recipients of marginal cadaveric donor kidneys compared with other recipients and wait-listed transplant candidates," J. Am. Soc. Nephrol. JASN, vol. 12, No. 3, pp. 589-597, Mar. 2001 (9 pages).
R. Arndt et al., "Noninvasive evaluation of renal allograft fibrosis by transient elastography—a pilot study," Transpl. Int. Off. J. Eur. Soc. Organ Transplant., vol. 23, No. 9, pp. 871-877, Sep. 2010 (7 pages).
L. Li et al., "Single-impulse panoramic photoacoustic computed tomography of small-animal whole-body dynamics at high spatiotemporal resolution," Nat. Biomed. Eng., vol. 1, No. 5, p. 0071, May 2017 (42 pages).
F. Knieling et al., "Multispectral Optoacoustic Tomography for Assessment of Crohn's Disease Activity," N. Engl. J. Med., vol. 376, No. 13, pp. 1292-1294, 2017 (3 pages).
E. I. Neuschler et al., "A Pivotal Study of Optoacoustic Imaging to Diagnose Benign and Malignant Breast Masses: A New Evaluation Tool for Radiologists," Radiology, p. 172228, Nov. 2017 (15 pages).
L. Lin et al., "Single-breath-hold photoacoustic computed tomography of the breast," Nat. Commun., vol. 9, No. 1, p. 2352, 15 2018 (9 pages).
P. J. Van Den Berg et al., "Preclinical detection of liver fibrosis using dual-modality photoacoustic/ultrasound system," Biomed. Opt. Express, vol. 7, No. 12, pp. 5081-5091, Nov. 2016 (11 pages).
Y. Zhu et al., "Identifying intestinal fibrosis and inflammation by spectroscopic photoacoustic imaging: an animal study in vivo," Biomed. Opt. Express, vol. 9, No. 4, pp. 1590-1600, Mar. 2018 (11 pages).
H. Lei et al., "Characterizing intestinal strictures of Crohn's disease in vivo by endoscopic photoacoustic imaging," Biomed. Opt. Express, vol. 10, No. 5, pp. 2542-2555, May 2019 (14 pages).
M. Schwarz et al., "Motion correction in optoacoustic mesoscopy," Sci. Rep., vol. 7, No. 1, pp. 1-9, Sep. 2017 (9 pages).
J. Aguirre et al., "Precision assessment of label-free psoriasis biomarkers with ultra-broadband optoacoustic mesoscopy," Nat. Biomed. Eng., vol. 1, No. 5, p. 0068, May 2017 (33 pages).
T. D. Hewitson et al., "Estrogens do not protect, but androgens exacerbate, collagen accumulation in the female mouse kidney after ureteric obstruction," Life Sci., vol. 158, pp. 130-136, Aug. 2016 (7 pages).
R. S. Hijmans et al., "Urinary collagen degradation products as early markers of progressive renal fibrosis," J. Transl. Med., vol. 15, Mar. 2017 (11 pages).
R. D. Bülow and P. Boor, "Extracellular Matrix in Kidney Fibrosis: More Than Just a Scaffold," J. Histochem. Cytochem. Off. J. Histochem. Soc., p. 22155419849388, May 2019 (19 pages).
Q. Yuan, R. J. Tan, and Y. Liu, "Myofibroblast in Kidney Fibrosis: Origin, Activation, and Regulation," in Renal Fibrosis: Mechanisms and Therapies, B.-C. Liu, H.-Y. Lan, and L.-L. Lv, Eds. Singapore: Springer Singapore, 2019, pp. 253-283 (31 pages).
S. Ricard-Blum, G. Baffet, and N. Théret, "Molecular and tissue alterations of collagens in fibrosis," Matrix Biol. J. Int. Soc. Matrix Biol., vol. 68-69, pp. 122-149, 2018 (28 pages).
M. A. Karsdal et al., "Novel insights into the function and dynamics of extracellular matrix in liver fibrosis," Am. J. Physiol. Gastrointest. Liver Physiol., vol. 308, No. 10, pp. G807-G830, May 2015 (37 pages).
K. M. Mak, C. Y. M. Png, and D. J. Lee, "Type V Collagen in Health, Disease, and Fibrosis," Anat. Rec. Hoboken NJ 2007, vol. 299, No. 5, pp. 613-629, May 2016 (17 pages).
H. Yang and Z. Shu, "The extraction of collagen protein from pigskin," 2014 (5 pages).
A. Needles et al., "Development and initial application of a fully integrated photoacoustic micro-ultrasound system," IEEE Trans. Ultrason. Ferroelectr. Freq. Control, vol. 60, No. 5, pp. 888-897, May 2013 (10 pages).
D. A. Belsley, E. Kuh, and R. E. Welsch, "Detecting and Assessing Collinearity," in Regression Diagnostics, John Wiley & Sons, Ltd, 2005, pp. 85-191 (107 pages).
S. G. Szeto et al., "YAP/TAZ Are Mechanoregulators of TGF-β-Smad Signaling and Renal Fibrogenesis," J. Am. Soc. Nephrol., vol. 27, No. 10, pp. 3117-3128, Oct. 2016 (12 pages).
R. A. Fisher, "Statistical Methods for Research Workers," in Breakthroughs in Statistics: Methodology and Distribution, S. Kotz and N. L. Johnson, Eds. New York, NY: Springer New York, 1992, pp. 66-70 (5 pages).
G. A. F. Seber and A. J. Lee, Linear Regression Analysis. John Wiley & Sons, 2012 (62 pages).
Prahl, Tabulated Molar Extinction Coefficient for Hemoglobin in Water, accessed Mar. 6, 2024 <https://omlc.org/spectra/hemoglobin/summary.html> (7 pages).
S. K. V. Sekar et al., "Diffuse optical characterization of collagen absorption from 500 to 1700 nm," J. Biomed. Opt., vol. 22, No. 1, p. 15006, Jan. 2017 (7 pages).
B. T. Cox et al., "Two-dimensional quantitative photoacoustic image reconstruction of absorption distributions in scattering media by use of a simple iterative method," Appl. Opt., vol. 45, No. 8, pp. 1866-1875, Mar. 2006 (10 pages).
R. J. Zemp, "Quantitative photoacoustic tomography with multiple optical sources," Appl. Opt., vol. 49, No. 18, pp. 3566-3572, Jun. 2010 (7 pages).
A. Pulkkinen et al., "Direct Estimation of Optical Parameters from Photoacoustic Time Series in Quantitative Photoacoustic Tomography," IEEE Trans. Med. Imaging, vol. 35, No. 11, pp. 2497-2508, 2016 (12 pages).
B. T. Cox, J. G. Laufer, and P. C. Beard, "The challenges for quantitative photoacoustic imaging," presented at the Progress in Biomedical Optics and Imaging—Proceedings of SPIE, 2009, vol. 7177 (10 pages).
L. V. Wang, "Tutorial on Photoacoustic Microscopy and Computed Tomography," IEEE J. Sel. Top. Quantum Electron., vol. 14, No. 1, pp. 171-179, 2008 (9 pages).

(56) References Cited

OTHER PUBLICATIONS

F. K. Port et al., "Donor characteristics associated with reduced graft survival: an approach to expanding the pool of kidney donors," Transplantation, vol. 74, No. 9, pp. 1281-1286, Nov. 2002 (6 pages).
Q. Sun et al., "Elastin imaging enables noninvasive staging and treatment monitoring of kidney fibrosis," Sci. Transl. Med., vol. 11, No. 486, p. eaat4865, Apr. 2019 (31 pages).
B. R. Rosengard et al., "Report of the Crystal City meeting to maximize the use of organs recovered from the cadaver donor," Am. J. Transplant. Off. J. Am. Soc. Transplant. Am. Soc. Transpl. Surg., vol. 2, No. 8, pp. 701-711, Sep. 2002 (11 pages).
P. Regensburger et al., "Detection of collagens by multispectral optoacoustic tomography as an imaging biomarker for Duchenne muscular dystrophy," Nat. Med., pp. 1-11, Dec. 2019 (24 pages).
T.-H. Bok, E. Hysi, and M. C. Kolios, "Simultaneous assessment of red blood cell aggregation and oxygen saturation under pulsatile flow using high-frequency photoacoustics," Biomed. Opt. Express, vol. 7, No. 7, pp. 2769-2780, Jun. 2016 (12 pages).
E. Hysi et al., "Photoacoustic signal characterization of cancer treatment response: Correlation with changes in tumor oxygenation," Photoacoustics, vol. 5, pp. 25-35, Mar. 2017 (11 pages).
International Search Report and Written Opinion mailed Mar. 5, 2021 in International Patent Application No. PCT/CA2020/051791 (14 pages).

\* cited by examiner

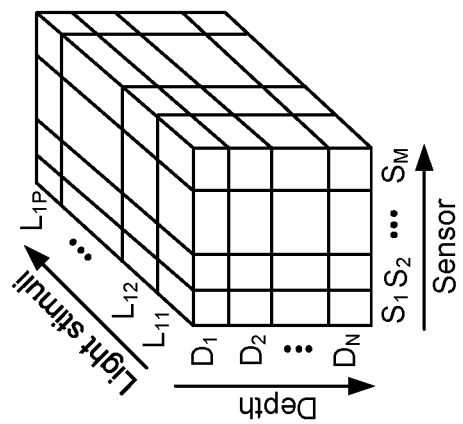
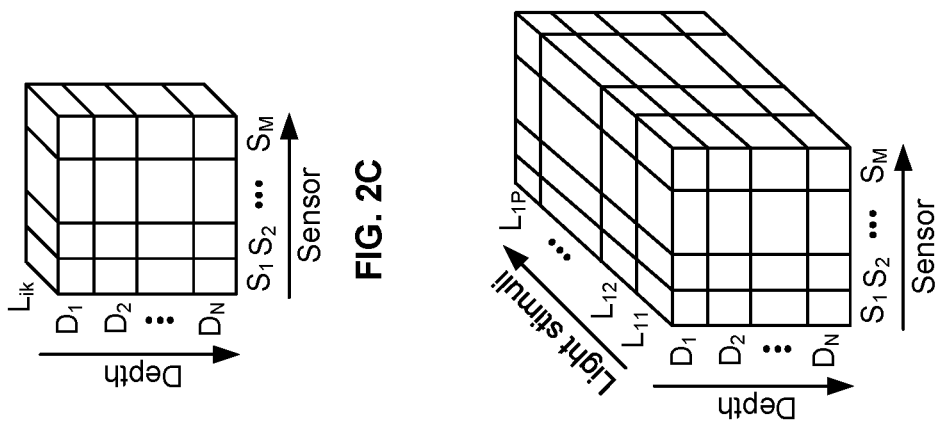
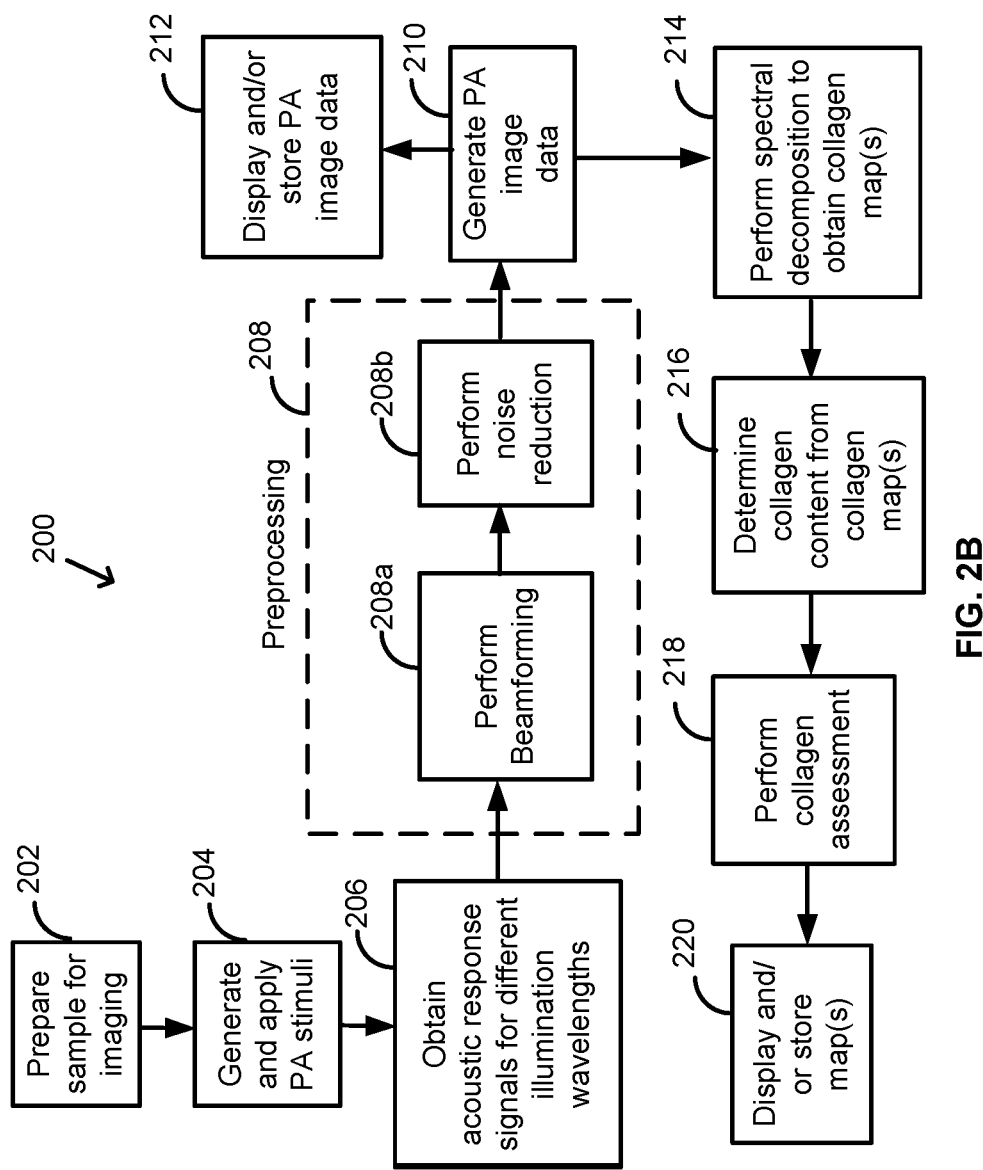

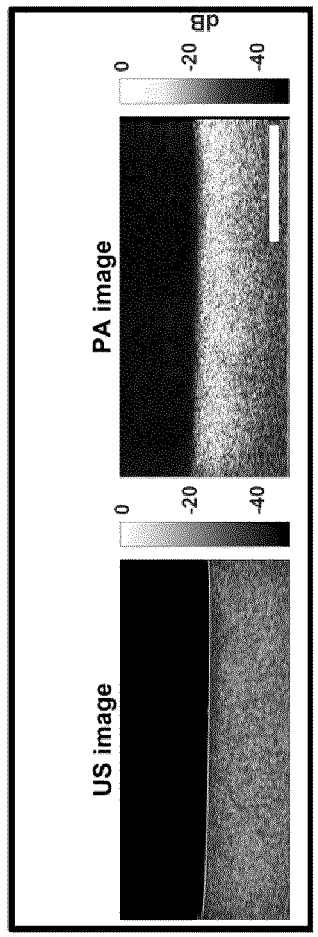
FIG. 3B
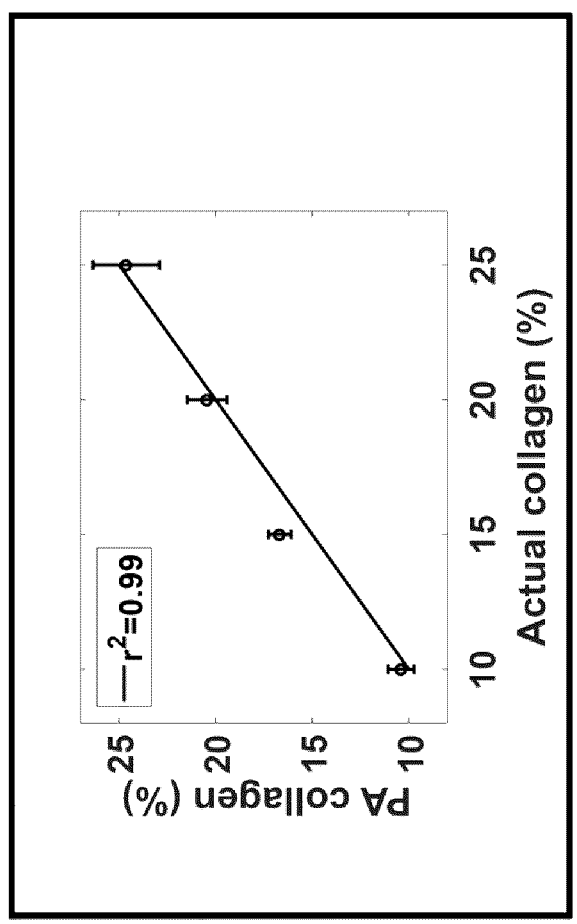
FIG. 3C
FIG. 3A

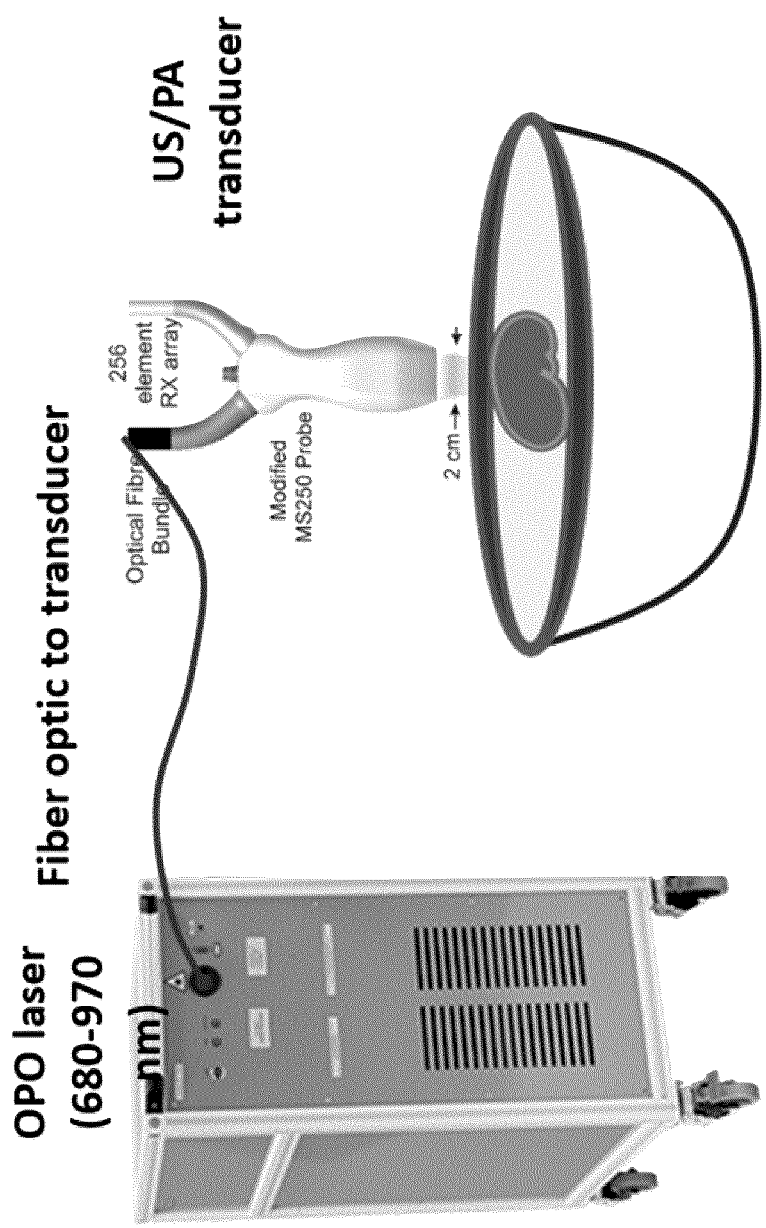
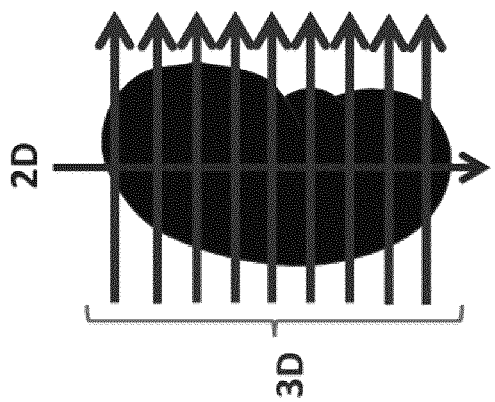
FIG. 4A
FIG. 4B

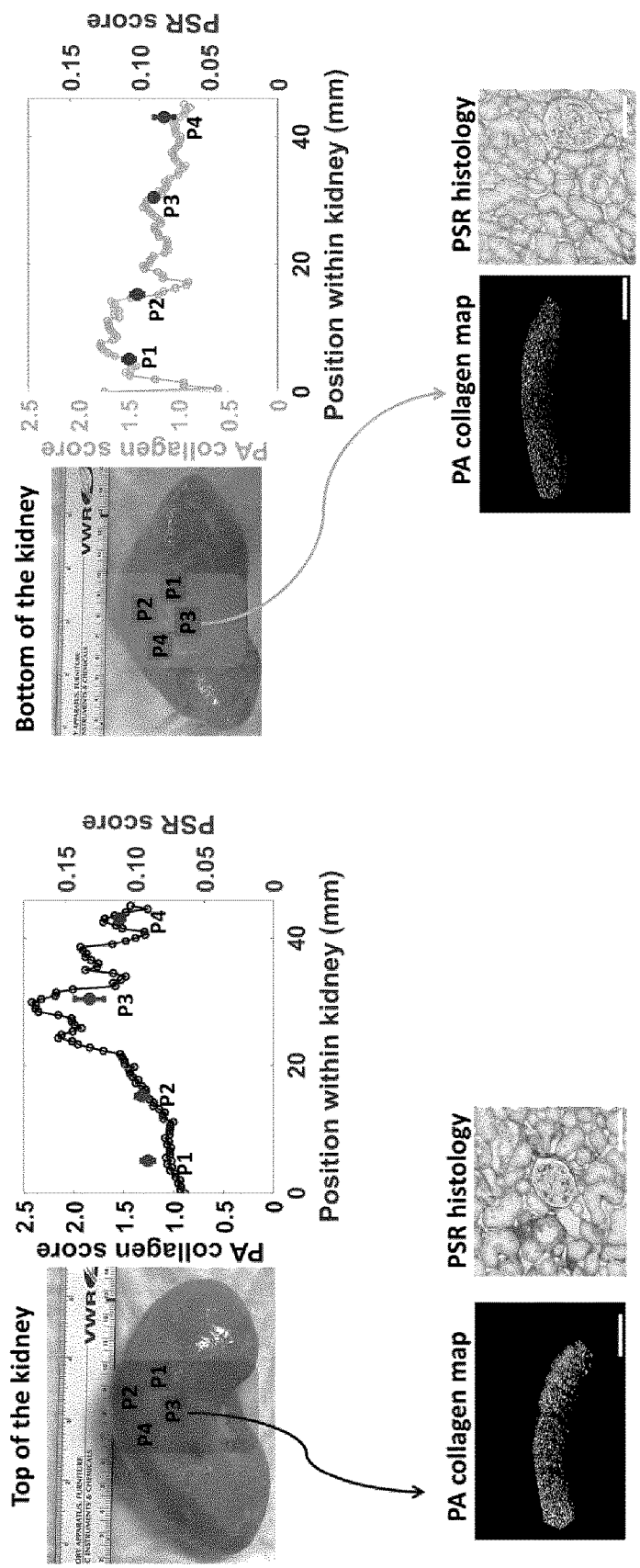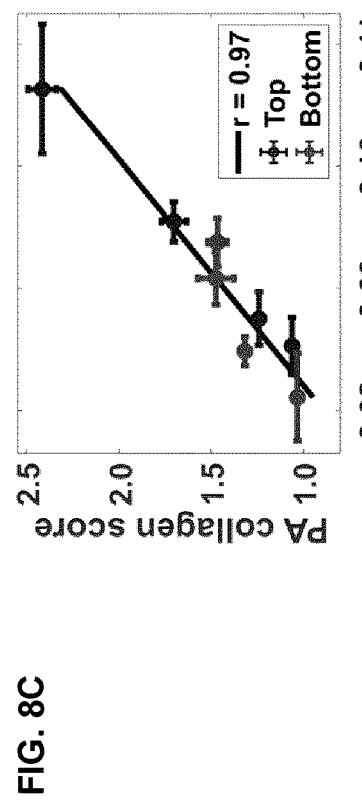
FIG. 8C
FIG. 8D
FIG. 8E

Kidney 5 | Kidney 4 | Kidney 3 | Kidney 2 | Kidney 1

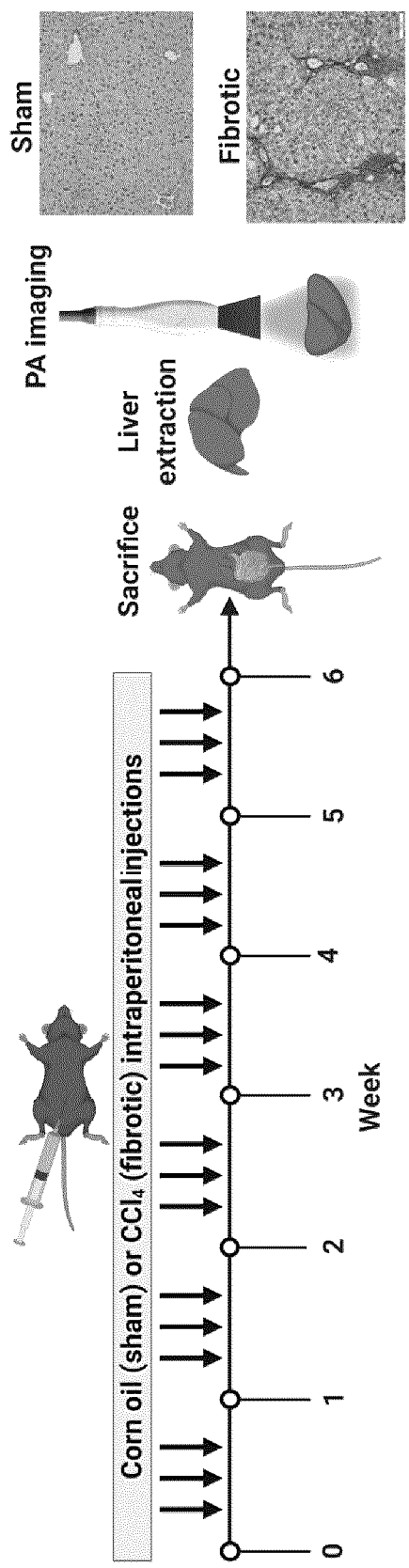
FIG. 11
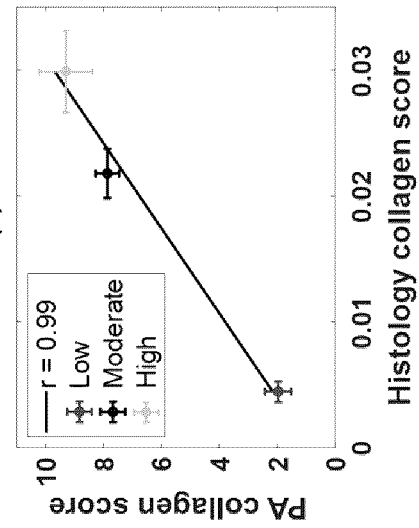
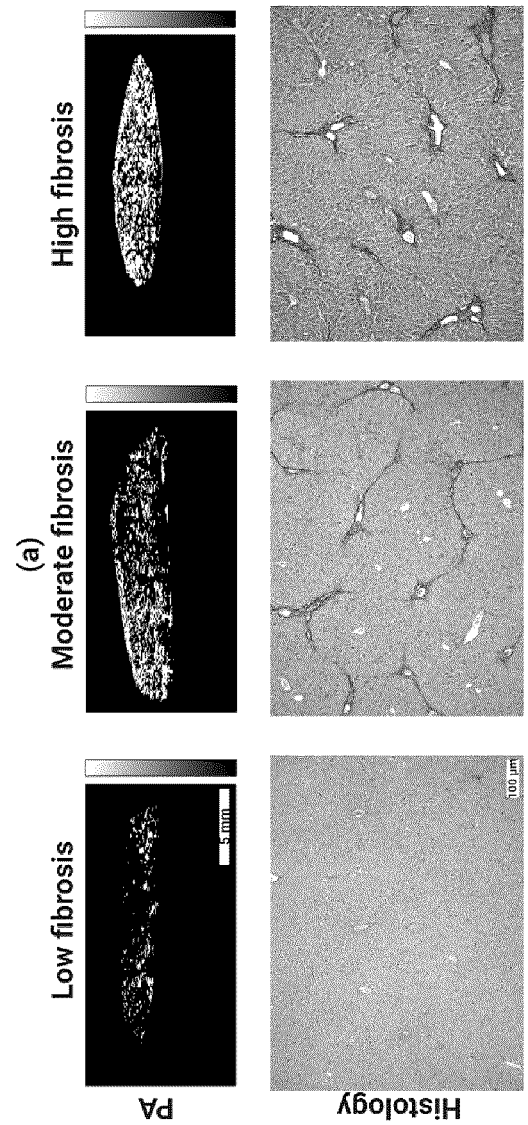
FIG. 12A
FIG. 12B

SEQUENCE LISTING

```
<160> NUMBER OF SEQ ID NOS: 10

<210> SEQ ID NO 1
<211> LENGTH: 17
<212> TYPE: DNA
<213> ORGANISM: Mus musculus

<400> SEQUENCE: 1
gagaaccagc agagcca                                                    17

<210> SEQ ID NO 2
<211> LENGTH: 21
<212> TYPE: DNA
<213> ORGANISM: Mus musculus

<400> SEQUENCE: 2
gaacaaggtg acagaggcat a                                               21

<210> SEQ ID NO 3
<211> LENGTH: 21
<212> TYPE: DNA
<213> ORGANISM: Mus musculus

<400> SEQUENCE: 3
gaaaggatgg agagtcagga a                                               21

<210> SEQ ID NO 4
<211> LENGTH: 19
<212> TYPE: DNA
<213> ORGANISM: Mus musculus

<400> SEQUENCE: 4
cattgcgtcc atcaaagcc                                                  19

<210> SEQ ID NO 5
<211> LENGTH: 21
<212> TYPE: DNA
<213> ORGANISM: Mus musculus

<400> SEQUENCE: 5
```

```
ttctcccttt tgtcccttca c                                              21

<210> SEQ ID NO 6
<211> LENGTH: 18
<212> TYPE: DNA
<213> ORGANISM: Mus musculus

<400> SEQUENCE: 6
gcttctgctg ctcttcgc                                                  18

<210> SEQ ID NO 7
<211> LENGTH: 20
<212> TYPE: DNA
<213> ORGANISM: Mus musculus

<400> SEQUENCE: 7
cactgaaccc taaggccaac                                                20

<210> SEQ ID NO 8
<211> LENGTH: 21
<212> TYPE: DNA
<213> ORGANISM: Mus musculus

<400> SEQUENCE: 8
gagtccagca caataccagt t                                              21

<210> SEQ ID NO 9
<211> LENGTH: 22
<212> TYPE: DNA
<213> ORGANISM: Mus musculus

<400> SEQUENCE: 9
caccatccgg gttcctataa at                                             22

<210> SEQ ID NO 10
<211> LENGTH: 19
<212> TYPE: DNA
<213> ORGANISM: Mus musculus

<400> SEQUENCE: 10
tggcactgca caagaagat                                                 19
```

METHOD AND SYSTEM FOR PHOTOACOUSTIC IMAGING OF TISSUE AND ORGAN FIBROSIS

This application is a 35 USC § 371 national stage entry of International Patent Application No. PCT/CA2020/051791, filed Dec. 23, 2020, entitled "METHOD AND SYSTEM FOR PHOTOACOUSTIC IMAGING OF TISSUE AND ORGAN FIBROSIS", which claims the benefit of U.S. Provisional Patent Application No. 62/953,235, filed Dec. 24, 2019 and the entire contents of each of which are hereby incorporated herein in its entirety.

FIELD

Various embodiments are described herein that generally relate to a method and system for photoacoustic imaging of fibrosis in tissues and organs such as, but not limited to, kidneys, for example.

BACKGROUND

Chronic kidney disease (CKD) is a large and growing health epidemic, with recent estimates suggesting that roughly 10% of the world's population has some form of chronic renal dysfunction. In its advanced stages, CKD is a major cause of morbidity and mortality. Despite decades of research, clinicians still have limited tools at their disposal to prevent disease progression. As such, many patients will progress to kidney failure, a condition that is associated with reduced quality of life, frequent and prolonged hospitalizations, and an increased risk of death [1-2]. Kidney transplantation can restore renal function and thus reduce mortality, improve quality of life, and reduce health care costs [3-5]. However, a dramatic shortage of donor kidneys has meant that patients are often waiting years to receive a kidney [1, 2, 6]. With such a long wait, many patients become too ill to be transplanted or even die on the wait list [7]. To remedy this, kidneys from sicker donors are now frequently used, despite the fact that some are already damaged and will a have shorter lifespan [70, 33].

Fibrosis is a major driver of CKD progression, being a final common pathway of injury that is activated. It is a major cause of renal function loss [10], [32] not only in damaged donor kidneys, but in nearly all forms of CKD [8, 9]. Fibrosis of the renal cortex (i.e. the outer part of the kidney) is of particular importance, as scarring in this area of the kidney can obliterate the glomerular capillaries responsible for blood filtration, and thus impair one of the principal functions of the kidney. Moreover, because the kidney is one of the few tissues in the body with two capillary beds connected in series, fibrotic glomerular capillary loss impairs delivery of oxygen and nutrients to downstream peritubular capillaries, which supply the tubular epithelium of the cortex and the medulla (i.e. the inner part of the kidney) [10]. Thus, fibrosis of the cortex not only reduces kidney function, but it also results in ischemic injury in other areas of the kidney, ultimately causing further renal damage [11]. This makes fibrosis a powerful predictor of long-term kidney outcomes in transplantation and virtually all kidney diseases [8, 9], and is an important disease process being actively targeted by experimental therapies [12].

Unfortunately, no safe and accurate measure of kidney fibrosis exists using conventional techniques. As such, both scientists and clinicians must rely on kidney tissue sampling and subsequent measurement of collagen levels via histologic and/or molecular techniques. Histologic analysis requires invasive tissue sampling. In pre-clinical rodent models, this analysis can only be accomplished after animal sacrifice, whereas in humans, a needle biopsy of the kidney is required. Unfortunately, biopsies are limited by their small sampling size (<1% of one kidney) leading to sampling bias, and by significant bleeding risks induced by the biopsy procedure [13, 14]. In the setting of kidney transplantation, these limitations mean that a biopsy is either not performed, or even if it is, quantification of fibrosis may not be reflective of overall renal scar burden [15]. Thus, clinicians must currently rely on non-invasive surrogate measures of chronic kidney damage that, while somewhat informative, are limited in utility. As such, physicians must ultimately make decisions regarding acceptance of a kidney and matching to a recipient based on incomplete and possibly incorrect information.

Imaging techniques have revolutionized the ability to non-invasively examine tissues. Unfortunately, no standard technology (conventional ultrasound, CT or MRI) can reliably quantify renal fibrosis [16]. The addition of fibrosis-targeted contrast agents to augment standard imaging technologies has recently been described, but currently their use has been limited by the toxicity and pharmacokinetics of these agents [71].

SUMMARY OF VARIOUS EMBODIMENTS

In one broad aspect, at least one embodiment is provided herein for an imaging system for performing collagen assessment of an object using Photoacoustic Image (PA) data obtained for the object, wherein the system comprises: a data store comprising program instructions for performing collagen assessment for the object; and a processing unit that is coupled to the data store, the processing unit, when executing the program instructions, being configured to: obtain beamformed PA image data for the object using at least three wavelengths related to chromophores including collagen, oxyhemoglobin and deoxyhemoglobin, the three wavelengths being less than 1000 nm; perform spectral decomposition on the beamformed PA image data using the at least three wavelengths to obtain data that is used for generating at least one collagen map; and determine a collagen score for the at least one collagen map.

In at least one embodiment, the processing unit is configured to use the data obtained from the spectral decomposition for generating at least one oxyhemoglobin map and at least one deoxyhemoglobin map.

In at least one embodiment, the processing unit is further configured to compare the collagen score with a collagen threshold to assess an amount of collagen in the object.

In at least one embodiment, the at least three wavelengths are in the range of about 680 to 930 nm.

In at least one embodiment, the at least three wavelengths are within about 10% to 20% of 680 nm, 725 nm and 755 nm.

In at least one embodiment, the at least three wavelengths are about 680 nm, 725 nm and 755 nm.

In at least one embodiment, the collagen score is determined for a given collagen map by determining a mean pixel value, a median pixel value or a mode pixel value from the collagen map.

In at least one embodiment, there are a plurality of collagen maps each having a collagen score to provide a plurality of collagen scores and an overall collagen score is obtained by determining a mean, a median or a mode from the plurality of collagen scores.

In at least one embodiment, the beamformed PA image data are obtained from the data store.

In at least one embodiment, the system further comprises a probe for performing 2D PA imaging, wherein the probe includes: a light source that is configured to generate a plurality of light stimulus signals for illuminating a portion of the object, a first portion of the light stimulus signals having a first wavelength of the three wavelengths, a second portion of the light stimulus signals having a second wavelength of the three wavelengths and a third portion of the light stimulus signals having a third wavelength of the three wavelengths; a transducer for sensing RF acoustic response signals that are generated by the portion of the object in response to the light stimulus signals; and an aperture at a distal portion of the probe through which the light stimulus signals are outputted to illuminate the portion of the object and through which the RF acoustic response signals are received for sensing by the transducer.

In at least one embodiment, the probe further comprises: a moveable mount that is affixed to a moveable portion of the probe for moving the aperture of the probe during PA imaging; and a motor that is operably connected to the moveable mount to move the moveable mount so that the aperture moves according to a scan trajectory during PA imaging of the object.

In at least one embodiment, the object is a tumour or tissue, or an organ including liver, intestines, heart, lung, skin, muscles, eyes, or pancreas.

In at least one embodiment, the object is a kidney and during 2D PA imaging, the aperture of the probe is positioned to obtain PA image data for a transverse slice through a longest point of the kidney.

In at least one embodiment, the object is a kidney and during 3D PA imaging, the aperture of the probe is moved to a plurality of positions separated by a predetermined interval across the entire kidney to obtain 2D PA image data at each position to capture intra-kidney variation in collagen content.

In at least one embodiment, the predetermined interval is between about 50 to 300 μm, and is more preferably about 150 μm.

In at least one embodiment, the system further comprises: an analog to digital converter for converting the sensed RF acoustic response signals into digitized RF acoustic response signals, and the processing unit is configured to perform beamforming and noise reduction on the digitized RF acoustic response signals to generate the beamformed PA image data.

In at least one embodiment, the spectral decomposition comprises spectral unmixing.

In at least one embodiment, the processing unit is further configured to perform: (a) displaying the at least one collagen map on a display, (b) electronically transmitting the collagen map to another device, (c) storing the at least one collagen map in a data store or any combination of (a), (b) and (c).

In another broad aspect, in accordance with the teachings herein, there is provided a method of performing collagen assessment of an object using Photoacoustic Image (PA) data obtained for the object, wherein the method is performed by a processing unit and the method comprises: obtaining beamformed PA image data for the object using at least three wavelengths related to chromophores including collagen, oxyhemoglobin and deoxyhemoglobin, the three wavelengths being less than 1000 nm; performing spectral decomposition on the beamformed PA image data using the three wavelengths to obtain data that is used for generating at least one collagen map; and determining a collagen score for the at least one collagen map.

In at least one embodiment, the method further comprises using the data obtained from the spectral decomposition for generating at least one oxyhemoglobin map and at least one deoxyhemoglobin map.

In at least one embodiment, the method further comprises comparing the collagen score with a collagen threshold to assess an amount of collagen in the object.

In at least one embodiment, the method comprises determining the collagen score for a given collagen map by determining a mean pixel value, a median pixel value or a mode pixel value from the collagen map.

In at least one embodiment, there are a plurality of collagen maps each having a collagen score to provide a plurality of collagen scores and the method comprises obtaining an overall collagen score by determining a mean, a median or a mode from the plurality of collagen scores.

In at least one embodiment, the method comprises obtaining the beamformed PA image data from the data store.

In at least one embodiment, the method comprises: generating a plurality of light stimulus signals using a light source to illuminate a portion of the object by transmitting the plurality of light signals through an aperture, the plurality of light stimulus signals including a first portion having a first wavelength of the three wavelengths, a second portion having a second wavelength of the three wavelengths and a third portion having a third wavelength of the three wavelengths; and sensing, through the aperture using a transducer, RF acoustic response signals that are generated by the portion of the object in response to the light stimulus signals.

In at least one embodiment, the method comprises moving the aperture of the probe according to a scan trajectory during PA imaging.

In at least one embodiment, the object is tumour, tissue or an organ including liver, intestines, heart, lung, skin, muscles, pancreas, or eyes.

In at least one embodiment, the object is a kidney and the method comprises storing the kidney in a solution during PA imaging.

In at least one embodiment, the solution has a temperature of about 4 to 10 degrees Celsius.

In at least one embodiment, the solution comprises saline, UW solution, HTK solution, Collins solution, Celsior solution, Kyto University solution, or IGL-1 solution.

In at least one embodiment, during 2D PA imaging the method comprises positioning the aperture of the probe to obtain PA image data for a transverse slice through a longest point of the kidney.

In at least one embodiment, during 3D PA imaging the method comprises moving the aperture of the probe to a plurality of positions separated by a predetermined interval across the entire kidney to obtain 2D PA image data at each position to capture intra-kidney variation in collagen content.

In at least one embodiment, the predetermined interval is between about 50 to 300 μm, and is more preferably about 150 μm.

In at least one embodiment, the method further comprises: converting, with an analog to digital converter, the sensed RF acoustic response signals into digitized RF acoustic response signals, and performing beamforming and noise reduction on the digitized RF acoustic response signals to generate the beamformed PA image data.

In at least one embodiment, the method comprising performing spectral decomposition by using spectral unmixing.

In at least one embodiment, the method further comprises performing: (a) displaying the at least one collagen map on a display, (b) electronically transmitting the collagen map to another device, (c) storing the at least one collagen map in a data store or any combination of (a), (b) and (c).

In at least one embodiment, the object is a kidney and when comparison of the collagen score with the collagen threshold indicates that the kidney is suitable for transplant for a recipient patient, the method further comprises performing transplanting the kidney into the recipient patient.

In another broad aspect, in accordance with the teachings herein, there is provided a method for performing a transplant of an organ, wherein the method comprises: performing collagen assessment of the organ using a Photoacoustic Imaging (PA) based method that is defined in accordance with the teachings herein to obtain a collagen score; comparing the collagen score with a collagen threshold to determine if the organ is suitable for transplant for a recipient patient; and transplanting the organ into the recipient patient when the comparison indicates that the organ is suitable for transplant for the recipient patient.

In another broad aspect, in accordance with the teachings herein, there is provided a use of a method of performing collagen assessment of an organ using Photoacoustic Image (PA) data to determine whether the organ is suitable for transplant in a recipient patient, wherein the method is defined in accordance with the teachings herein.

In another broad aspect, in accordance with the teachings herein, there is provided a non-transitory computer readable medium storing program instructions that when executed by a processor, configure the processor to perform a method of performing collagen assessment of an object using Photoacoustic Image (PA) data obtained for the object, wherein the method is defined according to any one of the embodiments described herein.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

FIG. 2B is a flow chart diagram showing an example embodiment of a PA imaging method in accordance with the teachings herein.

FIG. 2C shows an example of the spatial positions of a set of RadioFrequency (RF) acoustic response signals acquired with a given light stimulus $L_{ik}$ at a given wavelength $\lambda_i$.

FIG. 2D shows an example of the spatial and temporal positions for a plurality of sets of RF acoustic response signals acquired with sequential light stimuli $L_1$ to $L_P$ each at the given wavelength.

FIG. 3A shows a schematic of the experimental setup for validating use of PA with spectral unmixing for identifying collagen using blood-collagen phantom gels.

FIG. 3B shows representative co-registered ultrasound (US) and PA images of a blood-collagen phantom.

FIG. 3C shows the correlation between actual collagen content and estimated collagen content from PA imaging for several phantoms.

FIG. 4A shows the experimental setup for validating use of PA with spectral unmixing for identifying collagen using kidney biopsy samples and whole kidneys.

FIG. 4B shows a conceptual image for the acquisition of data for 2D and 3D PA imaging in accordance with the teachings herein.

FIGS. 8A-8G show the experimental setup and results that demonstrate how PA imaging can detect intra-kidney variations in collagen content in human kidneys.

FIG. 11 shows a schematic for performing a liver fibrosis study in mice.

FIG. 12A shows representative PA and histology collagen maps for mice with three different degrees of liver fibrosis (the scale bars apply to all corresponding PA and histology images).

FIG. 12B show a plot of the correlation between the PA estimates of collagen and histological estimates for n=12 mice for the low fibrosis group, n=16 for the moderate fibrosis group and n=15 for the high fibrosis group.

Figure 1A:
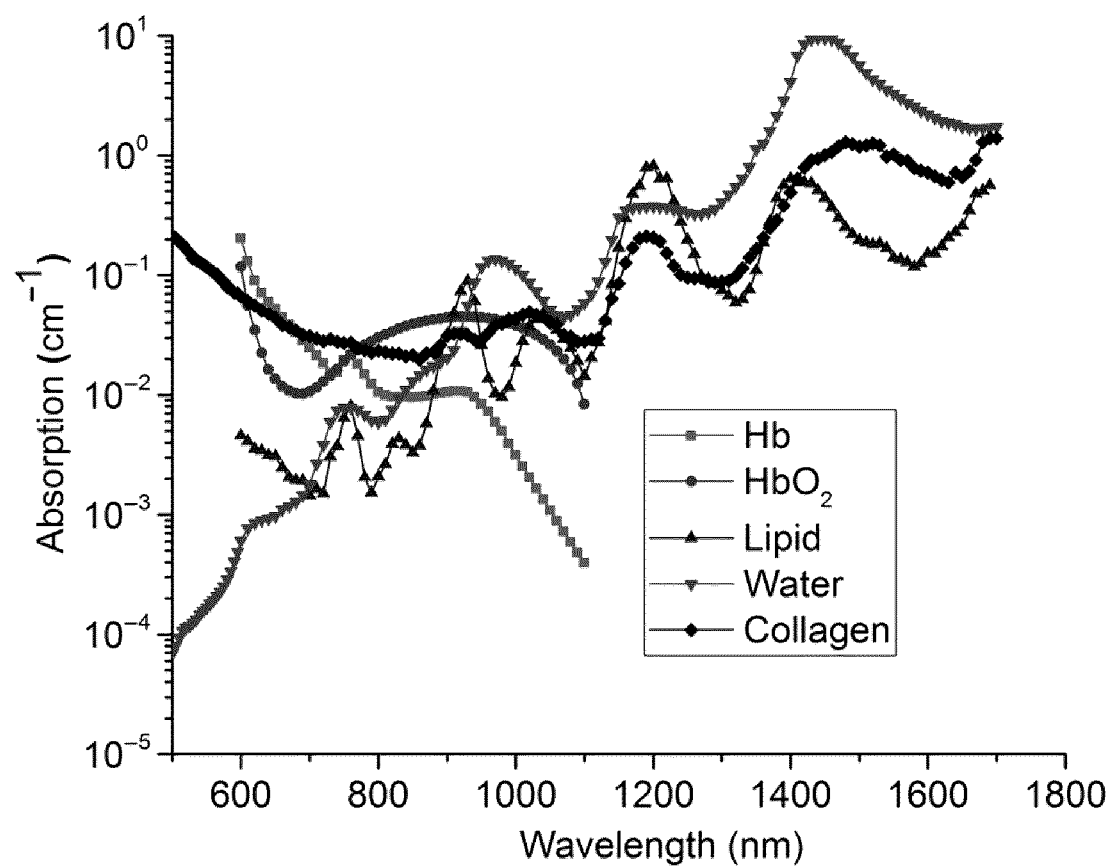
FIG. 1A shows the absorption spectrum for several chromophores that can be encountered in PA imaging of a kidney.

Further aspects and features of the example embodiments described herein will appear from the following description taken together with the accompanying drawings.

DETAILED DESCRIPTION OF THE EMBODIMENTS

Various embodiments in accordance with the teachings herein will be described below to provide an example of at least one embodiment of the claimed subject matter. No embodiment described herein limits any claimed subject matter. The claimed subject matter is not limited to devices, systems or methods having all of the features of any one of the devices, systems or methods described below or to features common to some or all of the devices and or methods described herein. It is possible that there may be a device or method described herein that is not an embodiment of any claimed subject matter. Any subject matter that is described herein that is not claimed in this document may be the subject matter of another protective instrument, for example, a continuing patent application, and the applicants, inventors or owners do not intend to abandon, disclaim or dedicate to the public any such subject matter by its disclosure in this document.

It will be appreciated that for simplicity and clarity of illustration, where considered appropriate, reference numerals may be repeated in the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should also be noted that the terms "coupled" or "coupling" as used herein can have several different meanings depending in the context in which these terms are used. For example, the terms coupled or coupling can have a mechanical, optical, acoustic or electrical connotation. For example, as used herein, the terms coupled or coupling can indicate that two elements or devices can be directly connected to one another or connected to one another through one or more intermediate elements or devices via an electrical or optical signal or a mechanical element, depending on the particular context. Acoustic coupling is meant to cover the propagation of acoustic waves from tissue that generated the acoustic waves through a coupling medium, such as water, to an acoustic sensor.

It should also be noted that, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that terms of degree such as "substantially", "about" and "approximately" as used herein mean a reasonable amount of deviation of the modified term such that the end result is not significantly changed. These terms of degree may also be construed as including a deviation of the modified term, such as by 1%, 2%, 5% or 10%, for example, if this deviation does not negate the meaning of the term it modifies.

Furthermore, the recitation of numerical ranges by endpoints herein include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed, such as 1%, 2%, 5%, or 10%, for example.

The example embodiments of the devices, systems or methods described in accordance with the teachings herein may be implemented as a combination of hardware and software. For example, the embodiments described herein may be implemented, at least in part, by using one or more computer programs, executing on one or more programmable devices comprising at least one processing element and at least one storage element (i.e. at least one volatile memory element and at least one non-volatile memory element). The hardware may comprise input devices including at least one of a touch screen, a keyboard, a mouse, buttons, keys, sliders and the like, as well as one or more of a display, a speaker, a printer, and the like depending on the implementation of the hardware.

It should also be noted that there may be some elements that are used to implement at least part of the embodiments described herein that may be implemented via software that is written in a high-level procedural language such as object oriented programming. The program code may be written in MATLAB, Julia, Python, C, C++ or any other suitable programming language and may comprise modules or classes, as is known to those skilled in object oriented programming. Alternatively, or in addition thereto, some of these elements implemented via software may be written in assembly language, machine language or firmware as needed. In either case, the language may be a compiled or interpreted language.

At least some of these software programs may be stored on a computer readable medium such as, but not limited to, a ROM, a magnetic disk, an optical disc, a USB key and the like that is readable by a device having a processor, an operating system and the associated hardware and software that is necessary to implement the functionality of at least one of the embodiments described herein. The software program code, when read by the device, configures the device to operate in a new, specific and predefined manner in order to perform at least one of the methods described herein.

Furthermore, at least some of the programs associated with the devices, systems and methods of the embodiments described herein may be capable of being distributed in a computer program product comprising a computer readable medium that bears computer usable instructions, such as program code, for one or more processing units. The medium may be provided in various forms, including non-transitory forms such as, but not limited to, one or more diskettes, compact disks, tapes, chips, and magnetic and electronic storage. In alternative embodiments, the medium may be transitory in nature such as, but not limited to, wire-line transmissions, satellite transmissions, internet transmissions (e.g. downloads), media, digital and analog signals, and the like. The computer useable instructions may also be in various formats, including compiled and non-compiled code.

Although kidney transplantation has revolutionized the care of patients with kidney failure, clinicians currently only have limited ways of assessing donor kidney quality. As such, optimal matching of donor kidneys to recipients cannot be performed, meaning that some patients receive damaged kidneys that function suboptimally, and that fail prematurely. Kidney fibrosis (the root cause of kidney scarring) may also be present in donor kidneys, and in nearly all forms of CKD. Fibrosis is not just a marker of chronic damage, but also can drive ongoing disease progression. Accordingly, when these kidneys are transplanted, they often last for a short period, forcing patients back on the long transplant list for another kidney. However, currently there is no safe, easy was to quantify renal fibrotic burden, let alone a reliable non-invasive tool for assessing the quality of the donated kidneys before transplantation.

Therefore, assessment of donor kidney quality is an important initial step in the transplant process. When first notified of a potential kidney donor, clinicians assess whether a kidney is useable for transplant, and then next decide which recipient the kidney should be matched to. Given the dramatic shortage of available donor kidneys, the ultimate goal of the transplant process is to match each kidney to the most appropriate patient, to maximize the benefit for all recipients. Thus, the least damaged kidneys ideally should be transplanted into younger recipients who require the longest lasting kidneys. In contrast, kidneys with some pre-existing damage are better matched to older recipients, so as to avoid longer wait times for less damaged kidneys that have expected lifespans longer than those of the patients themselves [33]—[35].

Current clinical tools attempt to measure chronic donor kidney damage processes such as fibrosis. The most widely used system divides donor kidneys into "standard criteria donor" (SCD) or "expanded criteria donor" (ECD) kidneys, based on donor age, renal function, and history of hypertension [72]. While easy to use and broadly predictive of outcome, this binary system does not fully assess donor kidney quality, as many ECD kidneys have better outcomes than some of their SCD counterparts [33]. Moreover, while comprehensive clinical tools have subsequently been developed, they unfortunately still rely on non-specific, non-invasive clinical variables that ultimately do not provide tissue-level detail [38], [39]. In contrast, kidney biopsy enables detailed histologic assessment, but is limited by significant bleeding risk, the potential for sampling bias, the time required for proper staining, and the requirement for 24 hour renal pathology expertise [13]. These limitations have rendered biopsy analysis impractical and potentially inaccurate as a means of assessing donor kidney fibrosis.

Recently, however, the novel combination of ultrasound ("acoustic") with laser technology ("photo") has enabled contrast-free imaging of specific tissue components by taking advantage of their unique light absorption properties [65]-[67]. PA imaging involves the irradiation of tissues with short pulses of laser light. In response to the light stimulation, absorbers or chromophores in a sample, such as a tissue sample, will rapidly expand to create a pressure rise and gradually contract due to heat dissipation. The process is referred to as thermoelastic expansion, with an initial pressure rise ($p_o$) expressed as:

$$p_o(r')=\Gamma H(r',t') \quad (1)$$

where r' is the location of the absorbers, $\Gamma$ is Gruneisen parameter and H is the deposited thermal energy. The Grüneisen parameter may have a relatively small spatial fluctuation for a fixed temperature. Therefore, the Gruneisen parameter is usually assumed to be constant as the spatial fluctuations are insignificant [68]. The thermal energy deposited is the energy deposited per unit volume and per unit time and it is expressed as:

$$H(r',t')=\phi(r',t')\mu_a(r') \quad (2)$$

where $\phi$ is the light fluence and $\mu_a$ is the optical absorption coefficient. The pressure rise will generate ultrasound pulses or pressure waves that propagate according to the PA wave equation [69].

The generated PA signals can be detected using an ultrasound transducer (i.e. an array of ultrasound sensors). Since the generated PA signals are acoustic signals with frequencies in the RF bandwidth, they may also be referred to herein as PA RF signals or RF acoustic response signals.

In PA imaging, endogenous molecules such as melanin, hemoglobin, bilirubin and lipids have unique light absorption spectra, enabling high resolution imaging of their spatial distribution by tuning the wavelength of laser illumination [20]-[22]. Kidneys, like all biological tissues, are composed of a complex mixture of molecules. Each molecule has its own light absorption properties, and thus can act as a chromophore when illuminated by light of specific wavelengths [23]. Light absorption during PA imaging results in thermoelastic expansion, such that a brief illumination pulse can lead to an expansion-contraction sequence that generates an acoustic wave that can be detected by an ultrasound transducer. Thus, if a molecule is present in sufficient concentration, this pattern of light absorption can be used as a "molecular fingerprint" to estimate its amount and distribution within tissue using PA imaging [17].

Since certain endogenous molecules have unique light absorption spectra, their spatial distribution may be determined by using PA imaging. Referring now to FIG. 1A, shown therein is an example of an absorption spectrum for several chromophores that can be encountered in PA imaging of a kidney. As can be seen, collagen (the main protein present in scarring) is one of many abundant optical tissue chromophores and each of these chromophores have a unique optical absorption spectrum. Due to a lack of spectral features (e.g. peaks and valleys), researchers have historically ignored the 680-900 nm optical wavelength range, opting to study collagen at the longer wavelengths (>1000 nm) where spectral features are available. However, there are limited clinical applications at these wavelength ranges, particularly for imaging transplanted kidneys and other biologic tissues.

Historically PA imaging studies have focused on the quantification of hemoglobin in tissues given its strong absorption properties and abundance [29]. Recent studies have been done to explore whether collagen, the main component of scar tissue, can be imaged using photoacoustics. To date, these studies have demonstrated that, in small animal pre-clinical models, PA may be able to image fibrosis in liver [45], intestine [46, 47] and skeletal muscle [73]. Most of these studies utilized light with wavelengths greater than 1000 nm, taking advantage of the increased light absorption properties of collagen in this spectral range to enable stronger collagen-derived PA signal generation [19]. Unfortunately, water also strongly absorbs light at these same wavelengths, limiting the penetration depth and the practical utility of this imaging technique, given the high-water content within tissue and the common use of water-based gels as ultrasound transducer coupling agents. Secondly, while some of these studies imaged fibrosis within large tissue regions, this provided an overall measure of fibrotic burden but did not demonstrate the ability to accurately quantify intra-tissue variations in collagen content. Thirdly, to date these studies have been performed only in small animal models [47], meaning that the ability to image collagen in much larger human organs, and thus the potential clinical utility of fibrosis PA imaging, has remained unclear.

However, the inventors have developed a PA imaging technique using sub 1000 nm light illumination that estimates collagen concentration with negligible interference from water molecules and with exquisite accuracy as well as providing sufficiently high resolution to accurately capture intra-renal variations in collagen content, suggesting the potential to image not only differences in collagen amount, but also collagen distribution. Furthermore, the inventors have discovered that spectral unmixing of PA response data that was obtained using illumination stimuli having just a few stimulus wavelengths in a lower portion of the wavelength range below 1000 nm can be used to accurately estimate collagen concentration in kidneys, without the need for exogenous contrast agents. Unlike other imaging modalities that can be used to assess fibrosis (e.g. ultrasound, MRI, and CT), the inventors have found that performing PA imaging in this way offers molecular sensitivity to collagen, which is the core component of fibrosis, that is not possible with the other imaging modalities. This is because ultrasound, MRI and CT cannot measure collagen directly, nor do these imaging modalities have the molecular specificity that PA imaging has. Furthermore, while ultrasound, MRI and CT may measure some clinical markers that might be related to fibrosis (i.e. stiffness), these imaging modalities are also affected by other aspects of kidney diseases that have nothing to do with fibrosis which may affect measurement results.

Figure 1B:
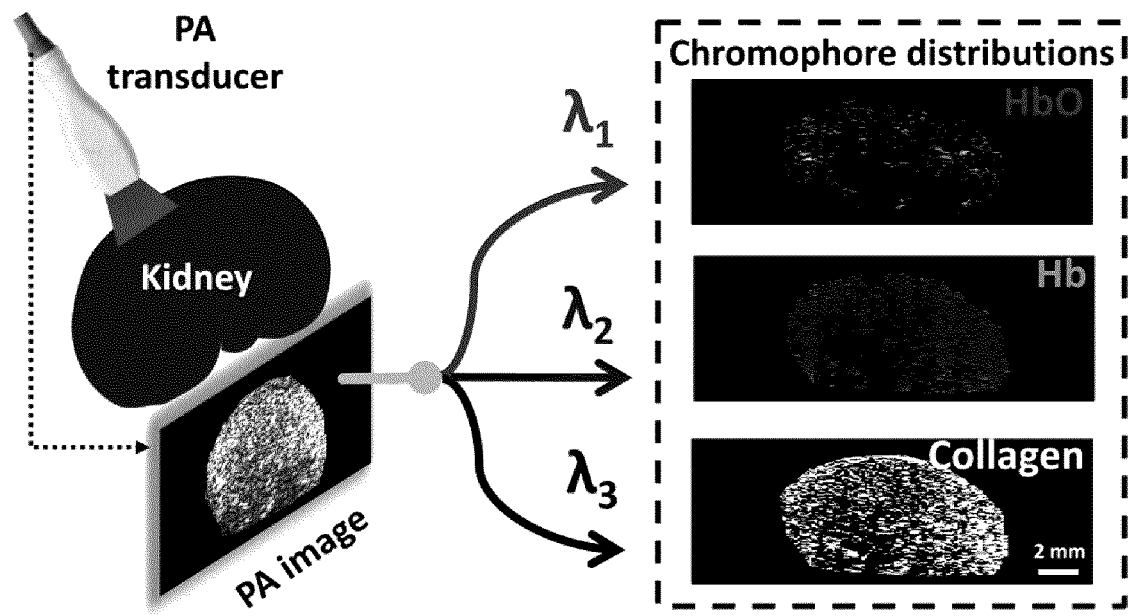
FIG. 1B is a schematic providing an overview of PA imaging as a tool to non-invasively quantify collagen content.

For example, referring now to FIG. 1B, shown therein is a schematic providing an overview of using PA imaging as a tool to non-invasively quantify collagen content. PA images may be acquired at multiple wavelengths (A) and are input into a spectral unmixing algorithm, which can separate out individual contributions of certain chromophores such as oxyhemoglobin (HbO), deoxyhemoglobin (Hb), and collagen. Portions of the spectral unmixed PA data may then be used to generate at least one PA chromophore map which provides the spatial distribution and estimates of at least one chromophore content such as collagen content, and optionally oxygenated and deoxygenated hemoglobin content, within the imaged kidney.

The PA imaging techniques described herein were used to quantify whole kidney fibrotic burden in mice, and also renal cortex fibrotic burden in pig and human kidneys, with speed (<1.5-minute scan time) and remarkable accuracy. In fact, using ex vivo collagen phantom gels, as well as kidneys from mice, pigs, and humans, it is demonstrated herein that PA collagen imaging demonstrates an exquisite ability to quantify fibrotic burden, when compared to gold standard measures.

In another aspect, the PA imaging techniques described herein may be performed in a setting that mimics human intraoperative kidney transplantation, which may aid in rapid translation thereby addressing a vexing clinical problem. The PA collagen imaging techniques described herein can therefore be used for non-invasive fibrosis quantification that may have widespread pre-clinical and clinical impact. For example, the PA imaging techniques of the teachings herein can be used to non-invasively assess the quality of kidney transplant donations and ensure that physicians can better allocate the preciously scarce kidneys that are available for transplantation. The societal value of the transplant increases accordingly so that a kidney that is identified with minimal collagen, and therefore with minimal scarring, may be provided to a younger patient who will utilize the kidney for decades, while a kidney that is identified as containing some collagen, and therefore has some fibrosis, may be more suitable for an older recipient who might only require the kidney for a few years.

Similarly, as nearly all chronic diseases lead to fibrosis, the PA imaging techniques and collagen assessment of the teachings herein may be used to non-invasively assess fibrotic burden in many other organs, including but not limited to the liver, intestines, heart, skin, and muscles, which are all organs that exhibit fibrosis. It can also be used to monitor radiation-induced fibrosis (or radiation fibrosis syndrome (RFS)), which is a long-term side effect of external beam radiation therapy for the treatment of cancer characterized by increased collagen deposition, poor vascularity, and scarring in exposed tissues. Similarly, it can also be used to monitor cancer-associated fibrosis, a type of scarring that occurs in response to tumour formation and growth.

Figure 2A:
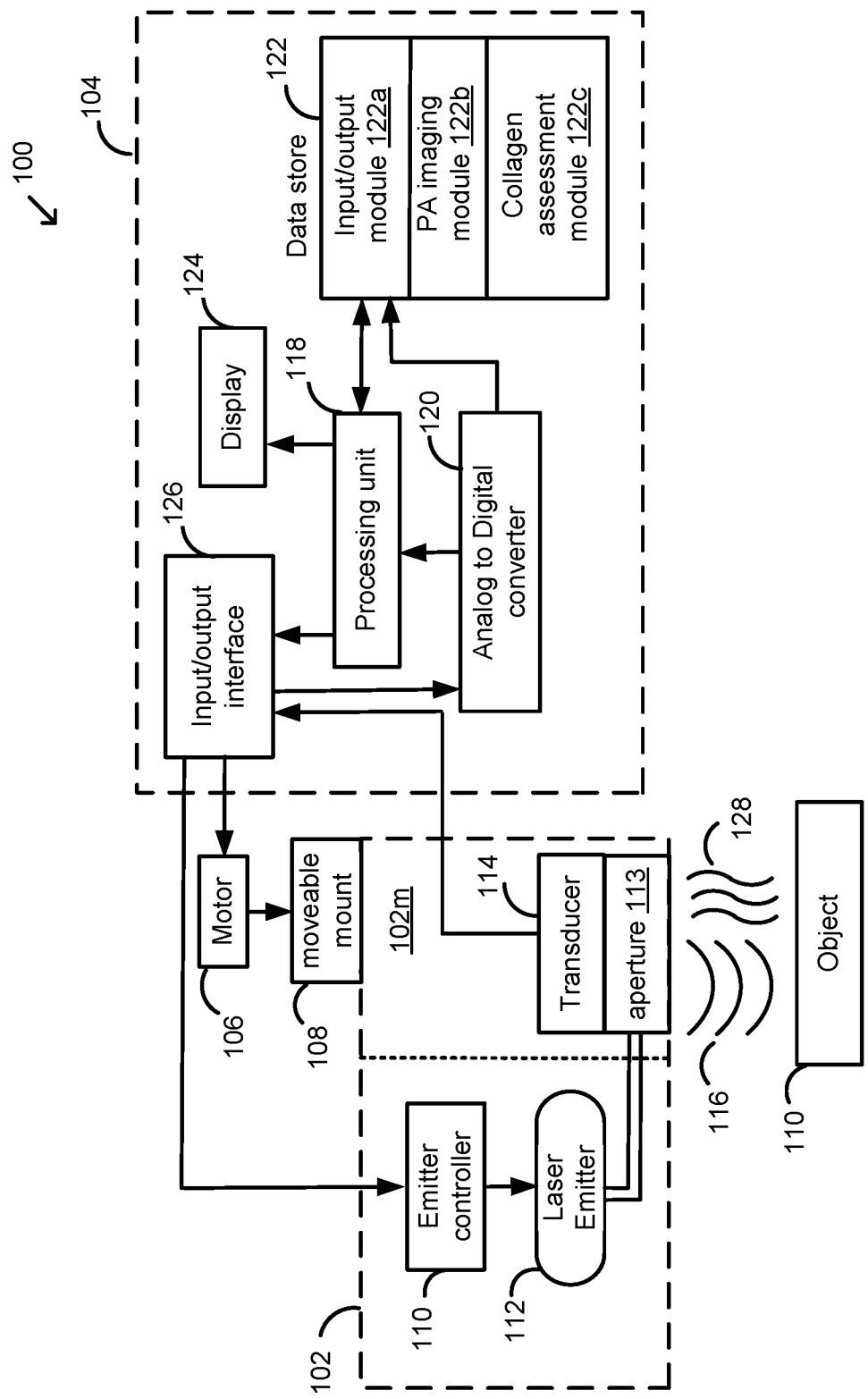
FIG. 2A is a block diagram of an example embodiment of a PA imaging system in accordance with the teachings herein.

Referring now to FIG. 2A, shown therein is a block diagram of an example embodiment of a PA imaging system 100 that can be used to non-invasively directly determine collagen content in kidneys in accordance with the teachings herein. The PA imaging system 100 comprises a probe 102, an imaging unit 104, a motor 106 and a moveable mount 108 for the probe. The PA imaging system 100 is used to generate PA images of an object 110. The object 110 is imaged as it requires analysis and the object may be a phantom, such as a gelatin vessel phantom, or a biological sample or organ, such as a kidney, for example. The object 110 may be an in vivo organ or other biological matter such as a tumour.

The probe 102 comprises an emitter controller 110, a laser emitter 112 and a transducer 114. A moveable portion of the probe 102m is mounted or fixed to the moveable mount 108. The motor 106 is mechanically coupled to the moveable mount 108 to move the position of the aperture along with the transducer 114 for receiving RF acoustic response signals when performing 2D and/or 3D PA imaging on different portions of the object 110 according to a scan trajectory. It should be noted that while the laser emitter 112 and the transducer 114 are shown beside one another this is done for ease of illustration since in actual implementations the laser emitter 112 and the transducer 114 may use the same aperture for transmitting and receiving signals, respectively.

The motor 106 may be a stepper motor with high precision to provide scanning at cm, mm or micron step sizes. The moveable mount 108 includes a translatable component, such as a platform connected to a pulley or a belt which is driven by the motor 106, as is known by those skilled in the art. In alternative embodiments, other physical arrangements are possible that provide the same functionality. It should be noted that in other embodiments the moveable mount 108 may also include components for providing rotational motion in which case a different type of image reconstruction that takes this rotational movement into account is used.

The emitter controller 110 is operably coupled to the laser emitter 112 to control the laser emitter 112 to generate light excitation signals 116 (also known as light stimulus signals or illumination signals) at desired wavelengths for illuminating the portion of the object 110 to be imaged. In some embodiments, the emitter controller 110 may be operatively coupled to the imaging unit 104 for receiving control signals therefrom. In some embodiments, the probe 102 may be modified to work with other types of light generators such as, but not limited to, an LED laser source, for example. The emitter controller 110 may be implemented by using a processor along with suitable hardware or by using a commercial controller. In some embodiments, there may be an optical cable or other suitable light conduit from the laser emitter 112 to a front portion of the probe 102 and during use the light stimulus signal is generated, propagates along the light conduit and exits via the front portion (e.g. aperture) of the probe 102.

The imaging unit 104 comprises a processing unit 118, an Analog to Digital Converter (ADC) 120, a data store 122, a display 124 and an input/output interface 126 which may be coupled to various peripheral components (not shown). In some embodiments, the processing unit 118 may also provide the functionality of the emitter controller 110. The imaging unit 104 may also include a power unit (not shown) or be connected to a power source to receive power needed to operate its components. It should be noted that the components shown in FIG. 2A are provided as an example and there may be more or less components or alternative layouts in other embodiments.

The processing unit 118 is operatively coupled to the other components of the imaging unit 104 for controlling various operations of the imaging unit 104, such as setting or modifying stimulus parameters (i.e. wavelength and intensity), the data acquisition process (i.e. controlling sampling rates, physical sampling trajectories, etc.), the energy normalization for the laser emitter 112 and the operation for collagen identification and assessing kidneys for transplant, as well as assessing collagen in other organs or tissues as previously described.

The processing unit 118 can be any suitable processor, controller or digital signal processor that can provide sufficient processing power depending on the operational requirements of the imaging unit 104 as is known by those skilled in the art. For example, the processing unit 118 may be a high performance general processor. In alternative embodiments, the processing unit 118 may include more than one processor with each processor being configured to perform different dedicated tasks. In alternative embodiments, specialized hardware can be used to provide some of the functions provided by the processing unit 118, such as at least one Application Specific Integrated Circuit (ASIC) and/or a Field Programmable Gate Array (FPGA), for example.

The data store 122 includes volatile and non-volatile memory elements such as, but not limited to, one or more of RAM, ROM, one or more hard drives, one or more flash drives or some other suitable data storage elements. The data store 122 may be used to store an operating system and programs as is commonly known by those skilled in the art. For instance, the operating system provides various basic operational processes for the processing unit 118 and the programs include various operational and user programs so that a user can interact with the processing unit 118 to configure and control the operation of the imaging unit 104.

The data store 122 may also include software code for implementing various components for collagen identification, kidney transplant assessment or assessment of other organs in accordance with the teachings herein as well as values of various operational parameters that are used for PA imaging. For example, the data store 122 can include programs for implementing an input/output module 122a, a PA imaging module 122b, and a collagen assessment module 122c.

The input/output module 122a can include program instructions for receiving acquired PA data and user control data. The input/output module 122a can also include program instructions for outputting and/or storing raw PA data, PA images, collagen assessment data, and various maps that may be generated for one or more chromophores in the portion of the object 110 being imaged.

The PA imaging module 122b can include program instructions for generating the light stimulus signals and acquiring the RF acoustic response signals. For example, the PA imaging module 122b can generally include program instructions for: (a) setting certain parameters of the light stimulus signals including wavelength content and intensity; (b) defining scan trajectories for illuminating a portion of the object 110 via the laser emitter 112 for imaging and receiving the RF acoustic response signals via the transducer 114; (c) applying the light stimuli to the portion of the object 110 to be imaged according to the scan trajectories; (d) performing preprocessing of the digitized RF acoustic response signals; and (e) generating PA image data. These functions are described in more detail with respect to acts 204 to 212 of the PA imaging method 200 shown in FIG. 2B.

When the object 100 is a kidney, the collagen assessment module 122c can include program instructions for determining the collagen content from the PA image data and assessing the kidney for transplant. For example, the kidney assessment module 122c generally includes program instructions for: (a) performing spectral decomposition on the PA image data; (b) determining collagen content of the portion of the object 110 being imaged from processing the spectral decomposed PA image data; (c) performing kidney assessment based on the collagen content; and (d) generating one or more maps of one or more constituents of the portion of the object being imaged, such as a collagen map and optionally, an oxyhemoglobin/deoxyhemoglobin map. It should be noted that in other embodiments, other organs or tissue may be assessed and the collagen assessment module 122c may be referred to as a kidney assessment module 122c, a sample assessment module 122c or an organ/tissue assessment module 122c. Other examples of organs or tissue that may be assessed include the liver, the lung, cancerous tumours, skin, muscle, intestines, the pancreas, the eye and the heart, for example.

The data store 122 can also be used to store the RF acoustic response signals that are acquired, various processed forms of these signals and any images that are generated therefrom such as, but not limited to, PA images, collagen maps and/or oxygenation maps, for example. The data store 122 may also include one or more databases for storing information about the kidneys, or other objects that are being assessed.

The display 124 can be any suitable device for displaying images and various types of information such as an LCD monitor or touchscreen display. The input/output interface 126 can be various ports such as one of more of USB, Firewire, serial and parallel ports, for example, that may be coupled with various peripheral devices used for the input or output of data. Examples of these devices include, but are not limited to, at least one of a keyboard, a mouse, a trackpad, a touch interface, and a printer.

In use, the laser emitter 112 is controlled to generate light signals 116 for illuminating one or more portions of the object 110 for PA imaging. The laser emitter 112 is just one example of a light source which is used to generate the light stimulus signals and other types of light sources may be used in other embodiments such as, but not limited to, light emitting diodes (LEDs), for example. A plurality of light signals 116 are generated in which each light signal has a predetermined waveform with at least one of three predetermined wavelengths for a predetermined period of time for eliciting RF acoustic response signals 128 from the portion of the object 110 being imaged that are generated due to the thermoelastic expansion process explained previously. For performing PA imaging to generate a given 2D PA image or to generate a given 2D PA image which is part of a series of 2D PA images that are generated with 3D PA imaging, the light signals 116 may include a first group of light signals having a first wavelength, a second group of light signals having a second wavelength and a third group of light signals having a third wavelength, where the three wavelengths are selected as described below.

The RF acoustic response signals 128 are sensed by the transducer 114 which is an ultrasonic transducer having an array of ultrasound sensors, as is known by those skilled in the art. For example, the transducer 114 can be a linear array transducer. In some embodiments, the transducer 114 may be a phased array transducer. The RF acoustic response signals 128 have informative frequency content in the RF range. Accordingly, the transducer 114 is designed with a frequency response bandwidth in the RF range so that it can sense the RF acoustic response signals that are generated by the object 110 when it is illuminated with light stimuli 116.

During data acquisition, the RF acoustic response signals 128 that are sensed by the transducer 104 are converted to digital signals by the ADC 120. The RF acoustic response signals can then be stored in the data store 122 for later processing or can be sent to the processing unit 114 which processes the digitized RF acoustic response signals 128 to determine collagen content in the portion of the object 110 being imaged and may optionally be used to generate and display a property map of a certain constituent of the portion of the object 110 being imaged, such as collagen content and optionally oxyhemoglobin and/or de-oxyhemoglobin maps. The methodology for determining collagen content is described in more detail with respect to FIG. 2B. The generated PA images can then be stored in the data store 122 and/or electronically communicated to other devices. The digitized RF acoustic response signals 128, and the one or more property maps can be shown on the display 124, electronically communicated to other devices and/or stored in the data store 122.

Referring now to FIG. 2B, shown therein is a flow chart diagram showing an example embodiment of a PA imaging method 200 for determining collagen content of a biological sample in accordance with the teachings herein. While the method 200 is described with reference to the imaging system 100, it is important to note that the method 200 can be performed using any suitable PA imaging system that contains the wavelengths required for spectral unmixing for collagen identification. In addition, while the method 200 is described in conjunction with performing PA imaging and assessment of a kidney, it can be used with other organs, such as livers or cancerous tumors or other organs and tissue as described previously.

At act 202, the method includes preparing the kidney for imaging. This can include placing the kidney in a container that is filled with a saline solution or other physiologic fluid such as, but not limited to, University of (UW) Wisconsin solution, a Histidine-Tryptophane-Ketoglutarate (HTK) solution, Collins solution, Celsior solution, Kyto University solution, or IGL-1 solution. The solution may have a temperature in the range of 4° C. to 10° C., and more preferably at 4° C. which is the temperature used when kidneys are stored prior to transplantation. The container is then placed beneath the head of the probe 102.

At act 204, the method 200 includes generating the light stimulus signals and providing the light stimulus signals to the portion of the organ (e.g. kidney) that is being imaged. This may be automatically controlled by the processing unit 118 of the imaging unit 104 such that the PA imaging is done according to certain scan trajectories for 2D and/or 3D imaging, examples of which are shown in FIG. 4B, and by automated movement of the probe 102 via the motor 106 and the moveable mount 108.

For example, in 2D scanning, enough RF acoustic response signals are obtained to generate a certain number of temporal 2D PA image data frames total such as, but not limited to, about 50 to 80 frames and more preferably about 60 frames, for example, along a given cross section of the object 110. For example, when the object 110 is the kidney, the PA image data can be obtained along a transverse slice through the longest point of the object being imaged, such as a full mouse or full human kidney, for example. In general, the amount of 2D scanning for generating the number of frames may be varied depending on the SNR of the PA image data.

For 3D scanning, the RF acoustic response signals for 2D scanning are obtained for longitudinal cross-sections of the object 110 where the cross-sections are separated by a certain uniform distance. For example, when the object 110 is the kidney, the 2D PA image data can be obtained at intervals of from about 50 to 300 μm, and more preferable about 150 μm, across the entire kidney to capture intra-kidney variation in collagen content. The interval depends on the steps sizes that can be provided by the motor 106, how fine the sampling is desired and how long the imaging should take since a smaller step size and finer sampling leads to longer imaging time.

For the 2D and 3D scanning, the light stimulus signals are generated to have a unique wavelength based on the absorption spectra for the three dominant chromophores in the kidney, as well as most tissues and organs, which is namely HbO, Hb and collagen. The fluence used for generating the light stimulus are selected based on an ANSI standard specified by the Laser Institute (such as ANSI Z136, for example). The wavelengths are determined in order to perform PA imaging and estimation of collagen content within ex-vivo kidneys in the presence of varying degrees of blood, and consequently, varying HbO and Hemoglobin levels. In accordance with the teachings herein, the light stimulus signals are generated so that they each have one of three unique wavelengths in the range of about 680-930 nm. The wavelength range of about 680-930 nm is a region where the absorption of water is lowest compared to other tissue chromophores. The three light stimuli signals are generated and shone on the portion of the object 110 being imaged in a time sequential fashion in accordance with the signal processing techniques used for post-processing the acquired PA image data. For example, the signal processing may use signal averaging in which case a plurality of signals are generated and shone on the object 110 for each of the three unique stimulus wavelengths.

In at least one embodiment each light stimulus signal may be a single laser pulse that is a certain time duration, such as on the order of several nanoseconds long, and has one of the three unique wavelengths. For example, a light stimulus signal may have a single wavelength of 680 nm (and is therefore red in color). The laser emitter 112 may emit multiple pulses having the same wavelength to generate as much PA imaging data as is needed for imaging a certain number of PA image frames. For example, if 60 frames of PA data are needed, then the laser emitter 112 may generate 60 light stimulus signals each having a pulse at a first wavelength, followed by 60 light stimulus signals each having a pulse at a second wavelength and 60 light stimulus signals each having a pulse at a third wavelength (60 times in 2D vs 1 time in 3D). For every light stimulus having a single pulse that is shone on the object 110, one PA RF acoustic response signal is received.

The three unique wavelengths used in the light stimulus signals are determined based on using linear spectral unmixing to fit the PA imaging data (i.e. the measured PA signals being the RF acoustic response signals) across multiple wavelengths to the linear combination of the dominant chromophores that are present in kidney (i.e. HbO, Hb, and collagen). Restrictions may be implemented to improve chromophore quantification by limiting the output of the spectral unmixing to between 0% and 100% to avoid non-physical solutions (e.g. oxygen saturation <0%) and requiring that concentrations of all chromophores together sum to 100%. In alternative embodiments, another spectral unmixing technique may be used.

Accurate collagen quantification can be done from the measured PA signals by identifying the optimal wavelengths for collagen detection at which the Variance Inflation Factor (VIF) from the extinction coefficients of each chromophore (collagen, deoxyhemoglobin and oxyhemoglobin) [59] was minimized. The VIF is a metric that quantifies the stability of a solution by detecting the multicollinearity of an input matrix (in this case a matrix of the extinction coefficients). The collinearity of the vectors comprising the matrix of known extinction coefficients typically results in high VIFs, therefore requiring the minimization of the VIF. This translates into unstable solutions of the unmixing solution, unless the VIF is minimized. The VIF minimization was implemented using PA measurements obtained from the studies discussed in more detail below, and it was determined that wavelengths in a range of about 680-930 nm range were best for estimating collagen with wavelengths at about 680, 725 and 755 nm being the optimal wavelengths for estimating collagen concentration in the presence of HbO and Hb as well as providing the most stable spectral unmixing solutions. However, in alternative embodiments, it is possible to use other wavelengths which are within 10 to 20% of the 680, 725 and 755 nm wavelengths described herein.

In order to perform the VIF minimization, an energy compensated PA image, as discussed below, at each wavelength $\lambda_i$ at location (x, y) (i.e. PA($\lambda_i$, x, y)) was assumed to be dependent on the absorption of the endogenous chromophores in the kidney hemoglobin (oxyhemoglobin and deoxyhemoglobin) and collagen (Coll). This can be written as:

$$PA(\lambda_i, x, y) = \varepsilon_{HbO_2}(\lambda_i) C_{HbO_2}(x,y) + \varepsilon_{Hb}(x,y) C_{Hb}(x,y) + \varepsilon_{Coll}(\lambda_i) C_{Coll}(x,y) \quad (3)$$

where, $\varepsilon_{HbO_2}(\lambda_i)$, $\varepsilon_{Hb}(\lambda_i)$ and $\varepsilon_{Coll}(\lambda_i)$ are the known molar extinction coefficients of oxyhemoglobin, deoxyhemoglobin and collagen at wavelength $\lambda_i$, respectively. The values $C_{HbO_2}(x,y)$, $C_{Hb}(x,y)$ and $C_{Coll}(x,y)$ are the concentration of oxyhemoglobin, deoxyhemoglobin and collagen at location (x,y), respectively.

The relative concentrations (or PA chromophore scores) of the three dominant absorbers can be estimated by solving the set of linear equations using the least squares model with a constraint that the negative concentrations of any of the absorbers cannot be negative (negative concentrations were set to zero). Additionally, the imposed positivity in the reconstructed relative concentrations required that $C_{HbO_2}(x,y) + C_{Hb}(x,y) + C_{Coll}(x,y) = 1$. The unmixing solution can be written in matrix form as:

$$\begin{bmatrix} C_{HbO_2}(x,y) \\ C_{Hb}(x,y) \\ C_{Coll}(x,y) \end{bmatrix} = (\varepsilon^T \varepsilon)^{-1} \varepsilon^T P \quad (4)$$

where:

$$P = \begin{bmatrix} PA(\lambda_1, x, y) \\ PA(\lambda_2, x, y) \\ PA(\lambda_3, x, y) \end{bmatrix} \quad (5)$$

and $$\varepsilon = \begin{bmatrix} \varepsilon_{HbO_2}(\lambda_1) & \varepsilon_{Hb}(\lambda_1) & \varepsilon_{Coll}(\lambda_1) \\ \varepsilon_{HbO_2}(\lambda_2) & \varepsilon_{Hb}(\lambda_2) & \varepsilon_{Coll}(\lambda_2) \\ \varepsilon_{HbO_2}(\lambda_3) & \varepsilon_{Hb}(\lambda_3) & \varepsilon_{Coll}(\lambda_3) \end{bmatrix} \quad (6)$$

The selection of the most optimal wavelengths for the unmixing depends on the stability of the unmixing solution. This is achieved by quantifying the stability of the solutions from the extinction coefficients matrix E. The collinearity in matrix E typically produces unstable solutions which results in high variation inflation coefficients (VIFs). This can be addressed by performing the calculation of the VIFs and the minimization of the VIFs.

Three random wavelengths were selected in order to create an initial 3×3 matrix of the extinction coefficients of each chromophore at the respective wavelengths. This matrix was multiplied by its transpose and the inverse of the product was computed. The diagonal of the inverted matrix represents the VIFs of that matrix. In order to determine the most optimal wavelengths that provide the most stable unmixing solution, all possible three-wavelength permutations in the 680-930 nm range were tested, at 1 nm intervals. For each combination, the VIF was computed. The outputted VIFs at every set of wavelengths were then minimized by sorting the VIFs in increasing order across all wavelength permutations. This procedure determined that the extinction coefficients at about 680, 725 and 755 nm yield the most stable spectral unmixing solution.

The mathematical approach using the minimization of the VIF allows one to exploit differences in the spectra of the chromophores even when there are no discernable features, as is the case for collagen in the shorter wavelength range (e.g. less than 1000 nm). Furthermore, using a stimulus having three wavelengths allows for a more computationally effective (i.e. faster) approach to unmixing the concentrations of the chromophores, thus reducing the imaging time, as well as preserving the light emitter 112 longevity. In particular, the light emitter 112 does not need to have to be fired as long compared to generating a plurality of light stimuli for the case where more than three wavelengths are used for the PA imaging. For example, in 2D PA imaging, when using three wavelengths and obtaining 60 frames of PA imaging data, the light emitter 112 generates one group of 60 light stimulus signals having a first wavelength, followed by a second group of 60 light stimulus signals having a second wavelength and finally by a third group of 60 light stimulus signals having a third frequency for a total of 180 light stimulus signals. In contrast, for other techniques where 10 or more wavelengths are used then there would be at least 600 light stimulus signals that would be generated by the light emitter 112. Moreover, the three stimulus wavelengths of about 680, 725 and 755 nm do not require heavy water as a coupling medium for performing PA imaging and they also do not require a specially designed transducer and can theoretically be used by any PA imaging system or application without any restrictions.

At act 206, the method 200 includes acquiring the RF acoustic response signals when the light stimuli with the different illumination wavelengths, as explained previously, are shone on the kidney during imaging. The RF acoustic response signals comprise three sets of RF acoustic response signals where each set of RF acoustic response signals was generated by a portion of the object 108 when it was illuminated with one of the three light stimuli each having a unique wavelength. The acquired RF acoustic response signals are measured by the transducer 114 and digitized by the ADC 120.

The RF acoustic response signals can be organized in a 2D manner to form a 2D amplitude matrix similar to that shown in FIG. 2C where the transducer 114 has a linear array of M ultrasound sensors. The RF acoustic response signals are sampled for each sensor $S_i$ over time when illuminating a portion of the object 110 with a stimulus light signal $L_{ik}$ having an illumination wavelength $\lambda_i$, where i=1, 2 or 3 and k varies from 1 to P where P is the total number of light stimulus signals at a given wavelength $\lambda_i$. These RF acoustic response signals for a given illumination wavelength $\lambda_i$ can be collectively referred to as a set of P RF acoustic response signals when there are P light stimulus signals having the same wavelength. The time value that each sample of an RF acoustic response signal was obtained is converted to a depth $D_i$ value by multiplying the sample time with the speed of sound. The data from subsequent light stimuli can be organized as other 2D data sets which together can be organized as a 3D data set (i.e. a 3D amplitude matrix) for light stimuli $L_{11}$ to $L_{1P}$ as shown in FIG. 2D. Therefore, there can be three 3D amplitude matrices when imaging using three wavelengths.

At act 208, the method 200 includes performing preprocessing on the acquired RF acoustic response signals. This may include performing beamforming at act 208a followed by performing noise reduction at act 208b. The noise reduction at act 208b may be optional when the acquired RF acoustic response signals have sufficient SNR for further processing.

At act 208a, the method 200 involves applying beamforming to generate a matrix of beamformed RF acoustic response signals. The beamforming can be done in several ways. For example, when the transducer 114 has a linear array of ultrasound sensors, the delay and sum method can be used to perform beamforming using a sliding window on a subset of response data from the different ultrasound sensors. For example, there can be 256 ultrasound sensors, and the sliding window can be defined to include the data from 64 ultrasound sensors and the beamformed value for a given sensor $S_i$ includes a delay waited sum of the values sensed from sensor number $S_{i-32}$ to sensor number $S_{i+32}$ when such sensors exist. This is repeated for each depth position to obtain a beamformed 2D data set. This is then applied to each frame for the 2D PA data and the 3D PA data that was acquired.

Once the beamformed PA data was obtained for all the frames acquired (i.e. for the 2D and/or 3D scanning as described below in the studies section), the beamformed PA data was compensated for the wavelength-dependent fluctuations in laser energy. This was achieved by dividing the beamformed PA matrix for a given frame by the energy of the laser used to generate the light stimuli when the RF acoustic response signals were obtained for that given frame. This was done for all frames of PA data.

It should be noted that in an alternative embodiment, downsampling may be performed on the RF acoustic response signals after beamforming in order to generate PA images that have a smaller number of pixels, while providing sufficient resolution. The smaller data sets then allow for more efficient processing in subsequent steps of the method 200.

The noise reduction at act 208b can be used to perform certain signal enhancement operations after beamforming. The signal enhancement operations include at least one of as amplification and/or time averaging to improve the signal to noise Ratio (SNR). Time averaging may be done for data obtained for the same depth position using successive light pulses for repeated presentations of light stimulus signals having the same illumination wavelength $\lambda_i$. For example, referring to FIG. 2D shown therein is a 3D data set where each vertical slice of data is obtained for a given light stimulus $L_{1k}$ where the light stimulus signals have the first wavelength $\lambda_1$ and are applied sequentially in time. For a given sensor Si, time averaging can be done by averaging the values across the different light stimuli for the same wavelength a given depth position $D_i$. The end result of the time averaging will be three separate 2D matrices where each matrix is for one of the three stimulus wavelengths.

The amplitude matrix can also be thresholded using Otsu's method in order to filter out other noise that may be present in the PA image data. In alternative embodiments, other noise reduction techniques may be used such as linear filters such as Mean filters or Weiner filters, or Non-linear filters such as Median filters. Alternatively, the filtering can be done in the transform domain such as spatial frequency filtering, wavelet domain filtering or Wavelet-based thresholding (which includes Non-adaptive threshold, adaptive threshold or non-orthogonal Wavelet transforms).

Although not shown in FIG. 2B, the various data sets at different points in the method 200 can be stored in the data store 122. For example, the raw acquired RF acoustic response signal data may be stored in the data store 122 after digitization. Alternatively, or in addition thereto, the noise reduced RF acoustic response signal data may be stored in the data store 122 after performing noise reduction. Alternatively, or in addition thereto, the beamformed RF acoustic response signal data may be stored in the data store 122 after beamforming.

At act 210, the method 200 includes generating PA image data from the beamformed RF acoustic response signals. This is typically done in real-time after beamforming (and optionally noise reduction) has been performed. However, there may be some embodiments in which the beamformed RF acoustic response signals (that may have optionally experienced noise reduction) are obtained from the data store 122. In such cases, acts 210 and 214 to 222 of the method 200 can be done based on previous RF acoustic response signal data and acts 202 to 208 may be optional because they may have already been performed at a previous point in time.

To form a PA image, the amplitude of each pixel of the PA image was calculated by performing the Hilbert Transform across each of the sensor channels ($S_i$) for a given depth in the PA amplitude matrix for a stimulus wavelength. To display the image, logarithmic compression may be performed by taking the $20 \times \log_{10}$ of the PA amplitude matrix. The pixel locations of a given PA image are defined by x,y coordinates where the y coordinate corresponds to one of the depth positions (e.g. one of the $D_i$ in FIG. 2C or 2D) and the x coordinate corresponds to a position of one of the sensors (e.g. one of the $S_i$ in FIG. 2C or 2D) since the array of sensor elements are physically spaced over a certain horizontal distance. In an alternative embodiment, manual segmentation of the object being imaged, such as the kidney, may be performed in order to only analyze signals from the kidney and not the rest of the PA image.

At act 212, the method 200 includes displaying and/or storing the PA image data.

At act 214, the method 200 includes performing spectral decomposition, which provides spatial data, such as a spatial distribution, which may be shown in a spatial map, of the source generators that generated the RF acoustic response signals during light stimulation. For example, if the object 108 is a tissue sample then spectral decomposition may be used to quantify the $sO_2$ in the tissue sample by generating an $sO_2$ map. One example of a spectral decomposition technique that may be used is linear spectral unmixing [20].

Figure 2E:
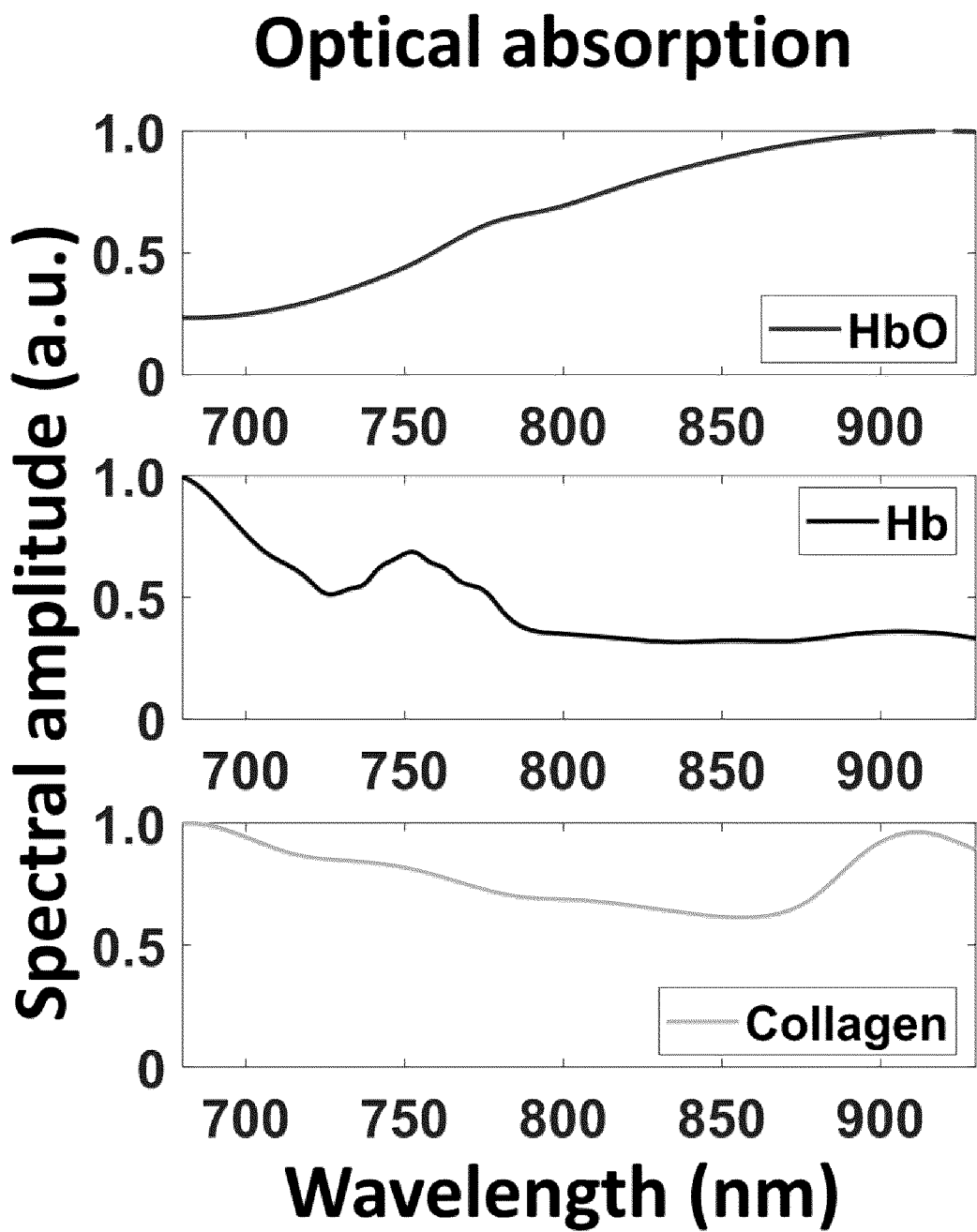
FIG. 2E shows optical absorption as a function of illumination wavelength for the dominant chromophores in the kidney.

The PA amplitude matrix for the 2D PA images obtained at each of the unique wavelengths are provided as inputs to the linear spectral unmixing algorithm which uses equations 4 to 6. The unmixing was performed using the normalized extinction coefficient plots shown in FIG. 2E ([63, 64]) for each of the three dominant chromophores. The PA amplitude matrices at each wavelength were used to solve the linear system of extinction coefficients using the least-squares method. Restrictions to the solution were implemented in order to improve the chromophore concentration quantification by limiting the output of the algorithm between 0% and 100% to avoid non-physical solutions (ex. oxygen saturation <0%) and requiring that the concentrations of all chromophores together sum to 100%.

The output of the spectral decomposition are 2D chromophore data matrices for each chromophore for a given cross-section of the portion of the object 110 being imaged. Each of these 2D data matrices can be referred to as a map. Accordingly, where the chromophores are Hb, HbO and collagen, the maps that are generated along for a given cross-section of the object upon which PA imaging was performed include Hb, HbO and collagen maps.

At 216, the method 200 includes determining collagen content by establishing a collagen score for a given collagen map. This may be done by performing certain computations on the collagen maps that are created from the spectral decomposition. For example, for a given collagen map, the mean pixel value may be determined to obtain a collagen score. Alternatively, a histogram distribution of each pixel amplitude in the given collagen map may be determined and the collage score for the given collagen map may be the mode of the histogram which represents the most commonly occurring pixel value in the collagen map. Alternatively, the collagen score may be the median of that histogram.

The collagen score can be determined for a given 2D PA image for a cross-section of the portion of the object 110 (i.e. the kidney) being imaged. When 3D scanning is used on the kidney, there are a plurality of collagen maps that are generated with one collagen map being generated for each 2D image slice of the 3D PA image data. A collagen score can then be determined for each collagen map to generate a set of collagen scores. The overall collagen score can then be taken as the mean, median or mode of the set of collagen scores. The overall collagen score provides an assessment of the overall collagen for the entire kidney.

At 218, the method 200 includes performing kidney assessment for the kidney for which PA imaging was performed. This may be done by comparing the collagen score determined at act 216 with a threshold value to assess the amount of collagen in the kidney and whether the kidney is suitable for transplant. The threshold value may be obtained by conducting a clinical trial with actual transplanted kidneys in which the kidneys are imaged pre-transplantation and then the recipients of these kidneys for several years post-transplant are followed and assessed to see how well the kidneys function. For example, donor recipient plasma creatinine and urine albumin-to-creatinine levels (tests of kidney function) may be recorded monthly for the first-year post-transplant and then every 3 months until 5 years post-transplant (as per routine clinical practice) to determine clinical outcome. The threshold collagen value can then be determined for kidneys with collagen above a certain amount where the kidneys do not perform well within the patient.

The method 200 may then display the assessment on the display 124 or send an electronic message with the assessment to a medical practitioner or some medical device, which may be part of an electronic medical record system of the PACS of a medical institution, for example. If the kidney assessment is favorable then the kidney may be classified for transplant for a particular donor and then transplanted to the donor soon thereafter. For example, kidneys with better assessments due to having less collagen content can be transplanted to patients who are younger or have a longer life expectancy, as explained earlier.

At 220, the method 200 includes displaying and/or storing the map(s). For example, one or more of the collagen, Hb and HbO maps obtained from PA imaging for a given cross-section of the kidney may be displayed and/or stored. Alternatively, one or more of the collagen, Hb and HbO maps obtained from PA imaging for various cross-sections of the kidney may be displayed and/or stored. In this latter case, i.e. for 3D PA imaging, in at least one embodiment these maps can be displayed sequentially in time with a small time step to allow a medical practitioner to visually "scan through" the kidney.

Studies to Validate PA Imaging Technique to Detect Collagen in Kidneys and Collagen Phantoms Test Setup, Imaging Parameters and Sample Preparation Studies were conducted to validate the use of PA imaging to detect collagen in collagen phantoms, as well as mouse, pig and human kidneys. The studies were performed with the VevoLAZR-X system (Fujifilm VisualSonics Inc., Toronto, Canada) [58, 74, 75] which operates an Nd:YAG laser 512 nm source through an Optical Parametric Oscillator (i.e. laser) operating at 10 Hz pulse repetition frequency. The VevoLAZR-X system includes a hand-held linear array probe (15 MHz center frequency, 256 acoustic elements) that is capable of emitting 6 ns short laser pulses (680-930 nm) from two rectangular strips located at a 30° angle on both sides of the acoustic aperture of the transducer for performing ultrasound imaging. Co-registered ultrasound and photoacoustic image data are sampled at an imaging interval of 5 Hz. Ultrasound imaging was also done as part of the study but does not have to be used with the embodiments of the systems and methods described herein. The system also provides full access to the RF signals for PA images collected at each wavelength of illumination, which permitted the validation of algorithms for the accurate quantification of collagen in whole kidneys in accordance with the teachings herein. The probe is mounted to a 3D motor which can perform scanning at micron step sizes, permitting collagen quantification across maximal volumes of kidney tissue. Accordingly, the probe is used for sensing RF response signals due to the illumination signals provided to the kidney. The RF response signals are sent back to the hardware unit for processing and storage.

FIG. 4B shows the PA imaging orientations employed during the study. With the exception of the pig kidneys, all imaging was performed in a 4° C. saline bath to mimic the temperature at which kidneys are stored prior to transplantation. The saline bath serves as the coupling medium for acoustic propagation (see FIGS. 4A, 5A, 7A and 8A). Once the kidney is positioned below the probe, the laser and ultrasound are turned on and imaging commences.

In the studies, for all kidneys and collagen phantoms, a spectral sweep was first performed in the 680-930 nm optical window and repeated for a total of five times. This initial sweep was followed by 2D imaging, during which 60 PA temporal frames were recorded in the same location of the specimen (at the renal hilum in mouse kidneys and whole human kidney, and at a pre-specified cross-section in human nephrectomy specimens; see FIGS. 5A, 6A, 8B, and 8F), at each of the three key wavelengths identified as most optimal for unmixing collagen. The 60 temporal frames were collected to improve signal-to-noise ratio. Accordingly with 2D imaging, a single longitudinal slice through the middle of the kidney was imaged. Therefore, 2D imaging captured only one large section of the kidney but was performed in less than about 1.5 minutes.

Figure 5A:
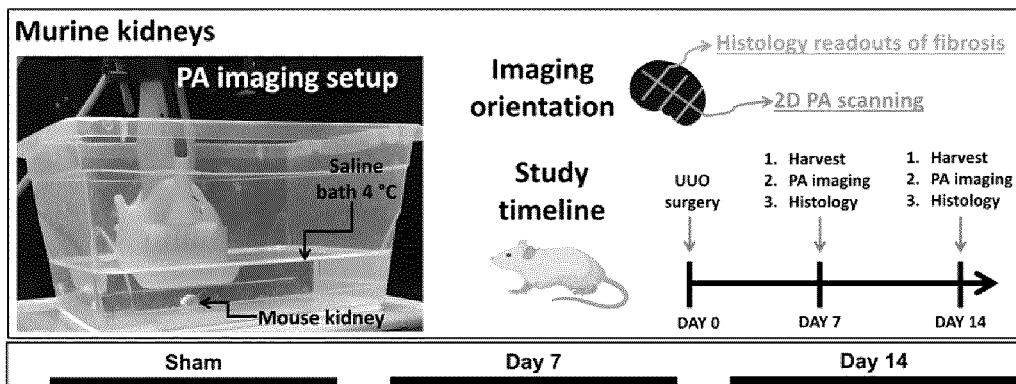
FIGS. 5A-5E show study details and results for using PA imaging to detect progressive kidney fibrosis in mice.
Figures 8A, 8B:
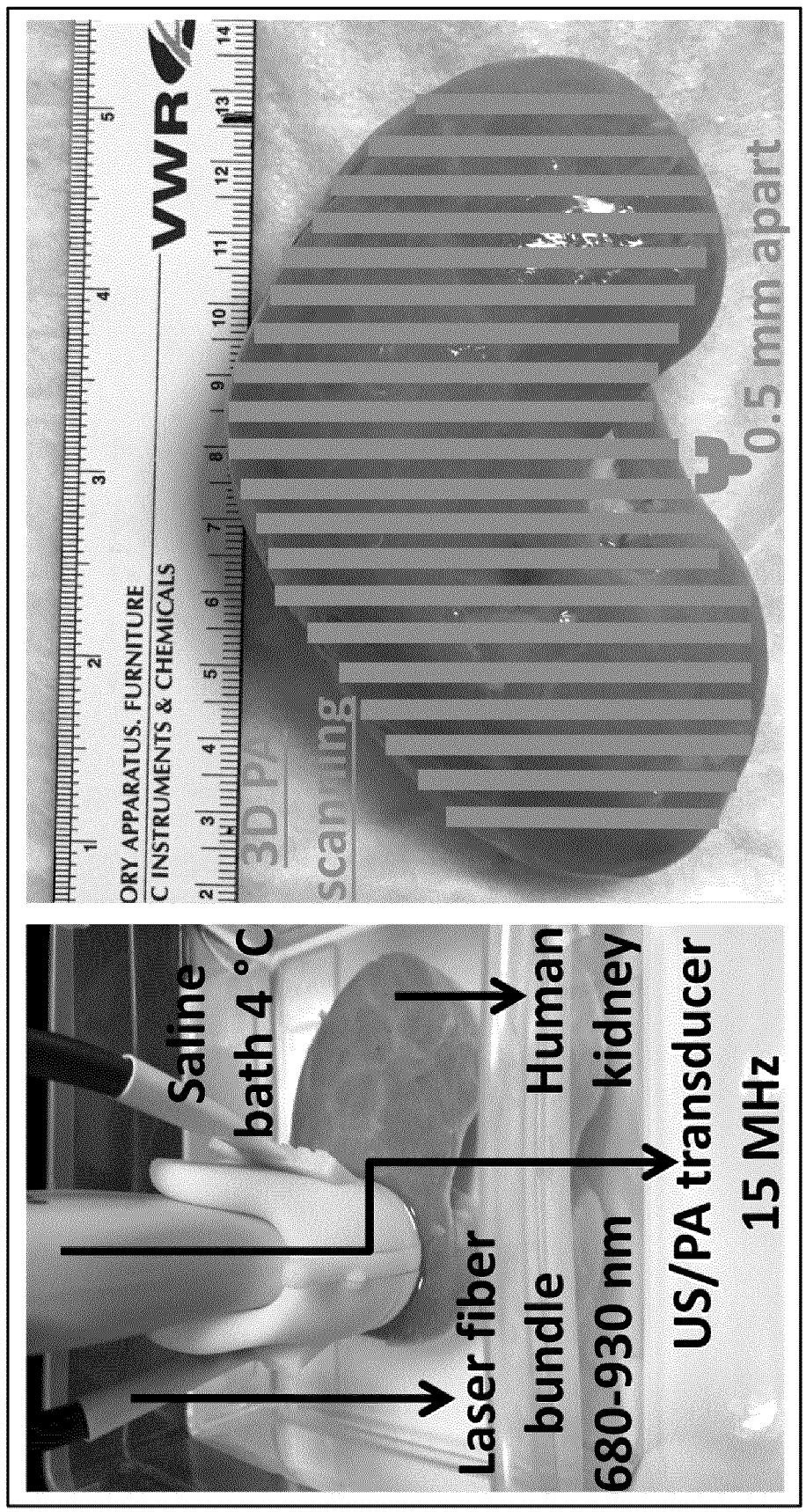

With 3D PA imaging, the PA probe was moved over each specimen, at each of these three wavelengths, to quantify the heterogeneity of collagen distribution within each kidney (see FIGS. 5A and 8B for schematics). A step size of 150 µm was generally employed. For mouse kidneys, 130 sequential frames were collected for the radical nephrectomy samples (total length covered 20 mm) and 60 sequential frames were collected (i.e. for a total length covered 9 mm). This allowed for imaging of the entire kidney in the case of mice. For the whole human kidney, 3D imaging was performed on both sides of the kidney with a step size of 0.5 mm, covering 45 mm in length during 90 acquired sequential frames. Accordingly, with 3D PA imaging, multiple axial slices were images, beginning at one pole and progressing to the other pole. This detailed, high spatial resolution 3D PA imaging was typically completed in under 5 minutes for mouse kidneys and 15 minutes for a full human kidney. Accordingly, this imaging technique may be performed while a recipient is being prepared for transplantation, and thus the critical time that the kidney remains on ice between donor and recipient (cold ischemia time) is not prolonged by performing this PA imaging technique.

Test Sample Information

Collagen phantoms were constructed consisting of porcine skin gelatin, which is composed mostly of type I collagen [57] (Sigma-Aldrich Co., St. Louis, MO, Cat. #: 9000-70-8), admixed with whole pig blood. Varying amounts of gelatin and pig blood were mixed to form different phantoms. The weight-to-volume concentration of the gelatin powder was 10%, 15%, 20% and 25% in relation to the whole blood concentration of 90%, 85%, 80% and 75%, respectively. Whole blood was collected from the great saphenous vein of the same pigs used for kidney harvesting. In order to construct each phantom, PBS was heated to 35° C. before the gelatin powder was slowly added. The suspension was magnetically stirred to achieve homogeneity until it reached 75° C. and the gelatin was entirely dissolved. The solution was cooled to 37° C. before adding the appropriate volume of whole pig blood kept in $K_2$ ETDA vacutainers (Fisher Scientific Company, Ottawa, Canada, Cat. #02-689-4) to prevent clotting. The blood-collagen suspension was added to 35 mm tissue culture dishes (Corning Inc., Corning, NY, Cat. #353001) and was kept at 4° C. for 24 hours in order to achieve full solidification prior to imaging.

All animal studies were approved by Unity Health Hospital Animal Ethics Committee and conformed to the Canadian Council on Animal Care guidelines. Male wild type C57BL/6 mice were purchased from Charles River (Charles River, Wilmington, MA). Mice were kept on a 12-hour light-dark cycle with ad libitum access to food and water.

Six to eight-week-old male wild type C57BL/6 mice underwent sham (n=5) or left-sided UUO surgery (n=10) as previously described [60]. A left-sided flank incision was made in anesthetized mice, and the left kidney and ureter were identified. For UUO animals, the left ureter was then obstructed with two 4-0 silk suture ties just distal to the renal pelvis. For sham-operated animals, a similar flank incision was made, but the ureter was not obstructed. UUO mice were divided into two groups that varied in their degree of induced fibrosis: (1) mice sacrificed at 7 days post-surgery (n=5), and (2) mice sacrificed at 14 days post-surgery (n=5). The sham mice were sacrificed at 14 days after sham surgery.

Kidneys from two Yorkshire pathogen-free female pigs from Lifetime Solutions (pig 1: 46.4 kg, pig 2: 41.7 kg) were harvested immediately following sacrifice of n=2, female, X±Y kg pigs. Whole pig kidneys were then subjected to PA imaging as detailed herein. Each left kidney was first imaged in a phosphate buffered saline (PBS, Millipore-Sigma, St. Louis, MO Cat. #524650) bath kept at 37° C. (immediately after harvesting), followed by 8-hour storage at 4° C. The second imaging session was performed in a 4° C. PBS bath to examine the impact of temperature on the quantification of collagen at clinically relevant imaging depths.

For human kidney tissue samples, ethics approval was secured from the Unity Health Toronto Research Ethics Board (REB #18-193) to collect available residual nephrectomy kidney tissue during radical nephrectomy procedures (i.e. complete kidney resections) performed at St. Michael's Hospital in Toronto. A portion of the renal cortex and medulla was collected from the radical nephrectomy (n=5 kidneys). These specimens were submerged in 4° C. PBS and were imaged within 4-6 hours post-collection.

For whole human kidney samples, a non-transplantable human kidney was procured from the International Institute for the Advancement of Medicine (IIAM), under the same Unity Health Toronto Research Ethics Board (REB #18-193)-approved research protocol described above. The IIAM recovers organs not suitable for transplant when authorization for research usage has been obtained from the donor's family. The kidney was stored in ice during transport to minimize ischemic injury and was imaged within 24 hours post-collection.

Tissue Collection, Preparation, and Histochemistry

Following PA imaging, each kidney (mice, pigs and human) was immersed in 10% neutral buffered formalin for immediate fixation and/or stored in RNAlater (Invitrogen, Carlsband, CA, Cat. #7020). Formalin-fixed tissues were embedded in paraffin and sectioned before staining with picrosirius red (PSR, Millipore-Sigma, Cat. #365548), Masson's Trichrome (Millipore-Sigma, Cat. #HT15-1KT) or antibodies against α-smooth muscle actin (α-SMA, 1:100 dilution, Agilent Dako, Santa Clara, CA, Cat. #M0851),) and type I collagen (Collagen I, Southern Biotechnology, Birmingham, AL, Cat. #1310-01). Random, non-overlapping 20× cortical images were taken by a blinded observer using an upright Olympus light microscope (Tokyo, Japan), and then analyzed in blinded fashion using the Aperio Imagescope software as previously described [60]. The collagen content within each image was defined as the percentage of positive pixels. Whole sample histology-derived collagen scores were then computed by averaging the individual scores from four to six non-overlapping cortical images.

Semi-Quantitative Reverse Transcription PCR

Tissue stored in RNAlater was homogenized and RNA isolated with TRIzol (Life Technologies, Cat. #15596108). RNA was then reverse transcribed into cDNA with Multiscribe Reverse Transcriptase (Thermo Fisher Scientific, Cat. #4311235), and levels of Col1a1, Col3a1, Col4a1, Acta2, and/or Gapdh were quantified. The primer sequences are summarized in Table 1. Experiments were performed in triplicate. Data analyses were performed using the Applied Biosystems Comparative CT method. All values were referenced to the mRNA transcript levels of the housekeeper gene Gapdh.

TABLE 1 qPCR primer sequences

| Collagen type | Primer sequence |
| --- | --- |
| Mouse Col1a1 forward | GAGAACCAGCAGAGCCA |
| Mouse Col1a1 reverse | GAACAAGGTGACAGAGGCATA |
| Mouse Col3a1 forward | GAAAGGATGGAGAGTCAGGAA |
| Mouse Col3a1 reverse | CATTGCGTCCATCAAAGCC |
| Mouse Col4a1 forward | TTCTCCCTTTTGTCCCTTCAC |
| Mouse Col4a1 reverse | GCTTCTGCTGCTCTTCGC |
| Mouse Acta2 forward | CACTGAACCCTAAGGCCAAC |
| Mouse Acta2 reverse | GAGTCCAGCACAATACCAGTT |
| Mouse Gapdh-2 forward | CACCATCCGGGTTCCTATAAAT |
| Mouse Gapdh-2 reverse | TGGCACTGCACAAGAAGAT |

Evaluating Inter-Kidney PA Estimates of Collagen Concentration

The average PA collagen score was computed for both the 2D and 3D imaging orientations in mouse and human kidneys. For 2D imaging, the mean collagen score for each kidney was calculated by averaging the collagen scores derived from the individual 60 PA images acquired at each wavelength, at the same spatial location within the kidney. For the mouse kidneys and human radical nephrectomy specimens, this mean score was then correlated against mean histological measures of fibrosis (obtained from PSR, type 1 collagen, and α-SMA stains acquired from three locations within the kidney, as shown in FIG. 5A) using Pearson linear correlation analysis [61]. For mouse kidneys, the mean PA-derived kidney score was also correlated against fibrosis-associated transcript levels (Col1a1, Col3a1, Col4a1, Acta2).

Similarly, for 3D imaging, a mean PA-derived collagen score for each mouse kidney or human radical nephrectomy specimen was calculated by averaging the collagen score for each image captured as the probe was moved sequentially across the kidney. This mean PA-derived collagen score was then compared against gold standard mean histologic measures of fibrosis as described above.

Evaluating Intra-Kidney PA Estimates of Collagen Concentration

Figure 8F:
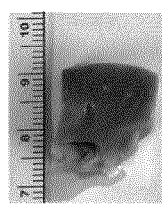
Figure 8F:
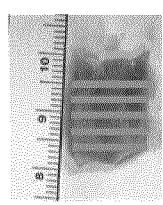
Figure 8F:
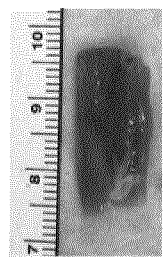
Figure 8F:
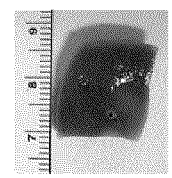
Figure 8F:
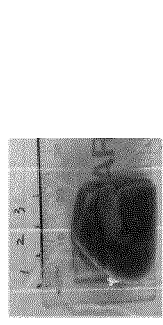

For mouse kidneys and human radical nephrectomy specimens, the intra-kidney collagen variation was assessed by comparing the 3D PA-derived collagen scores collected over the entire mouse kidney, or over ~20 mm of human kidney tissue, against the average PSR and Masson's Trichrome-derived fibrosis scores acquired at three-to-four locations within the sample, taken approximately 5 mm apart (see FIG. 8F).

Figure 9A:
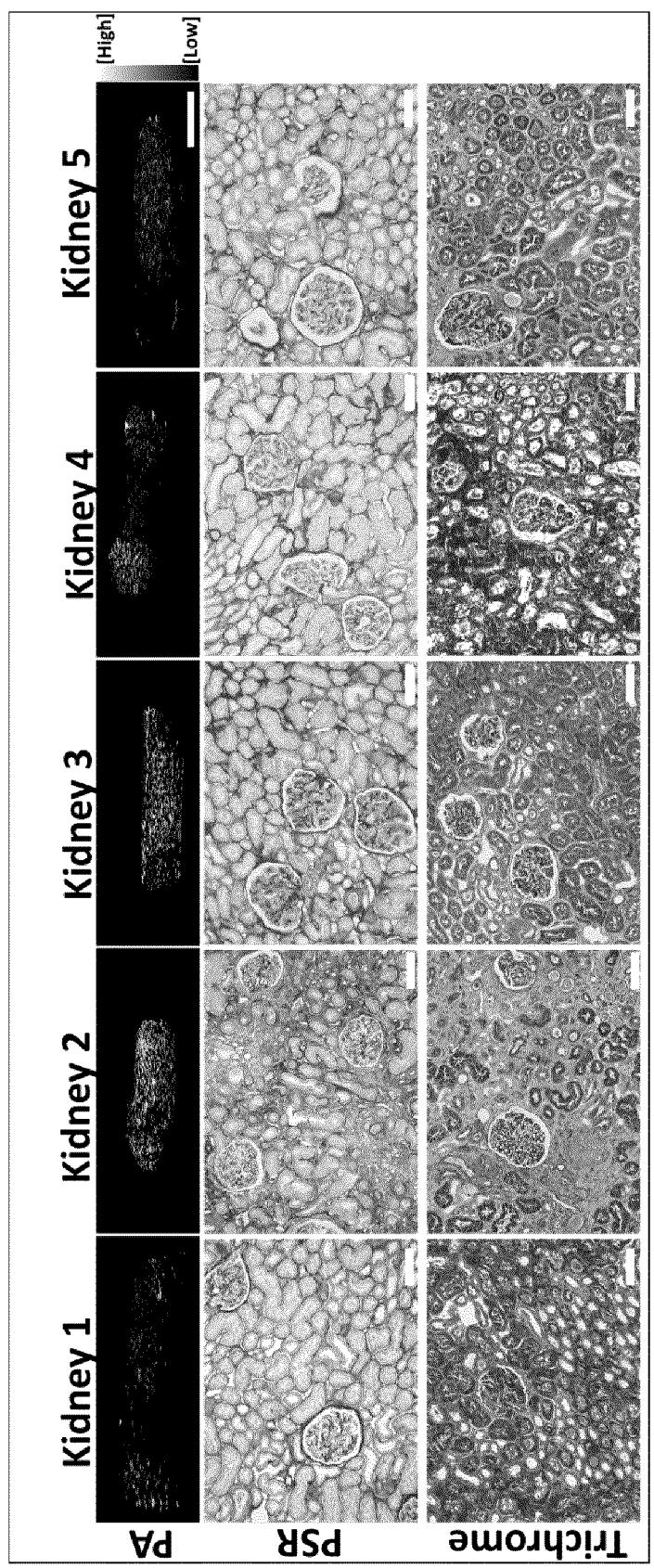
FIGS. 9A-9C show experimental results that show how PA imaging can detect inter-kidney variations in collagen content in human kidneys.
Figure 9B:
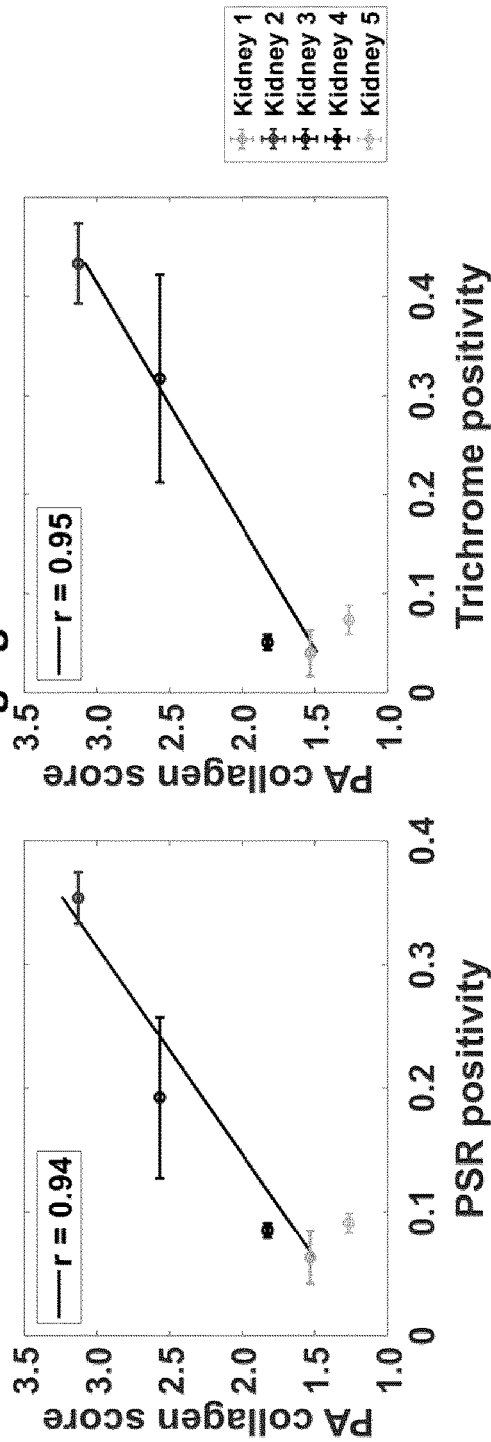
Figure 9C:
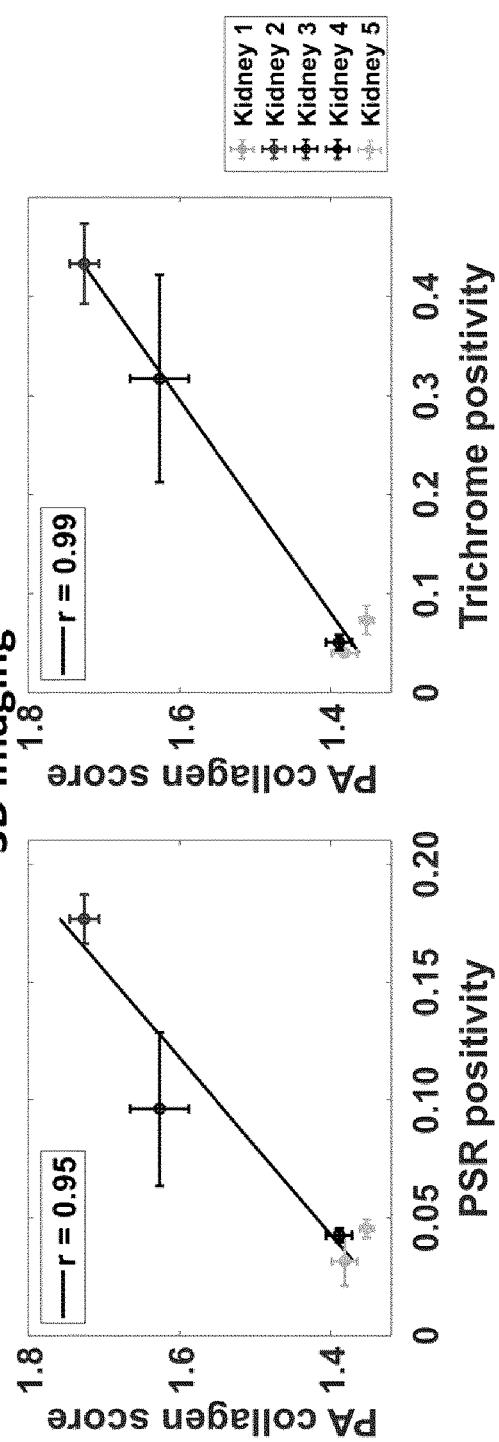

For the whole human kidney, the PSR-derived (i.e. histologic) collagen scores from the top and bottom of the kidney at four locations/side were compared with the corresponding PA collagen scores acquired from 3D scanning at these same locations using Pearson linear correlation coefficient analysis (see FIGS. 9B and 9C). For the radical nephrectomy kidney specimens, the intra-kidney collagen variation was assessed by comparing the 3D PA collagen scores over ~20 mm of kidney tissue against the average PSR and Masson's Trichrome histology acquired at three-to-four locations within the sample, taken approximately 5 mm apart. The corresponding p value was computed for each correlation and the correlation coefficient was considered statistically significant for p<0.05.

Statistical Analysis

As detailed above, Pearson linear correlation coefficient analysis was used to assess the degree of correlation between the PA estimates of renal collagen content and gold standard measures of fibrosis. A two-way ANOVA with time as an independent variable was used to assess for time-dependent changes in PA and histologic measures of fibrosis. A variable with a p value of <0.05 was considered statistically significant and post hoc comparisons using Tukey's least significant differences identified 95% confidence intervals to determine pairs that were significantly different [62]. Statistical analysis was performed using Matlab 2018b (MathWorks, Inc., Natick, MA).

Experimental Results

Study on Blood-Collagen Phantom Gels

Given the prevalence of type 1 collagen in kidney tissue and its overproduction in fibrotic kidneys [24], studies were performed to explore whether the concentration of type 1 collagen might be quantified using PA imaging. To develop and validate the PA imaging technique to detect type 1 collagen, PA imaging was performed on collagen phantom gels composed of porcine skin-derived gelatin (the major constituent of which is type 1 collagen) using the test setup shown schematically in FIG. 3A. As blood is also a major component of renal tissue and hemoglobin is a strong PA chromophore [25], varying amounts of porcine blood were also mixed into the collagen phantoms thereby creating blood-collage phantom gels. The blood-collagen phantom gels using a commercial PA system, illuminating the samples with light between 680-930 nm (see FIG. 2A for the test setup). Using the generated PA data, the spectral unmixing algorithm described previously was used to identify the optimal wavelengths that may best distinguish PA signals derived from excitation of hemoglobin versus that of collagen (see FIGS. 1A-1B).

The unmixing algorithm was applied to the scanned PA image data from the phantom gels, and it was found that the PA imaging technique described herein demonstrated remarkable accuracy in quantifying both collagen and hemoglobin content across a wide range of values as shown in FIGS. 3B and 3C. FIG. 3B shows representative co-registered ultrasound (US) and PA images of a blood-collagen phantom. The scale bar is 10 mm and applies to both images. FIG. 3C shows validation of the PA imaging technique to quantify collagen in the phantom gels. Error bars represent the standard deviation of the mean, with 60 measurements per phantom. The $r^2$ denotes the goodness of the linear fit.

Study on PA Imaging of Whole Kidneys

Another study was performed to determine if the PA methodology described herein maintains its imaging accuracy in a more complex and heterogeneous structure such as the kidney. FIG. 4A shows a conceptual image for the experimental setup that was generally used for validating the use of PA imaging with spectral unmixing for identifying collagen in kidneys. Imaging of collagen phantoms, as well as imaging of mouse, pig and human kidneys, was performed using the VevoLAZR-X system as described previously. FIG. 4B shows a conceptual image for the acquisition of 2D and 3D PA imaging data in accordance with the teachings herein.

2D PA Imaging of Whole Mouse Kidneys

Figure 5B:
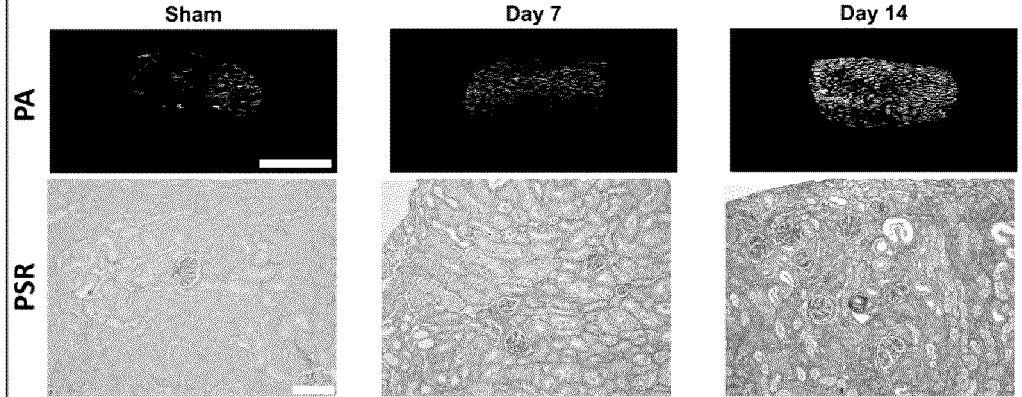
Figure 5C:
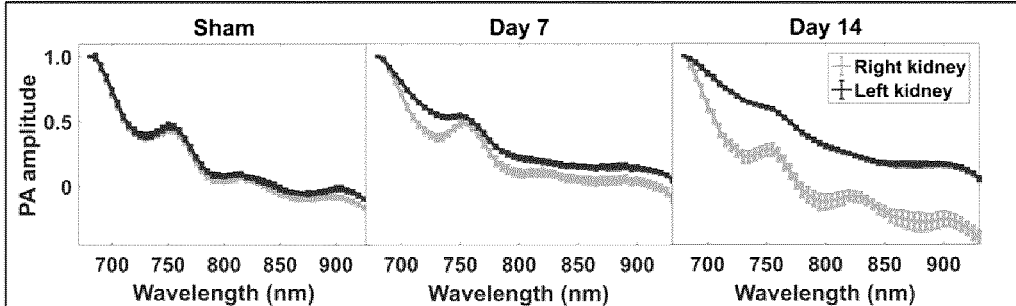

In a first study, 2D PA imaging of whole mouse kidneys was performed at various time points following left-sided unilateral ureteral obstruction (UUO). FIG. 5A shows a PA imaging setup and experimental plan for imaging UUO-induced murine kidney fibrosis. Following obstruction, the left kidney develops progressive and highly reproducible fibrosis over the course of 7 to 14 days [26] as can be seen in FIG. 5B which shows Representative PA and picrosirius red (PSR) histology images at various time points post-UUO surgery. The scale bar represents 5 mm for the PA images and 100 µm for the PSR histology images. Compared to mice undergoing sham surgery, PA imaging of a single transverse two-dimensional slice through the kidney using light ranging from 680-930 nm demonstrated marked changes in generated PA signals. This can be seen in FIG. 5C, which shows average PA amplitude spectra as a function of optical wavelength. The total scanning time per kidney was less than 1.5 minutes.

Figure 5D:
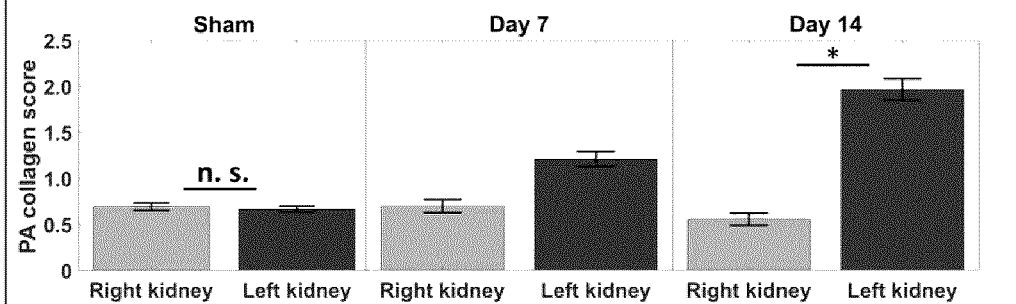
Figure 5E:
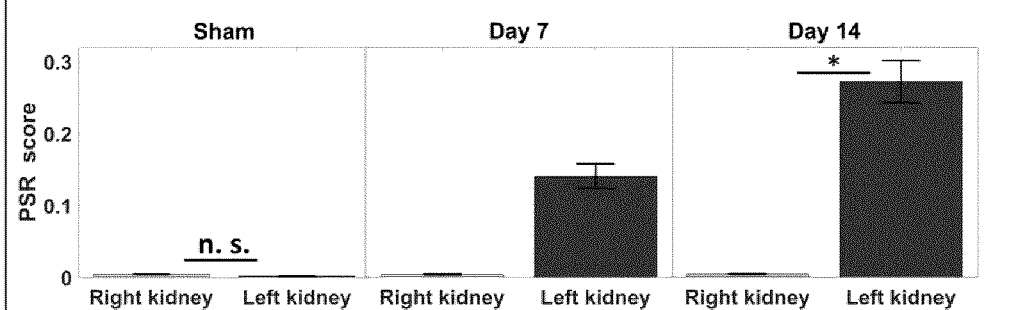

The application of the spectral unmixing algorithm using the 3 optimal wavelengths identified in the phantom experiments (i.e. 680, 725, 755 nm), demonstrated that the PA imaging method described herein detected significant increases in collagen content at 7 days post-UUO, with further increases noted by 14 days post-surgery as can be seen in FIG. 5D, which shows PA-derived collagen scores as a function of time. The right kidney is normal, and the left kidney is fibrotic. Gold standard histologic quantification of fibrillar collagen using picrosirius red (PSR) staining at these same time points closely mirrored the PA imaging findings as can be seen in FIG. 5E which shows PSR histology-derived collagen score as a function of time (*p<0.05, n.s., not significant relative to the right kidney).

Figures 10A, 10B:
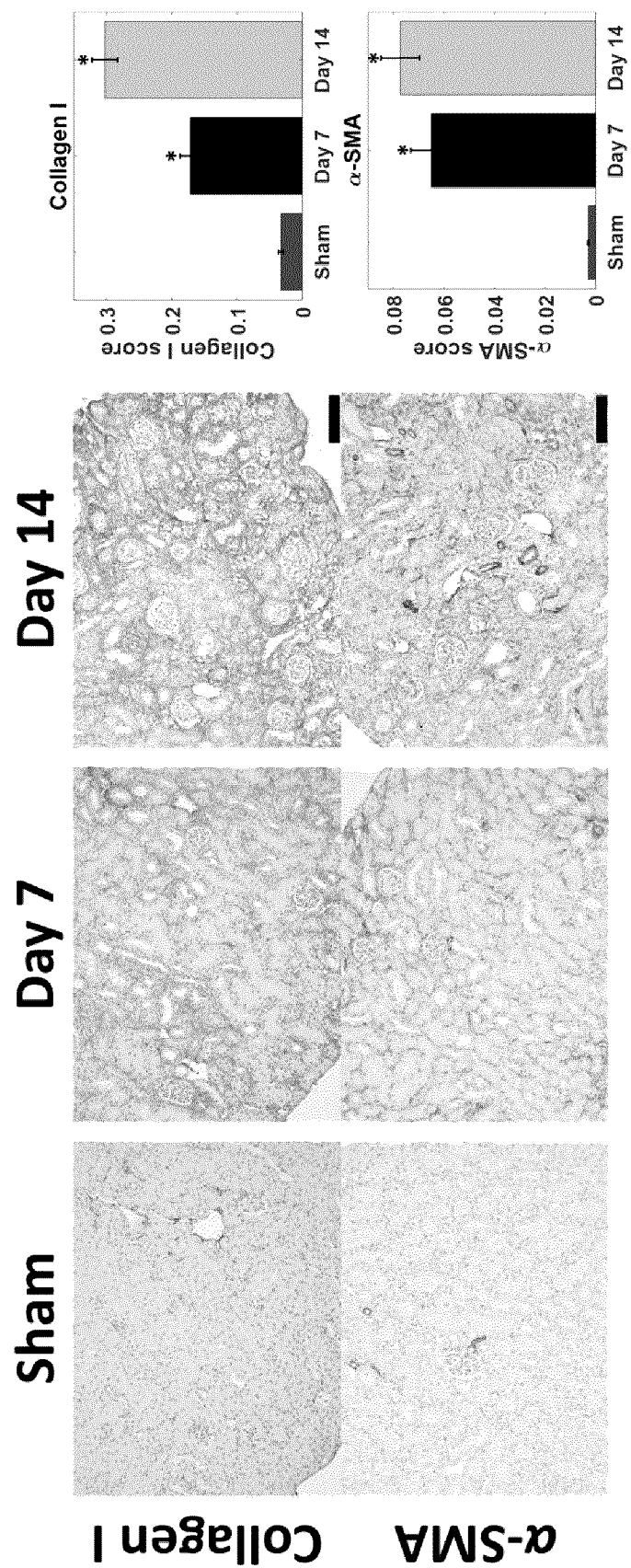
FIGS. 10A-10B show renal progression over time following unilateral ureteral obstruction (UUO).
Figure 13:
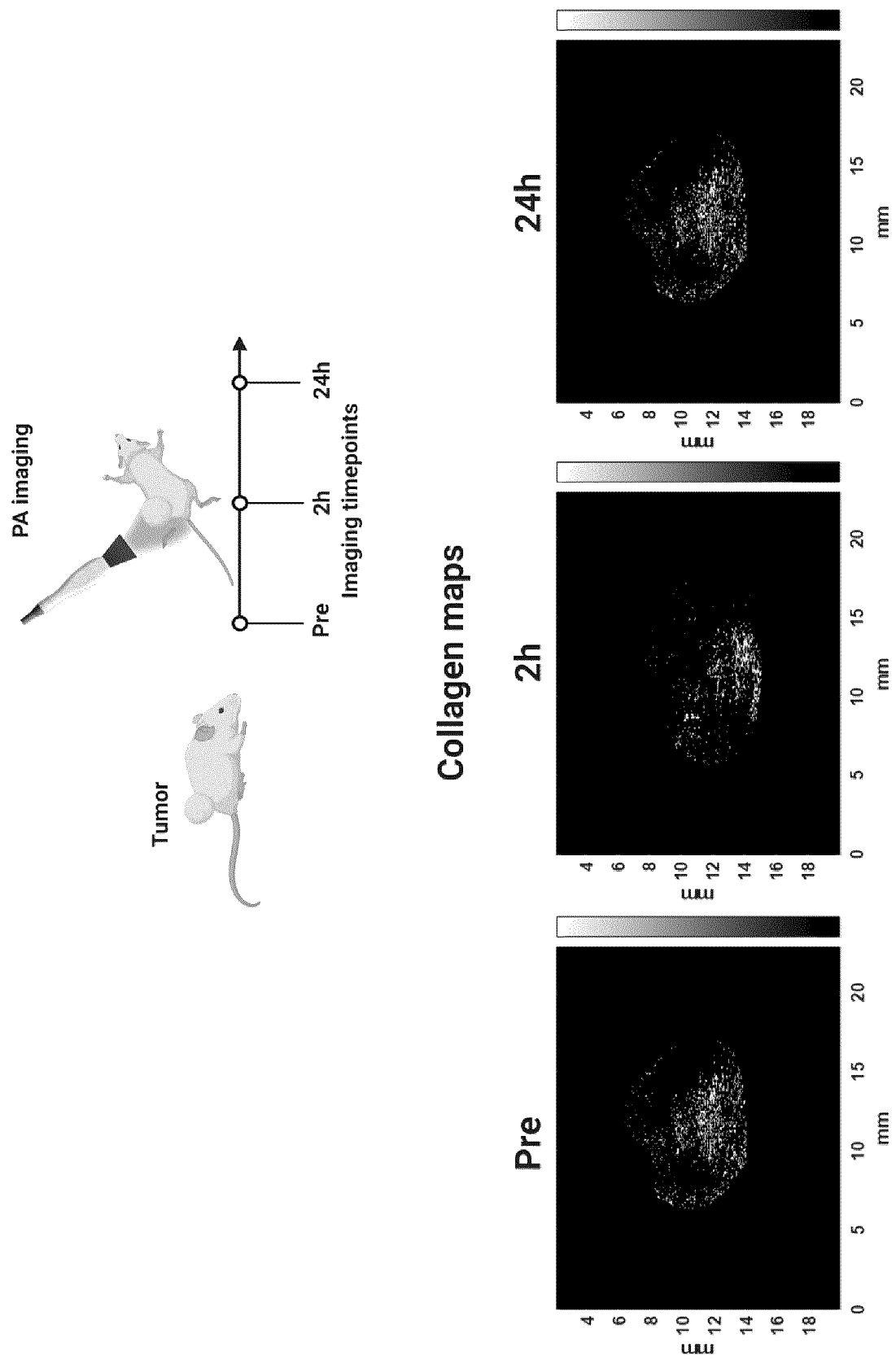
FIG. 13 shows a schematic for performing a tumor collagen study in mice and representative collagen maps.

Similar findings were noted when other commonly used histologic stains for fibrosis were used (e.g., see FIGS. 10A-10B). Importantly, correlation analysis (see the rightmost graph in FIG. 6C) demonstrated a remarkable agreement between the 2D PA imaging technique of the subject disclosure and gold standard histology measurements (Pearson rho=0.89-1.00, p<0.05 comparing PA-based collagen scores vs. either PSR or type 1 collagen immunohistochemistry-based collagen measurements). Similarly, the 2D PA-derived mean collagen scores correlated strongly with alpha-smooth muscle actin staining, a marker of activated fibroblasts, as well as mRNA levels of various fibrosis-associated genes, including Col1a1, the gene encoding type 1 collagen. For example, FIG. 10A shows representative images following staining with antibodies directed against type 1 collagen and alpha-smooth muscle actin ($\alpha$-SMA) as a function of time post-UUO surgery. The scale bar denotes 100 µm and it applies to all images. FIG. 10B shows bar graphs for quantification of type I collagen and $\alpha$-SMA staining following UUO-surgery (* denotes statistical significance with p<0.05 for relative to sham).

3D PA Imaging of Whole Mouse Kidneys

Scar deposition within the kidney is characteristically heterogeneous in distribution [27]. Thus, knowledge of where fibrotic tissue is and is not located may be helpful in guiding tissue selection for analysis. To determine whether PA imaging can detect intra-renal variations in collagen content, experiments were performed for serial three-dimensional (3D) imaging through entire kidneys, at intervals of 150 µm across the length of the kidney (see FIG. 6A). Whole 3D kidney scanning was completed in less than 5 minutes.

Figure 6A:
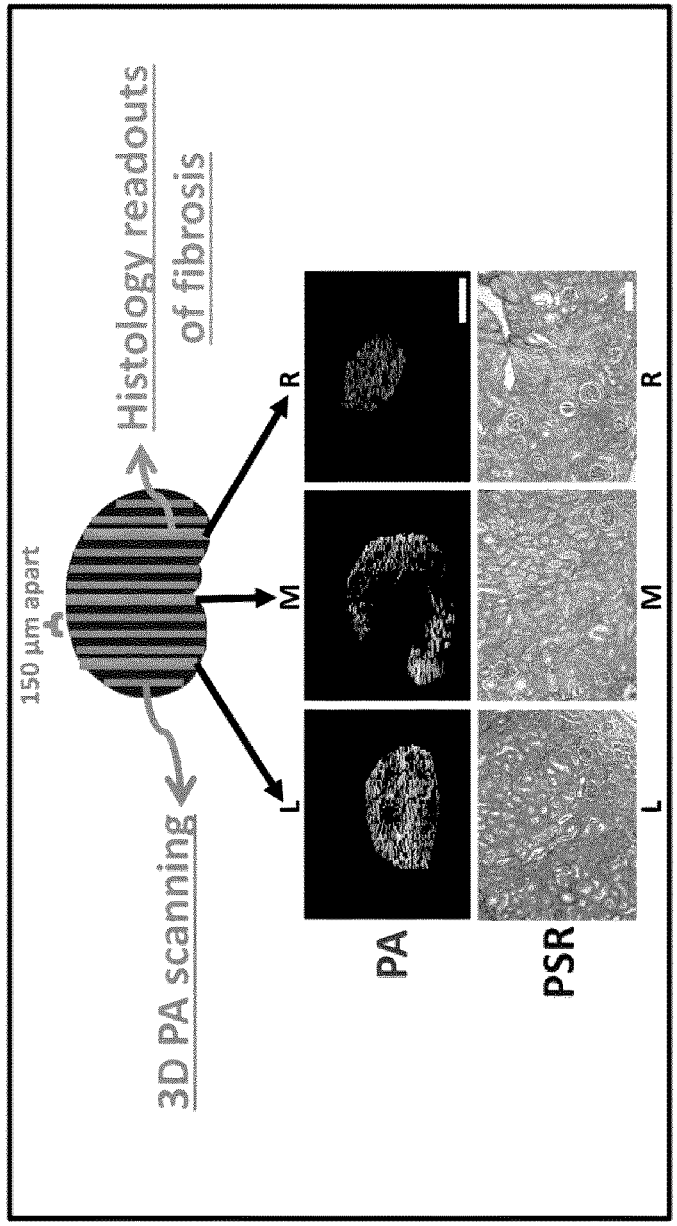
FIGS. 6A-6D show results for 3D photoacoustic (PA) imaging, which accurately quantifies whole kidney fibrotic burden in a murine mouse model of fibrosis.

To assess the ability of 3D kidney scanning to capture intra-kidney variation in collagen content, fibrosis was measured histologically from predefined sections within the kidney (see FIG. 6A), with the resulting histologic values being directly compared with collagen scores derived from PA images taken at the precise locations of the histologically stained sections. Along with the conventional histology results in FIG. 6A, the 3D PA imaging according to the teachings herein demonstrated that collagen content is distributed heterogeneously throughout the kidney. For example, FIG. 6A shows representative PA and histology collagen maps. The PA maps are from multiple sections within the kidney (L=left; M=middle; R=right). Representative histology images of each stain as a function of time post-UUO surgery are also shown in FIG. 6A. The 5 mm (PA) and 100 µm (histology) scale bar applies to all images in FIG. 6A.

Figure 6B:
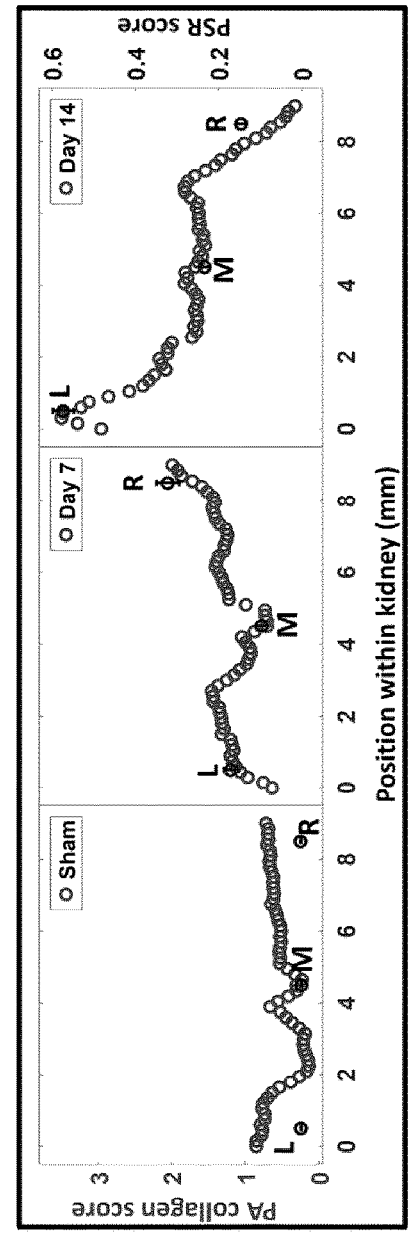

Significant PA-measured fluctuations in collagen content across the entire length of the kidney were observed, that importantly were closely mirrored by gold standard PSR-based histology quantification acquired in three locations within the kidney (labelled L for left, M for middle and R for right in FIG. 6B). For example, FIG. 6B shows Intra-kidney collagen variation for both PA (left axis) and PSR histology (right axis). Therefore, it was found that 3D photoacoustic imaging can quantify the intra-kidney variations in collagen content.

To test whether the 3D PA imaging technique of the present teachings provided additional accuracy in quantifying whole kidney fibrotic burden as compared with the single slice 2D PA imaging technique, collagen content from all the component 3D PA images from a given kidney was averaged to generate a mean PA-derived whole kidney fibrosis score. These PA fibrosis scores were found to correlate well with histologic scar estimates of mean whole kidney fibrotic burden using several different stains, but this relationship was not stronger than that derived from the single slice 2D PA imaging technique.

Figure 6C:
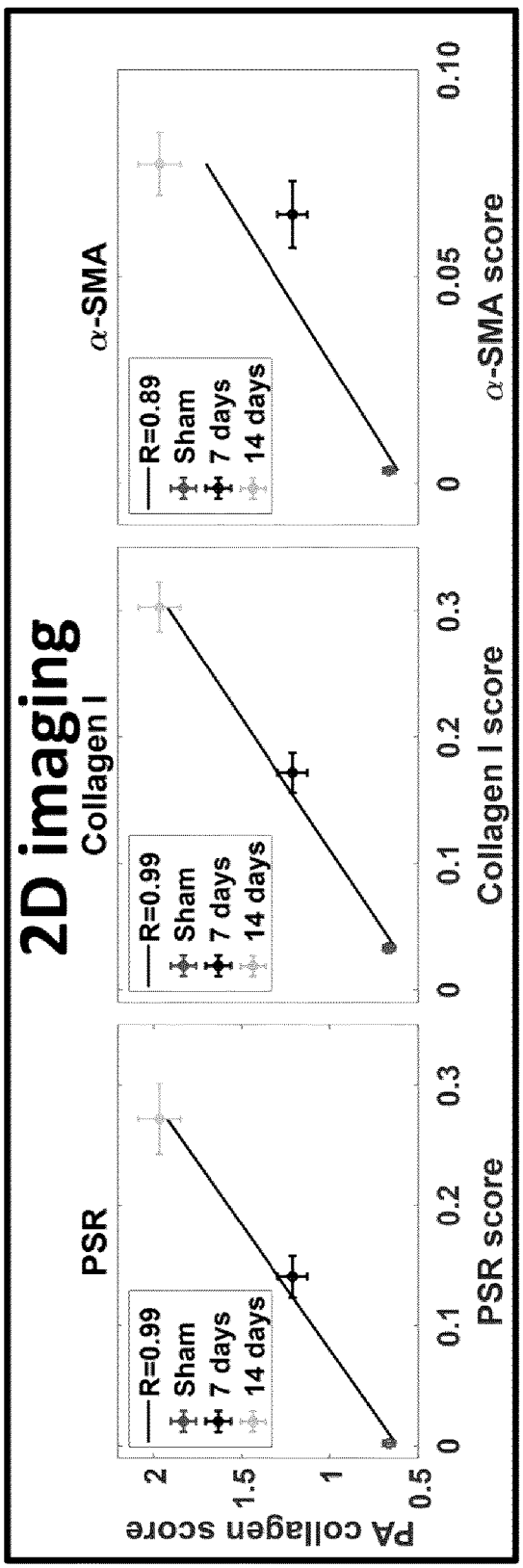
Figure 6D:
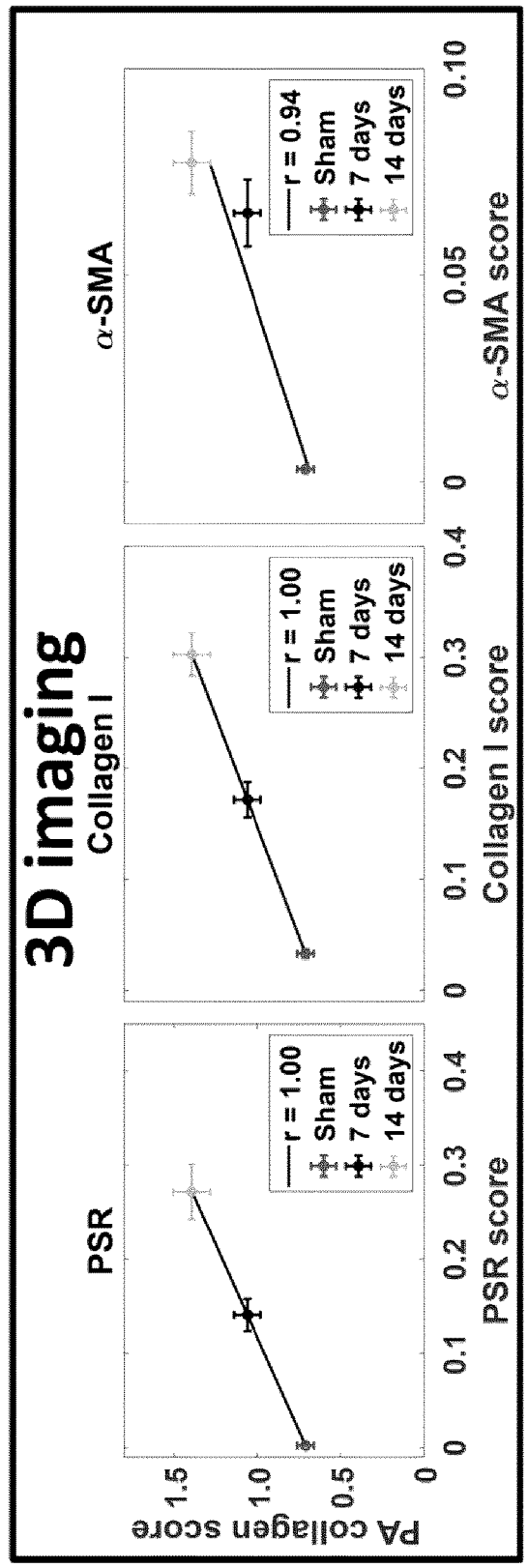

For example, FIGS. 6C and 6D show correlation between PA imaging and histology for the 2D and 3D imaging sessions, respectively. Error bars represent the standard error of the mean for five mice/time point (2D) and five mice/time point three different histological locations/mouse/timepoint (3D). The correlation coefficients are all statistically significant, with p<0.05 for each stain, in the 2D and 3D PA imaging. Accordingly, a single 2D slice (FIG. 6C) through the renal hilum was found to be as accurate an estimate of collagen content as an entire 3D sweep through the kidney (FIG. 6D), suggesting that the 2D PA technique according to the teachings herein can still capture overall renal fibrotic burden without loss of accuracy.

Taken together, the results suggest that while 3D PA imaging can quantify variations in intra-renal collagen content, a single 2D PA image through the renal hilum may be the most rapid way to accurately assess whole kidney fibrotic burden. Thus, in the setting of donor kidney fibrosis assessment during transplantation, when a quick, non-invasive estimate of fibrotic burden is required, only a single 1.5 minute 2D transverse image through the kidney may be required. For a more comprehensive assessment of collagen distribution, a 5-minute 3D sweep through a mouse kidney or a 15-minute 3D sweep through a human kidney can also be performed.

PA Imaging of Renal Collagen in a Clinically Relevant Setting

The initial studies used ex vivo mouse kidneys (roughly 1.0×0.5×0.5 cm), which are much smaller than human kidneys (roughly 10×5×5 cm). PA imaging depends both on adequate light penetration into tissue (to excite a chromophore) and the temperature of the tissue during imaging (to ensure efficient light-induced thermoelastic expansion) [28]. Since human kidneys are located generally deep within the abdominal cavity, a site that is inaccessible to most current light delivery technologies [29], in vivo photoacoustic imaging of human kidneys has generally been considered not feasible. During transplantation, however, kidneys are stored ex vivo on ice, often for several hours between their harvesting from the donor, and implantation into the recipient. Since fibrosis is an important predictor of transplant kidney outcomes that is currently inadequately assessed, experiments were conducted to determine whether PA imaging of the ex vivo transplant kidney might represent an ideal opportunity for a clinically impactful application of the PA imaging-based kidney assessment techniques of the present teachings.

Figure 7B:
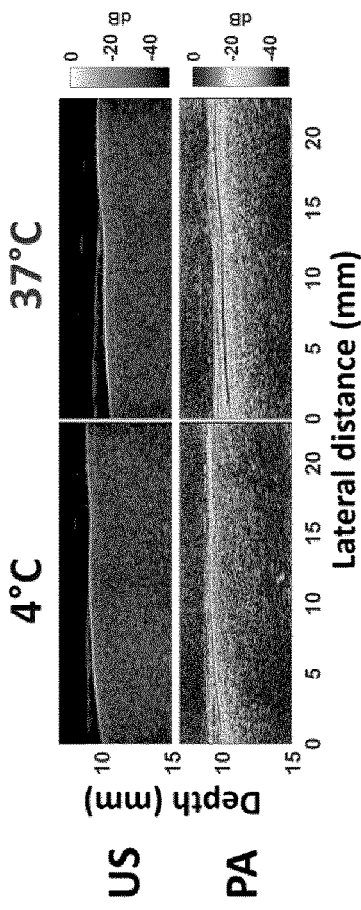
FIGS. 7A-7D show a test setup and the effect of imaging temperature on PA collagen identification.
Figure 7D:
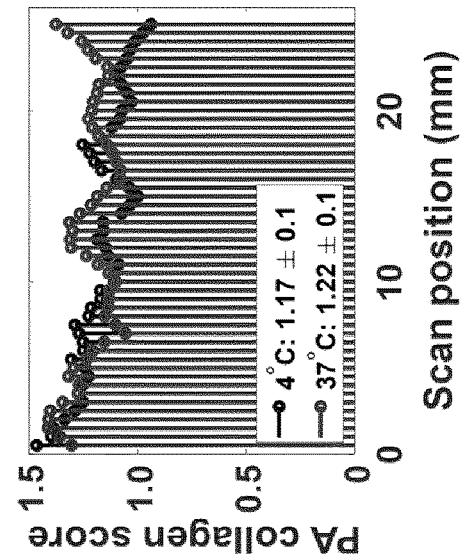
Figure 7A:
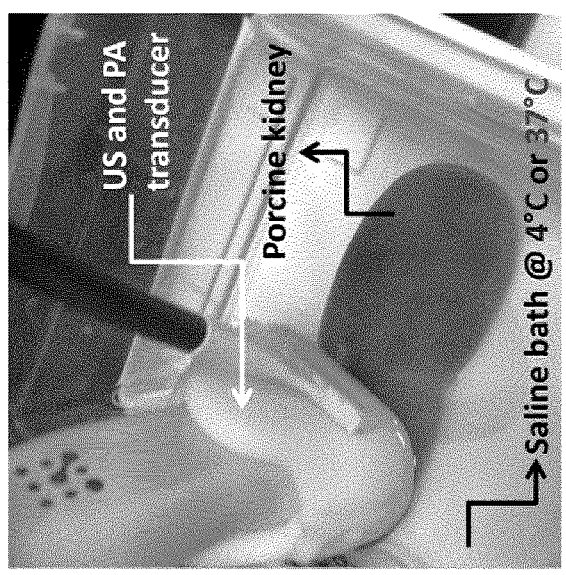
Figure 7C:
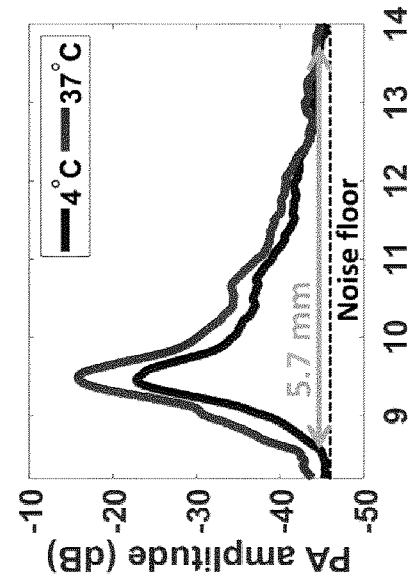

A first set of experiments for PA imaging in clinically relevant environments involved testing whether collagen PA imaging may be performed at 4° C. on pig kidneys, which are similar in size to human kidneys, to best mimic this important clinical setting. FIG. 7A shows the imaging setup for whole porcine kidney imaging in a 4° C. and a 37° C. saline bath. FIG. 7B shows representative US and PA images at both temperatures. Given the temperature sensitivity of PA signal generation [30], PA signal intensity was, as expected, reduced at 4° C. Importantly, however, the amplitude of the detected PA signal remained above noise level for nearly 6 mm below the kidney surface at both temperatures as shown in FIG. 7C.

Thus, collagen PA imaging can be successfully performed to at least 6 mm below the kidney surface even at 4° C., the temperature at which human transplant kidneys are stored while awaiting implantation into a recipient (see FIGS. 7C and 7D). FIG. 7D shows PA collagen quantification as a function of temperature and scan position within a pig kidney. The average PA collagen scores at 4° C. and 37° C. did not differ (p>0.05). Importantly, this imaging depth allowed sampling of the majority of the kidney cortex, which in a healthy kidney extends to a mean of 8 mm below the kidney surface (with more damaged kidneys having thinner cortices) [31]. Since the PA probe can be scanned across the entire kidney surface, the PA imaging technique of the present teachings can thus image roughly 75% of the entire renal cortex, in a clinically relevant setting that closely mimics human kidney transplantation.

To further assess the translational potential of the PA imaging technique of the present teachings, a study was conducted to determine whether PA imaging of human kidneys may generate similar results as the proof-of-principle mouse studies. FIG. 8A shows the human kidney PA imaging setup. FIG. 8B shows the 3D whole kidney PA imaging strategy. The bottom and top surfaces of the kidney were imaged in the orientation shown with slices taken every 0.5 mm. PA imaging was performed at 4° C. on a non-transplantable whole human kidney harvested using the same protocol as that used for actual kidney transplantation to mimic an ex vivo donor kidney awaiting implantation. Scanning over the entire kidney surface enabled the bulk of the renal cortex to be imaged. This is advantageous as the cortex is a critical part of the kidney as it is not only the site of blood filtration, but also the gateway for most of the blood flow to the medulla (the inner portion of the kidney).

FIGS. 8C and 8D show the PA quantification results obtained from imaging both the top and bottom, respectively, of the whole human kidney. Much like mouse kidneys shown in FIG. 8B, a significant variation in PA-derived collagen scores was noted as the probe scanned was across the human kidney. In particular, FIGS. 8C and 8D show PA and picrosirius red (PSR)-derived collagen scores from selected positions within the top (see FIG. 8C) and bottom of the kidney (see FIG. 8D). Each position (P1-P4) represents the locations where histological sampling was performed.

Remarkably, PA-measured spatial fluctuations in collagen closely mirrored changes noted following histologic quantification of PSR-stained serial slices through the kidney as can be seen in FIG. 8E, which shows the correlation of PA-derived collagen estimates with PSR-derived collagen scores for all measured sites. The correlation coefficient was statistically significant (Pearson rho—0.97, p<0.05). Representative PA and PSR-stained images are also shown for both sides of the kidney. The scale bar for all PA images represents 5 mm; the histology scale bar represents 100 µm.

Figure 8G:
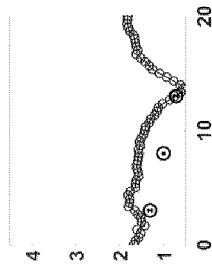
Figure 8G:
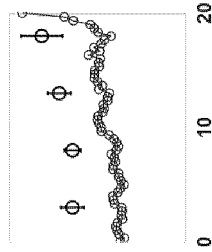
Figure 8G:
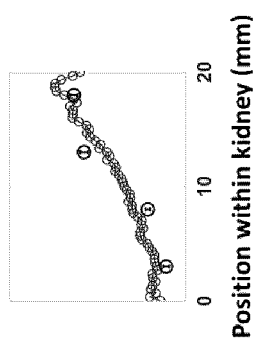
Figure 8G:
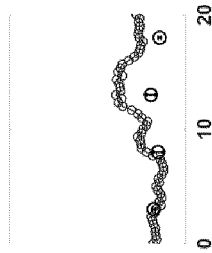
Figure 8G:
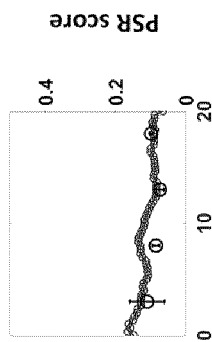

The ability of PA to quantify the collagen heterogeneity within human kidneys was also observed in the five radical nephrectomy specimens (see FIG. 8F), that like in the whole human kidney, closely correlated with variations in histologically-determined collagen measurements (see FIG. 8G). In particular, FIG. 8F shows photographs of the human kidney nephrectomy specimens. The 3D imaging orientation strategy shown in Kidney 2 applies to all imaged specimens. FIG. 8G shows the Intra-kidney collagen variation in nephrectomy specimens for both PA-derived (left axis, red line) and PSR-derived collagen scores (right axis, blue dots).

To evaluate the performance of PA imaging as a method to quantify renal cortical fibrosis across multiple human kidney samples, mean PA-derived collagen scores were compared to gold standard histologic values derived from examination of the human radical nephrectomy specimens used in the studies. For these analyses, both 2D and 3D PA imaging were performed. In particular, FIG. 9A shows representative collagen maps generated by PA imaging and corresponding images of PSR and Masson's Trichrome-stained tissue sections taken from the same regions within the kidney for five kidney samples. The scale bar for all PA images represents 5 mm, the histology scale bar represents 100 µm. FIGS. 9B and 9C show correlations between PA-based collagen scores and histology-derived fibrosis measurements using either 2D (see FIG. 9B) or 3D (see FIG. 9C) PA imaging. As expected, both 2D and 3D PA imaging quantified renal cortical fibrosis with exquisite accuracy. All correlation coefficients are statistically significant, with p<0.05 for each stain. Therefore, as was observed with the experiments on the mouse kidneys, 2D PA collagen imaging for human kidneys was as accurate as 3D PA imaging in assessing renal fibrotic burden.

Fibrosis in Other Pathologies

Fibrosis is a common feature of many chronic diseases, and is associated with up to 45% of deaths in the industrialized world [76]. Generally, it is considered to be the end result of chronic inflammatory conditions that are caused by a variety of internal and external stimuli, including genetic and metabolic disorders, autoimmune reactions, acute injury, allergic responses, radiation, chemical insults and tissue injury [77]. The abnormal deposition of collagen and other matrix proteins that is typical in organ/tissue fibrosis can lead to the disruption and distortion of the organ's morphological architecture and function [78]. These underlying changes manifest themselves in several fibrotic diseases present in many organs. For example, in the lung, idiopathic pulmonary fibrosis, radiotherapy fibrosis and scleroderma impair gas exchange [79]. In the heart, fibrosis is associated with arrhythmias, increased stiffness and systolic/diastolic disfunctions [80]. In the liver, fibrosis can cause cirrhosis/hepatitis of the liver from viral, alcohol and fatty origins, biliary disease and even portal hypertension [81]. The extracellular matrix plays an important role in the tumor microenvironment and cancer-associated fibrosis has emerged as a key regulator of cancer behavior, both as a suppressor and enhancer of tumor growth [82]. It is perhaps not surprising that significant preclinical and clinical effort has been put towards understanding the mechanism of fibrosis development and progression in order to facilitate the development of effective anti-fibrotic therapies to reduce the burden of this disorder. This study examined liver and tumor fibrosis and how the photoacoustic (PA) imaging techniques described herein can contribute to preclinical fibrosis research.

Liver Fibrosis

Obesity and elevated fasting glucose contribute to the development of nonalcoholic fatty liver disease (NAFLD), a spectrum of diseases which include hepatic steatosis, non-alcoholic steatohepatitis (NASH), fibrosis and cirrhosis of the liver [83]. Patients with NASH are at increased risk of developing hepatic fibrosis, which can progress to cirrhosis, hepatocellular carcinoma, and end-stage liver disease, warranting orthotopic liver transplantation [84]. It is projected that by 2020, NASH will become the leading indication for liver transplantation within developing countries [85]. No evidence-based treatment is currently approved for the management of NASH, making this disorder one with high unmet therapeutic need. As such, the rising prevalence of obesity and diabetes coupled with the lack of treatments for liver fibrosis have led to the significant expansion of both academic and industrial research and development pipelines [86].

In order to facilitate the advancement of both novel diagnosis and antifibrotic therapies in the liver, a plethora of animal models have been developed for studying the pathogenesis of NASH and identifying molecular targets involved in the onset and the progression of fibrosis [87]. These animal models of liver fibrosis are most commonly employed in mice and rats, before extending to larger rabbits or non-human primates. However, less than 10% of all anti-fibrotic drug candidates progress to commercialization [88]. A major reason for this low rate of clinical translation is the lack of a way to safely and accurately quantify collagen content non-invasively. Indeed, the only method available for measuring liver collagen deposition directly remains histology. Histology requires sacrifice of the animal in order to extract the liver. This is a very low throughput process as animals must be sacrificed at more than one timepoint in order to study fibrosis development or therapy efficacy longitudinally. Moreover, specialized histological stains are employed in order to visualize various components of liver metabolism, including collagen deposition. These stains are often expensive, and their cost prohibits the volumetric evaluation of fibrosis in the whole organ, as researchers rely on taking a few representative slices, amounting to less than 1% of the total volume. Depending on the complexity of the stain or stains involved, the preparation process and microscopy-based analysis of the histology slides incurs additional expenses and typically is only available after several days. Furthermore, it is not possible to study liver fibrosis in-vivo, using conventional techniques, without extracting the organ, thus contributing to the disconnect between animal studies and human translation [89]. However, the PA imaging techniques described herein can be used for quantifying the degree of liver collagen and for measuring fibrosis in-vivo for small animal models.

Experimental Details

FIG. 11 shows a schematic of the experimental procedure for inducing murine liver fibrosis. Twenty-eight mice were randomized to receive thrice weekly intraperitoneal injections of corn oil (n=12) or carbon tetrachloride ($CCl_4$, 2 µL/g body weight, n=31) dissolved in corn oil. $CCl_4$ is a known liver chemotoxin that is used to develop fibrosis in mice, followed by efficient progression to cirrhosis and hepatocellular carcinoma [9]. The injections were provided for six weeks, and overall health was monitored prior to being sacrificed. The liver was extracted, and PA imaging was performed using the exact same protocol and instrumentation used for the UUO mouse model described above, which involves illuminations of the liver samples at 680, 725 and 755 nm wavelengths before implementing the spectral unmixing algorithm that was tested in collagen phantoms and in mouse, pig, and human kidneys. For each mouse liver, a PA collagen map was constructed, and the average collagen score across these PA collagen maps was extracted and correlated to the equivalent histological collagen score measured by Picrosirius Red (PSR).

Results

FIG. 12A shows representative PA and histology images of the collagen deposition in mice with three levels of liver fibrosis (as determined by histology). Both techniques reveal increases in the collagen content as the fibrotic burden of the organ increases. The gold standard histologic quantification of fibrillar collagen closely mirrors the PA imaging collagen maps. In addition, PA imaging is also capable of capturing intra-liver fibrotic spatial heterogeneity. Importantly, correlation analysis (FIG. 12B) demonstrated good agreement between PA imaging-based collagen scores and gold standard histology measurements. The Pearson correlation coefficient was r=0.99, validating the accuracy of the novel unmixing approach described in accordance with the teachings herein. This level of accuracy is comparable to the findings observed in the kidneys.

Tumor Fibrosis

The tumor microenvironment contains a complex collection of cancer cells (malignant or non-malignant), blood and lymphatic vessels. These components are all embedded in an extracellular matrix [90]. Similar to other organs such as kidney and liver, this matrix consists of interlocked meshes of water, mineral, proteoglycans, and fibrous proteins such as collagen, all of which are secreted by the very same cells that reside within the scaffold, the fibroblasts [91]. Collagen contributes to cancer cell invasion, metastasis and proliferation, resistance to treatments, intratumoral vessel and hypoxia regulation and tumorigenesis [92]. In fact, fibrosis is beginning to be recognized as a hallmark of cancer, as up to 20% of all malignancies are linked to chronic inflammation-related fibrosis including hepatocellular, gastric, esophageal, head and neck, colon, pancreatic, cervix, and vulvar cancers [82], [93]. Depletion of the extracellular matrix has been shown to improve survival by decompressing blood vessels and allowing chemotherapy delivery [94], [95]. At the same time, in contrast to the data discussed above, a growing body of evidence argues that tumor-related fibrosis limits cancer growth and progression by restricting cancer initiation, proliferation and metastasis [96-100]. These dichotomies arise due to the complexities of the molecular biology of cancer and their constant evolution. Importantly, they highlight the need for preclinical studies to understand the role of fibrosis in cancer. The potential of the PA imaging techniques described herein for measuring tumor collagen in-vivo in a longitudinal and non-invasive manner were examined in this study.

Experimental Details

These proof-of-principle experiments using prostate cancer (PC3) cells inoculated in the right, upper hind leg of SCID mice. The tumors were grown to 8-10 mm in maximum diameter for approximately 4-6 weeks. PA imaging of these tumors was performed at various time-points, including 0, 2, and 24 hrs post-study initiation. The same instrumentation and methodology including the spectral unmixing algorithm that was employed in kidneys and livers was used to estimate collagen inside tumors at each timepoint. Representative PSR histology measures of collagen were acquired at 24 h post-treatment when the mice were sacrificed. The PSR collagen scores were compared with the PA estimates obtained at the 24 h timepoint.

Results

Figure 14A:
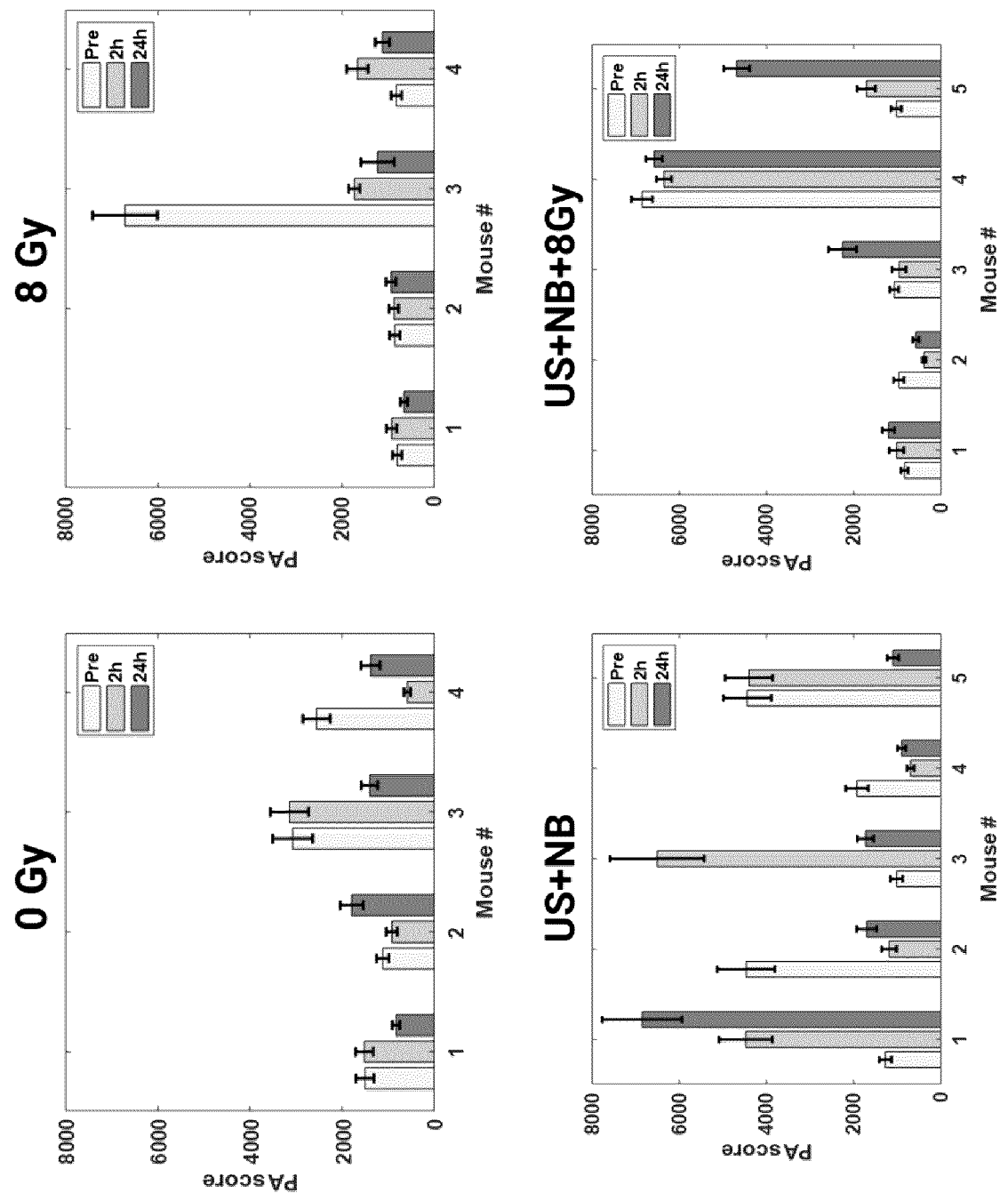
FIG. 14A shows a summary of the PA measured collagen scores for mice in each of the treatment categories as a function of time post-treatment.
Figure 14B:
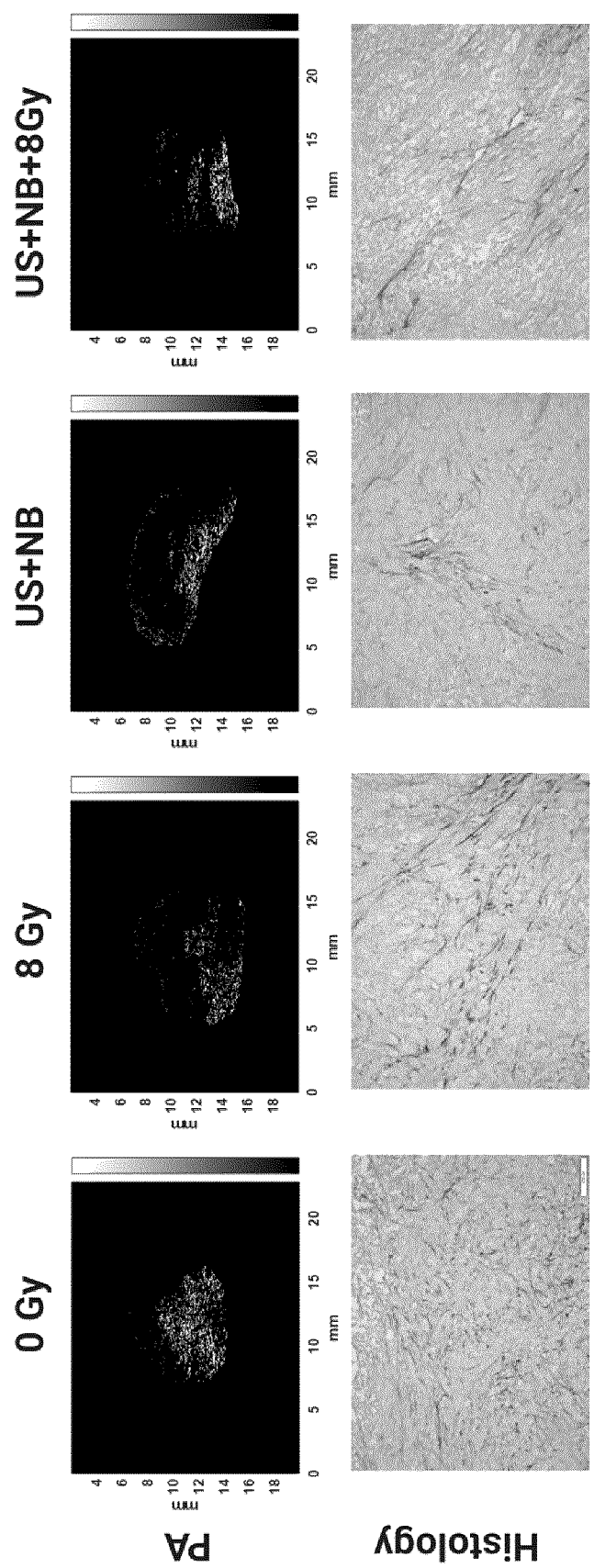
FIG. 14B shows representative PA and histology maps of collagen distribution in tumors.
Figure 14C:
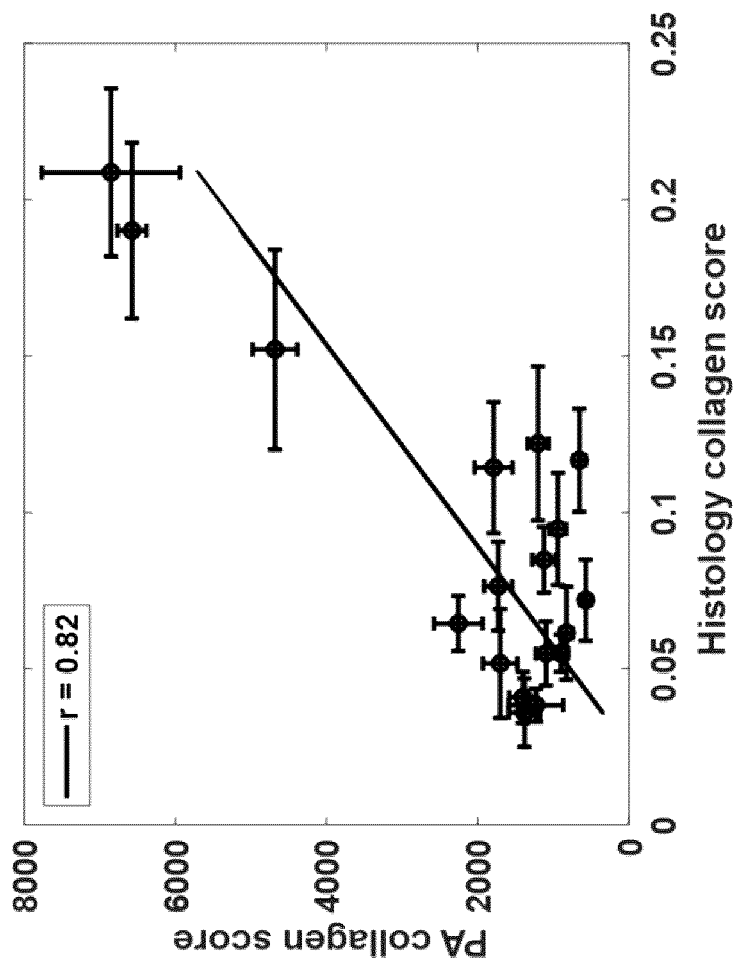
FIG. 14C shows a plot of the correlation between the PA and histology collagen scores for all the mice imaged in the tumor collagen study, obtained at the 24 h timepoint.

FIG. 14A summarizes the PA-measured collagen scores for all the mice in this study at various imaging timepoints. These measurements represent the first measurements of collagen in-vivo in tumors using PA imaging. As shown by this quantification, it is possible to measure the degree of collagen present in tumors several times within the same animal. This measurement may be performed without extracting the tumor and performing ex-vivo scanning. The PA and histology collagen maps are shown in FIG. 14B. Both techniques reveal the spatial heterogeneity that accompanies the tumor microenvironment, with some groups having a higher degree of collagen present compared to others. FIG. 14C supports these findings and demonstrates the overall agreement between PA measures of collagen with those of histology. This work can be potentially extended to both study the formation of collagen in growing tumors over time as well as the impact of collagen-targeting treatments in a longitudinal fashion.

While the applicant's teachings described herein are in conjunction with various embodiments for illustrative purposes, it is not intended that the applicant's teachings be limited to such embodiments as the embodiments described herein are intended to be examples. On the contrary, the applicant's teachings described and illustrated herein encompass various alternatives, modifications, and equivalents, without departing from the embodiments described herein, the general scope of which is defined in the appended claims.

REFERENCES

[1] "Canadian Organ Replacement Register Metadata (CORR) | CIHI—Treatment of End-Stage Organ Failure in Canada," 2 May 2019. [Online]. Available: https://www.cihi.ca/en/canadian-organ-replacement-register-metadata-corr. [Accessed: 28 Jul. 2019].
[2] United States Renal Data System (USRDS), "Annual Data Report," 2018 *Annual Data Report*. [Online]. Available: https://www.usrds.org/adr.aspx. [Accessed: 26 Sep. 2019].
[3] R. A. Wolfe et al., "Comparison of mortality in all patients on dialysis, patients on dialysis awaiting transplantation, and recipients of a first cadaveric transplant," *N. Engl. J. Med.*, vol. 341, no. 23, pp. 1725-1730, December 1999.
[4] F. K. Port, R. A. Wolfe, E. A. Mauger, D. P. Berling, and K. Jiang, "Comparison of survival probabilities for dialysis patients vs cadaveric renal transplant recipients," *JAMA*, vol. 270, no. 11, pp. 1339-1343, September 1993.
[5] A. Laupacis et al., "A study of the quality of life and cost-utility of renal transplantation," *Kidney Int.*, vol. 50, no. 1, pp. 235-242, July 1996.
[6] "Facing the Facts—The Kidney Foundation of Canada | La Fondation canadienne du rein." [Online]. Available: https://www.kidney.ca/facing-the-facts. [Accessed: 28 Jul. 2019].
[7] J. Schold, T. R. Srinivas, A. R. Sehgal, and H.-U. Meier-Kriesche, "Half of kidney transplant candidates who are older than 60 years now placed on the waiting list will die before receiving a deceased-donor transplant," *Clin. J. Am. Soc. Nephrol. CJASN*, vol. 4, no. 7, pp. 1239-1245, July 2009.
[8] K. De Vusser et al., "The predictive value of kidney allograft baseline biopsies for long-term graft survival," *J. Am. Soc. Nephrol. JASN*, vol. 24, no. 11, pp. 1913-1923, November 2013.
[9] A. Srivastava et al., "The Prognostic Value of Histopathologic Lesions in Native Kidney Biopsy Specimens: Results from the Boston Kidney Biopsy Cohort Study," *J. Am. Soc. Nephrol. JASN*, vol. 29, no. 8, pp. 2213-2224, August 2018.
[10] F. M. E. G. Steegh et al., "Early loss of peritubular capillaries after kidney transplantation," *J. Am. Soc. Nephrol. JASN*, vol. 22, no. 6, pp. 1024-1029, June 2011.
[11] M. Naesens et al., "Chronic histological damage in early indication biopsies is an independent risk factor for late renal allograft failure," *Am. J. Transplant. Off. J. Am. Soc. Transplant. Am. Soc. Transpl. Surg.*, vol. 13, no. 1, pp. 86-99, January 2013.
[12] D. Tampe and M. Zeisberg, "Potential approaches to reverse or repair renal fibrosis," *Nat. Rev. Nephrol.*, vol. 10, no. 4, pp. 226-237, April 2014.
[13] C. J. Wang, J. B. Wetmore, G. S. Crary, and B. L. Kasiske, "The Donor Kidney Biopsy and Its Implications in Predicting Graft Outcomes: A Systematic Review," *Am. J. Transplant. Off. J. Am. Soc. Transplant. Am. Soc. Transpl. Surg.*, vol. 15, no. 7, pp. 1903-1914, July 2015.
[14] H. J. Wang, C. M. Kjellstrand, S. M. Cockfield, and K. Solez, "On the influence of sample size on the prognostic accuracy and reproducibility of renal transplant biopsy," *Nephrol. Dial. Transplant. Off. Publ. Eur. Dial. Transpl. Assoc.-Eur. Ren. Assoc.*, vol. 13, no. 1, pp. 165-172, January 1998.
[15] W. W. Williams, D. Taheri, N. Tolkoff-Rubin, and R. B. Colvin, "Clinical role of the renal transplant biopsy," *Nat. Rev. Nephrol.*, vol. 8, no. 2, pp. 110-121, January 2012.
[16] G. Leung et al., "Could MRI Be Used To Image Kidney Fibrosis? A Review of Recent Advances and Remaining Barriers," *Clin. J. Am. Soc. Nephrol. CJASN*, vol. 12, no. 6, pp. 1019-1028, June 2017.
[17] L. V. Wang and S. Hu, "Photoacoustic tomography: in vivo imaging from organelles to organs," *Science*, vol. 335, no. 6075, pp. 1458-1462, March 2012.
[18] L. V. Wang and J. Yao, "A practical guide to photoacoustic tomography in the life sciences," *Nat. Methods*, vol. 13, no. 8, pp. 627-638, August 2016.
[19] J. Yao and L. V. Wang, "Photoacoustic tomography: fundamentals, advances and prospects," *Contrast Media Mol. Imaging*, vol. 6, no. 5, pp. 332-345, October 2011.
[20] R. J. Paproski, A. Heinmiller, K. Wachowicz, and R. J. Zemp, "Multi-wavelength photoacoustic imaging of inducible tyrosinase reporter gene expression in xenograft tumors," *Sci. Rep.*, vol. 4, no. 1, May 2015.
[21] B. Cox, J. G. Laufer, S. R. Arridge, and P. C. Beard, "Quantitative spectroscopic photoacoustic imaging: a review," *J. Biomed. Opt.*, vol. 17, no. 6, p. 061202, June 2012.

[22] J. Laufer et al., "In vivo photoacoustic imaging of mouse embryos," *J. Biomed. Opt.*, vol. 17, no. 6, pp. 0612201-0612208, 2012.

[23] D. Razansky et al., "Multispectral opto-acoustic tomography of deep-seated fluorescent proteins in vivo," *Nat. Photonics*, vol. 3, no. 7, pp. 412-417, July 2009.

[24] A. A. Eddy, "Molecular insights into renal interstitial fibrosis," *J. Am. Soc. Nephrol. JASN*, vol. 7, no. 12, pp. 2495-2508, December 1996.

[25] V. Ntziachristos, J. Ripoll, L. V. Wang, and R. Weissleder, "Looking and listening to light: the evolution of whole-body photonic imaging," *Nat. Biotechnol.*, vol. 23, no. 3, pp. 313-320, March 2005.

[26] R. L. Chevalier, M. S. Forbes, and B. A. Thornhill, "Ureteral obstruction as a model of renal interstitial fibrosis and obstructive nephropathy," *Kidney Int.*, vol. 75, no. 11, pp. 1145-1152, June 2009.

[27] A. Kirpalani et al., "Magnetic Resonance Elastography to Assess Fibrosis in Kidney Allografts," *Clin. J. Am. Soc. Nephrol. CJASN*, vol. 12, no. 10, pp. 1671-1679, October 2017.

[28] I. Y. Petrova et al., "Optoacoustic monitoring of blood hemoglobin concentration: a pilot clinical study," *Opt. Lett.*, vol. 30, no. 13, pp. 1677-1679, 2005.

[29] T. Vu, D. Razansky, and J. Yao, "Listening to tissues with new light: recent technological advances in photoacoustic imaging," *J. Opt.*, 2019.

[30] P. Shao, B. Cox, and R. J. Zemp, "Estimating optical absorption, scattering, and Grueneisen distributions with multiple-illumination photoacoustic tomography," *Appl. Opt.*, vol. 50, no. 19, pp. 3145-3154, 2011.

[31] S. Moghazi et al., "Correlation of renal histopathology with sonographic findings," *Kidney Int.*, vol. 67, no. 4, pp. 1515-1520, April 2005.

[32] F. G. Cosio et al., "Kidney allograft fibrosis and atrophy early after living donor transplantation," *Am. J. Transplant. Off. J. Am. Soc. Transplant. Am. Soc. Transpl. Surg.*, vol. 5, no. 5, pp. 1130-1136, May 2005.

[33] P. S. Rao et al., "A comprehensive risk quantification score for deceased donor kidneys: the kidney donor risk index," *Transplantation*, vol. 88, no. 2, pp. 231-236, July 2009.

[34] C. J. E. Watson, R. J. Johnson, R. Birch, D. Collett, and J. A. Bradley, "A simplified donor risk index for predicting outcome after deceased donor kidney transplantation," Transplantation, vol. 93, no. 3, pp. 314-318, February 2012.

[35] A. Debout et al., "Each additional hour of cold ischemia time significantly increases the risk of graft failure and mortality following renal transplantation," *Kidney Int.*, vol. 87, no. 2, pp. 343-349, February 2015.

[36] J. E. Locke, D. L. Segev, D. S. Warren, F. Dominici, C. E. Simpkins, and R. A. Montgomery, "Outcomes of kidneys from donors after cardiac death: implications for allocation and preservation," *Am. J. Transplant. Off. J. Am. Soc. Transplant. Am. Soc. Transpl. Surg.*, vol. 7, no. 7, pp. 1797-1807, July 2007.

[37] J. D. Mezrich et al., "Differential Outcomes of Expanded-Criteria Donor Renal Allografts According to Recipient Age," *Clin. J. Am. Soc. Nephrol. CJASN*, vol. 7, no. 7, pp. 1163-1171, July 2012.

[38] O. Aubert et al., "Long term outcomes of transplantation using kidneys from expanded criteria donors: prospective, population based cohort study," *BMJ*, vol. 351, p. h3557, July 2015.

[39] A. O. Ojo et al., "Survival in recipients of marginal cadaveric donor kidneys compared with other recipients and wait-listed transplant candidates," *J. Am. Soc. Nephrol. JASN*, vol. 12, no. 3, pp. 589-597, March 2001.

[40] R. Arndt et al., "Noninvasive evaluation of renal allograft fibrosis by transient elastography—a pilot study," *Transpl. Int. Off. J. Eur. Soc. Organ Transplant.*, vol. 23, no. 9, pp. 871-877, September 2010.

[41] L. Li et al., "Single-impulse panoramic photoacoustic computed tomography of small-animal whole-body dynamics at high spatiotemporal resolution," *Nat. Biomed. Eng.*, vol. 1, no. 5, p. 0071, May 2017.

[42] F. Knieling et al., "Multispectral Optoacoustic Tomography for Assessment of Crohn's Disease Activity," *N. Engl. J. Med.*, vol. 376, no. 13, pp. 1292-1294, 2017.

[43] E. I. Neuschler et al., "A Pivotal Study of Optoacoustic Imaging to Diagnose Benign and Malignant Breast Masses: A New Evaluation Tool for Radiologists," *Radiology*, p. 172228, November 2017.

[44] L. Lin et al., "Single-breath-hold photoacoustic computed tomography of the breast," *Nat. Commun.*, vol. 9, no. 1, p. 2352, 15 2018.

[45] P. J. van den Berg, R. Bansal, K. Daoudi, W. Steenbergen, and J. Prakash, "Preclinical detection of liver fibrosis using dual-modality photoacoustic/ultrasound system," *Biomed. Opt. Express*, vol. 7, no. 12, pp. 5081-5091, November 2016.

[46] Y. Zhu et al., "Identifying intestinal fibrosis and inflammation by spectroscopic photoacoustic imaging: an animal study in vivo," *Biomed. Opt. Express*, vol. 9, no. 4, pp. 1590-1600, March 2018.

[47] H. Lei et al., "Characterizing intestinal strictures of Crohn's disease in vivo by endoscopic photoacoustic imaging," *Biomed. Opt. Express*, vol. 10, no. 5, pp. 2542-2555, May 2019.

[48] M. Schwarz, N. Garzorz-Stark, K. Eyerich, J. Aguirre, and V. Ntziachristos, "Motion correction in optoacoustic mesoscopy," *Sci. Rep.*, vol. 7, no. 1, pp. 1-9, September 2017.

[49] J. Aguirre et al., "Precision assessment of label-free psoriasis biomarkers with ultra-broadband optoacoustic mesoscopy," *Nat. Biomed. Eng.*, vol. 1, no. 5, p. 0068, May 2017.

[50] T. D. Hewitson, W. C. Boon, E. R. Simpson, E. R. Smith, and C. S. Samuel, "Estrogens do not protect, but androgens exacerbate, collagen accumulation in the female mouse kidney after ureteric obstruction," *Life Sci.*, vol. 158, pp. 130-136, August 2016.

[51] R. S. Hijmans et al., "Urinary collagen degradation products as early markers of progressive renal fibrosis," *J. Transl. Med.*, vol. 15, March 2017.

[52] R. D. Billow and P. Boor, "Extracellular Matrix in Kidney Fibrosis: More Than Just a Scaffold," *J. Histochem. Cytochem. Off. J. Histochem. Soc.*, p. 22155419849388, May 2019.

[53] Q. Yuan, R. J. Tan, and Y. Liu, "Myofibroblast in Kidney Fibrosis: Origin, Activation, and Regulation," in *Renal Fibrosis: Mechanisms and Therapies*, B.-C. Liu, H.-Y. Lan, and L.-L. Lv, Eds. Singapore: Springer Singapore, 2019, pp. 253-283.

[54] S. Ricard-Blum, G. Baffet, and N. Théret, "Molecular and tissue alterations of collagens in fibrosis," *Matrix Biol. J. Int. Soc. Matrix Biol.*, vol. 68-69, pp. 122-149, 2018.

[55] M. A. Karsdal et al., "Novel insights into the function and dynamics of extracellular matrix in liver fibrosis," *Am. J. Physiol. Gastrointest. Liver Physiol.*, vol. 308, no. 10, pp. G807-830, May 2015.

[56] K. M. Mak, C. Y. M. Png, and D. J. Lee, "Type V Collagen in Health, Disease, and Fibrosis," *Anat. Rec. Hoboken NJ 2007*, vol. 299, no. 5, pp. 613-629, May 2016.

[57] H. Yang and Z. Shu, "The extraction of collagen protein from pigskin," 2014.

[58] A. Needles et al., "Development and initial application of a fully integrated photoacoustic micro-ultrasound system," *IEEE Trans. Ultrason. Ferroelectr. Freq. Control*, vol. 60, no. 5, pp. 888-897, May 2013.

[59] D. A. Belsley, E. Kuh, and R. E. Welsch, "Detecting and Assessing Collinearity," in *Regression Diagnostics*, John Wiley & Sons, Ltd, 2005, pp. 85-191

[60] S. G. Szeto et al., "YAP/TAZ Are Mechanoregulators of TGFβ-Smad Signaling and Renal Fibrogenesis," *J. Am. Soc. Nephrol.*, vol. 27, no. 10, pp. 3117-3128, October 2016.

[61] R. A. Fisher, "Statistical Methods for Research Workers," in *Breakthroughs in Statistics: Methodology and Distribution*, S. Kotz and N. L. Johnson, Eds. New York, NY: Springer New York, 1992, pp. 66-70.

[62] G. A. F. Seber and A. J. Lee, *Linear Regression Analysis*. John Wiley & Sons, 2012.

[63] "S. Prahl, Tabulated data from various sources, http://omlc.ogi.edu/spectra."

[64] S. K. V. Sekar et al., "Diffuse optical characterization of collagen absorption from 500 to 1700 nm," *J. Biomed. Opt.*, vol. 22, no. 1, p. 15006, 01 2017.

[65] B. T. Cox, S. R. Arridge, K. P. Köstli, and P. C. Beard, "Two-dimensional quantitative photoacoustic image reconstruction of absorption distributions in scattering media by use of a simple iterative method," *Appl. Opt.*, vol. 45, no. 8, pp. 1866-1875, March 2006.

[66] R. J. Zemp, "Quantitative photoacoustic tomography with multiple optical sources," *Appl. Opt.*, vol. 49, no. 18, pp. 3566-3572, June 2010.

[67] A. Pulkkinen, B. T. Cox, S. R. Arridge, H. Goh, J. P. Kaipio, and T. Tarvainen, "Direct Estimation of Optical Parameters from Photoacoustic Time Series in Quantitative Photoacoustic Tomography," *IEEE Trans. Med. Imaging*, vol. 35, no. 11, pp. 2497-2508, 2016.

[68] B. T. Cox, J. G. Laufer, and P. C. Beard, "The challenges for quantitative photoacoustic imaging," presented at the Progress in Biomedical Optics and Imaging—Proceedings of SPIE, 2009, vol. 7177.

[69] L. V. Wang, "Tutorial on Photoacoustic Microscopy and Computed Tomography," *IEEE J. Sel. Top. Quantum Electron.*, vol. 14, no. 1, pp. 171-179, 2008.

[70] F. K. Port et al., "Donor characteristics associated with reduced graft survival: an approach to expanding the pool of kidney donors," *Transplantation*, vol. 74, no. 9, pp. 1281-1286, November 2002.

[71] Q. Sun et al., "Elastin imaging enables noninvasive staging and treatment monitoring of kidney fibrosis," *Sci. Transl. Med.*, vol. 11, no. 486, p. eaat4865, April 2019.

[72] B. R. Rosengard et al., "Report of the Crystal City meeting to maximize the use of organs recovered from the cadaver donor," *Am. J. Transplant. Off. J. Am. Soc. Transplant. Am. Soc. Transpl. Surg.*, vol. 2, no. 8, pp. 701-711, September 2002.

[73] P. Regensburger et al., "Detection of collagens by multispectral optoacoustic tomography as an imaging biomarker for Duchenne muscular dystrophy," *Nat. Med.*, pp. 1-11, December 2019.

[74] T.-H. Bok, E. Hysi, and M. C. Kolios, "Simultaneous assessment of red blood cell aggregation and oxygen saturation under pulsatile flow using high-frequency photoacoustics," *Biomed. Opt. Express*, vol. 7, no. 7, pp. 2769-2780, June 2016.

[75] E. Hysi, L. A. Wirtzfeld, J. P. May, E. Undzys, S.-D. Li, and M. C. Kolios, "Photoacoustic signal characterization of cancer treatment response: Correlation with changes in tumor oxygenation," *Photoacoustics*, vol. 5, pp. 25-35, March 2017.

[76] T. A. Wynn, "Cellular and molecular mechanisms of fibrosis," *J. Pathol.*, vol. 214, no. 2, pp. 199-210, January 2008, doi: 10.1002/path.2277.

[77] M. Baues et al., "Fibrosis imaging: Current concepts and future directions," *Adv. Drug Deliv. Rev.*, vol. 121, pp. 9-26, November 2017, doi: 10.1016/j.addr.2017.10.013.

[78] L. A. Murray, "Editorial: The Cell Types of Fibrosis," *Front. Pharmacol.*, vol. 6, January 2016, doi: 10.3389/fphar.2015.00311.

[79] W. D. Hardie, S. W. Glasser, and J. S. Hagood, "Emerging Concepts in the Pathogenesis of Lung Fibrosis," *Am. J. Pathol.*, vol. 175, no. 1, pp. 3-16, July 2009, doi: 10.2353/ajpath.2009.081170.

[80] P. Kong, P. Christia, and N. G. Frangogiannis, "The pathogenesis of cardiac fibrosis," *Cell. Mol. Life Sci.*, vol. 71, no. 4, pp. 549-574, February 2014, doi: 10.1007/s00018-013-1349-6.

[81] R. Bataller and D. A. Brenner, "Liver fibrosis," *J. Clin. Invest.*, vol. 115, no. 2, pp. 209-218, February 2005, doi: 10.1172/JCI24282.

[82] C. Chandler, T. Liu, R. Buckanovich, and L. G. Coffman, "The double edge sword of fibrosis in cancer," *Transl. Res.*, vol. 209, pp. 55-67, July 2019, doi: 10.1016/j.trsl.2019.02.006.

[83] D. J. Chiang, M. T. Pritchard, and L. E. Nagy, "Obesity, diabetes mellitus, and liver fibrosis," *Am. J. Physiol.—Gastrointest. Liver Physiol.*, vol. 300, no. 5, pp. G697-G702, May 2011, doi: 10.1152/ajpgi.00426.2010.

[84] H. H. Hansen, M. Feigh, S. S. Veidal, K. T. Rigbolt, N. Vrang, and K. Fosgerau, "Mouse models of nonalcoholic steatohepatitis in preclinical drug development," *Drug Discov. Today*, vol. 22, no. 11, pp. 1707-1718, November 2017, doi: 10.1016/j.drudis.2017.06.007.

[85] V. G. Agopian et al., "Liver transplantation for nonalcoholic steatohepatitis: the new epidemic," *Ann. Surg.*, vol. 256, no. 4, pp. 624-633, October 2012, doi: 10.1097/SLA.0b013e31826b4b7e.

[86] A. Nawrat, "Developing drugs for NASH: the race to market—Pharma Technology Focus | Issue 84 | July 2019." https://pharma.h5mag.com/pharma_jul19/developing_drugs_for_nash_the_race_to_market.

[87] P. Bedossa, "Pathology of non-alcoholic fatty liver disease," *Liver Int. Off. J. Int. Assoc. Study Liver*, vol. 37 Suppl 1, pp. 85-89, 2017, doi: 10.1111/liv.13301.

[88] A. A. Seyhan, "Lost in translation: the valley of death across preclinical and clinical divide—identification of problems and overcoming obstacles," *Transl. Med. Commun.*, vol. 4, no. 1, p. 18, November 2019, doi: 10.1186/s41231-019-0050-7.

[89] Y. Popov and D. Schuppan, "Targeting liver fibrosis: strategies for development and validation of antifibrotic therapies," *Hepatol. Baltim. Md*, vol. 50, no. 4, pp. 1294-1306, October 2009, doi: 10.1002/hep.23123.

[90] R. K. Jain, "An Indirect Way to Tame Cancer," *Sci. Am.*, vol. 310, no. 2, pp. 46-53, 2014.

[91] C. Walker, E. Mojares, and A. del Rio Hernandez, "Role of Extracellular Matrix in Development and Cancer Progression," *Int. J. Mol. Sci.*, vol. 19, no. 10, October 2018, doi: 10.3390/ijms19103028.

[92] S. Xu et al., "The role of collagen in cancer: from bench to bedside," *J. Transl. Med.*, vol. 17, no. 1, p. 309, September 2019, doi: 10.1186/s12967-019-2058-1

[93] B. B. Aggarwal, R. V. Vijayalekshmi, and B. Sung, "Targeting inflammatory pathways for prevention and therapy of cancer: short-term friend, long-term foe," *Clin. Cancer Res. Off. J. Am. Assoc. Cancer Res.*, vol. 15, no. 2, pp. 425-430, January 2009, doi: 10.1158/1078-0432.CCR-08-0149.

[94] B. Diop-Frimpong, V. P. Chauhan, S. Krane, Y. Boucher, and R. K. Jain, "Losartan inhibits collagen I synthesis and improves the distribution and efficacy of nanotherapeutics in tumors," *Proc. Natl. Acad. Sci. U.S.A*, vol. 108, no. 7, pp. 2909-2914, February 2011, doi: 10.1073/pnas.1018892108.

[95] J. D. Martin, D. Fukumura, D. G. Duda, Y. Boucher, and R. K. Jain, "Reengineering the Tumor Microenvironment to Alleviate Hypoxia and Overcome Cancer Heterogeneity," *Cold Spring Harb. Perspect. Med.*, vol. 6, no. 12, December 2016, doi: 10.1101/cshperspect.a027094.

[96] B. C. Ozdemir et al., "Depletion of carcinoma-associated fibroblasts and fibrosis induces immunosuppression and accelerates pancreas cancer with reduced survival," *Cancer Cell*, vol. 25, no. 6, pp. 719-734, June 2014, doi: 10.1016/j.ccr.2014.04.005.

[97] S. Bruno, F. Collino, M. C. Deregibus, C. Grange, C. Tetta, and G. Camussi, "Microvesicles derived from human bone marrow mesenchymal stem cells inhibit tumor growth," *Stem Cells Dev.*, vol. 22, no. 5, pp. 758-771, March 2013, doi: 10.1089/scd.2012.0304.

[98] T. Alkasalias et al., "Inhibition of tumor cell proliferation and motility by fibroblasts is both contact and soluble factor dependent," *Proc. Natl. Acad. Sci. U.S.A*, vol. 111, no. 48, pp. 17188-17193, December 2014, doi: 10.1073/pnas.1419554111.

[99] K. Shin et al., "Hedgehog signaling restrains bladder cancer progression by eliciting stromal production of urothelial differentiation factors," *Cancer Cell*, vol. 26, no. 4, pp. 521-533, October 2014, doi: 10.1016/j.cce11.2014.09.001.

[100] E. J. Kim et al., "Pilot clinical trial of hedgehog pathway inhibitor GDC-0449 (vismodegib) in combination with gemcitabine in patients with metastatic pancreatic adenocarcinoma," *Clin. Cancer Res. Off. J. Am. Assoc. Cancer Res.*, vol. 20, no. 23, pp. 5937-5945, December 2014, doi: 10.1158/1078-0432.CCR-14-1269.

The invention claimed is:

1. An imaging system for performing collagen assessment of an object using Photoacoustic (PA) Image data obtained for the object, wherein the system comprises:
 a data store comprising program instructions for performing the collagen assessment for the object; and
 a processing unit that is coupled to the data store, the processing unit, when executing the program instructions, being configured to:
  control a light source for generating a plurality of light stimulus signals each having a unique wavelength to provide at least three wavelengths related to chromophores including collagen, oxyhemoglobin and deoxyhemoglobin, the at least three wavelengths being less than 1000 nm and being selected using spectral unmixing wherein a Variance Inflation Factor is minimized;
  acquiring RF acoustic response signals when the light stimulus signals are shone on a portion of the object;
  obtain beamformed PA image data for the object from the RF acoustic response signals;
  perform spectral decomposition on the beamformed PA image data using the at least three wavelengths to obtain data that is used for generating at least one collagen map; and
  determine a collagen score for the at least one collagen map.

2. The system of claim 1, wherein the processing unit is configured to use the data obtained from the spectral decomposition for generating at least one oxyhemoglobin map and at least one deoxyhemoglobin map; and/or the processing unit is further configured to compare the collagen score with a collagen threshold to assess an amount of collagen in the object.

3. The system of claim 1, wherein the at least three wavelengths are in the range of 680 to 930 nm.

4. The system of claim 3, wherein the at least three wavelengths are within 10% to 20% of 680 nm, 725 nm and 755 nm.

5. The system of claim 4, wherein the at least three wavelengths are 680 nm, 725 nm and 755 nm.

6. The system of claim 1, wherein the collagen score is determined for a given collagen map by determining a mean pixel value, a median pixel value or a mode pixel value from the collagen map.

7. The system of claim 1, wherein there are a plurality of collagen maps each having a collagen score to provide a plurality of collagen scores and an overall collagen score is obtained by determining a mean, a median or a mode from the plurality of collagen scores.

8. The system of claim 1, wherein the beamformed PA image data are obtained from the data store.

9. The system of claim 1, wherein the system further comprises a probe for performing 2D PA imaging, wherein the probe includes:
the light source, the light source being configured to generate the plurality of light stimulus signals for illuminating the portion of the object, a first portion of the light stimulus signals having a first wavelength of the at least three wavelengths, a second portion of the light stimulus signals having a second wavelength of the at least three wavelengths and a third portion of the light stimulus signals having a third wavelength of the at least three wavelengths;
a transducer for sensing RF acoustic response signals that are generated by the portion of the object in response to the light stimulus signals; and
an aperture at a distal portion of the probe through which the light stimulus signals are outputted to illuminate the portion of the object and through which the RF acoustic response signals are received for sensing by the transducer.

10. The system of claim 9, wherein the probe further comprises:
a moveable mount that is affixed to a moveable portion of the probe for moving the aperture of probe during PA imaging; and
a motor that is operably connected to the moveable mount to move the moveable mount so that the aperture of the probe moves according to a scan trajectory during PA imaging of the object.

11. The system of claim 9, wherein the object is a kidney and during 2D PA imaging, the aperture of the probe is positioned to obtain PA image data for a transverse slice through a longest point of the kidney.

12. The system of claim 9, wherein the object is a kidney and during 3D PA imaging, the aperture of the probe is moved to a plurality of positions separated by a predetermined interval across the entire kidney to obtain 2D PA image data at each position to capture intra-kidney variation in collagen content.

13. The system of claim 12, wherein the predetermined interval is between 50 to 300 µm, and is more preferably 150 µm.

14. The system of claim 9, wherein the system further comprises:
an analog to digital converter for converting the sensed RF acoustic response signals into digitized RF acoustic response signals, and
the processing unit is configured to perform beamforming and noise reduction on the digitized RF acoustic response signals to generate the beamformed PA image data.

15. The system of claim 1, wherein the object is a tumour or tissue, or an organ including liver, intestines, heart, lung, skin, muscles, eyes, or pancreas.

16. The system of claim 1, wherein the spectral decomposition comprises spectral unmixing.

17. The system of claim 1, wherein the processing unit is further configured to perform: (a) displaying the at least one collagen map on a display, (b) electronically transmitting the collagen map to another device, (c) storing the at least one collagen map in the data store or any combination of (a), (b) and (c).

18. A method of performing collagen assessment of an object using Photoacoustic (PA) Image data obtained for the object, wherein the method is performed by a processing unit and the method comprises:
controlling a light source for generating a plurality of light stimulus signals each having a unique wavelength and together providing at least three wavelengths related to chromophores including collagen including collagen, oxyhemoglobin and deoxyhemoglobin, the at least three wavelengths being less than 1000 nm and being selected using spectral unmixing wherein a Variance Inflation Factor is minimized;
acquiring RF acoustic response signals when the light stimulus signals are shone on a portion of the object;
obtaining beamformed PA image data for the object from the RF acoustic signals;
performing spectral decomposition on the beamformed PA image data using the at least three wavelengths to obtain data that is used for generating at least one collagen map; and
determining a collagen score for the at least one collagen map.

19. The method of claim 18, wherein the object is a kidney and the method comprises storing the kidney in a solution during PA imaging.

20. The method of claim 19, wherein the solution has a temperature of 4 to 10 degrees Celsius.

21. The method of claim 19, wherein the solution comprises saline, University of Wisconsin (UW) solution, Histidine-Tryptophane-Ketoglutarate (HTK) solution, Collins solution, Celsior solution, Kyto University solution, or IGL-1 solution.

22. A method for performing a transplant of an organ, wherein the method comprises:
performing collagen assessment of the organ using a Photoacoustic (PA) Imaging based method that is defined according to claim 18 to obtain a collagen score;
comparing the collagen score with a collagen threshold to determine if the organ is suitable for transplant for a recipient patient; and
transplanting the organ into the recipient patient when the comparison indicates that the organ is suitable for transplant for the recipient patient.

23. A non-transitory computer readable medium storing program instructions that when executed by a processor, configure the processor to perform a method of performing collagen assessment of an object using Photoacoustic (PA) Image data obtained for the object, wherein the method comprises:
controlling a light source for generating a plurality of light stimulus signals each having a unique wavelength and together providing at least three wavelengths related to chromophores including collagen, oxyhemoglobin and deoxyhemoglobin, the at least three wavelengths being less than 1000 nm and being selected using spectral unmixing wherein a Variance Inflation Factor is minimized;
acquiring RF acoustic response signals when the light stimulus signals are shone on a portion of the object;

obtaining beamformed PA image data for the object from the RF acoustic signals;

performing spectral decomposition on the beamformed PA image data using the at least three wavelengths to obtain data that is used for generating at least one collagen map; and determining a collagen score for the at least one collagen map.

\* \* \* \* \*